US007041300B1

(12) United States Patent
Sanchez et al.

(10) Patent No.: US 7,041,300 B1
(45) Date of Patent: May 9, 2006

(54) VECTORS BASED ON RECOMBINANT DEFECTIVE VIRAL GENOMES, AND THEIR USE IN THE FORMULATION OF VACCINES

(75) Inventors: Luis Enjuanes Sanchez, Madrid (ES); Juan Plana Duran, Vall de Bianya-Olot (ES); Sara Alonso Villanueva, Bilbao (ES); MaLuisa Ballesteros Jarreno, Cuenca (ES); Joaquin Castilla Castrillon, Madrid (ES); José Manuel Gonzalez Martinez, Murcia (ES); Ander Izeta Parmesan, Guipúzcoa (ES); Ana Mendez Zunzunegui, Pontevedra (ES); Maria Muntion Saenz, Pamplona Navarra (ES); Zoltán Penzes, Madrid (ES); José Manuel Sanchez Morgado, Madrid (ES); Carlos Miguel Sanchez Sanchez, Madrid (ES); Cristina Smerdou Picazo, Madrid (ES); Isabel Sola Gurpegui, Navarra (ES)

(73) Assignee: Cyanamid Iberica, S.A., Madrid (ES)

( * ) Notice: Subject to any disclaimer, the term of this patent is extended or adjusted under 35 U.S.C. 154(b) by 0 days.

(21) Appl. No.: 09/155,003

(22) PCT Filed: Mar. 12, 1997

(86) PCT No.: PCT/ES97/00059

§ 371 (c)(1), (2), (4) Date: Sep. 14, 1998

(87) PCT Pub. No.: WO97/34008

PCT Pub. Date: Sep. 18, 1997

(30) Foreign Application Priority Data

Mar. 14, 1996 (ES) .............................................. 9600620

(51) Int. Cl.
*A61K 39/215* (2006.01)

(52) U.S. Cl. ................................ 424/221.1; 435/320.1; 435/236

(58) Field of Classification Search .............. 435/320.1, 435/236
See application file for complete search history.

(56) References Cited

OTHER PUBLICATIONS

Mestecky; J., et al., 1994, "Mucosal immunity and strategies for novel microbial vaccines", Acta Paediatrica Japonica 36:537–544.*

Van der Most, et al., A Domain at the 3'End of the Polymerase Gene Is Essential for Encapsidation of the Coronavirus Defective Interfering RNAs, J. Virol. vol. 65, No. 6, pp. 3219–26.

Chang, et al., A *cis*–Acting Function for the Coronavirus Leader in Defective Interfering RNA Replication, J. Virol., vol., vol. 68, No. 12, pp. 8223–31 (1994).

Médez, et al. Structure and Encapisdation of Transmissible Gastroenteritis Coronavirus (TGEV) Defective Interfering Genomes, adv. Exp. Med. and Biol. vol. 380, pp. 583–89 (1995).

Liaom et al., Coronavirus Defective–Interfering RNA as an Expression Vector: The Generation of a Pseudorecombinant Mouse Hepatitis Virus Expressing Hemagglutinin–Esterase, Virol., vol. 208, pp. 319–27 (1995).

Médez, et al., Molecular Characterization of Transmissible Gastroenteritis Coronavirus Defective Interfering Genomes: Packaging and Hetergeneity, Virol. vol. 217, pp. 495–507 (1996).

International Search Report for PCT/ES 97/00059.

* cited by examiner

*Primary Examiner*—Laurie Scheiner
*Assistant Examiner*—Jeffrey S. Parkin
(74) *Attorney, Agent, or Firm*—Finnegan, Henderson, Farabow, Garrett & Dunner, L.L.P.

(57) ABSTRACT

The vectors comprise a recombinant defective viral genome expressing at least one antigen suitable for the induction of systemic and secretory immune responses or an antibody conferring protection against an infectious agent. The defective viral genome comprises the genome of a parental virus having the viral replicase recognition signals located on ends 3' and 5', further comprising internal deletions, and wherein said defective viral genome depends on a helper virus for its replication and encapsidation. These vectors are suitable for the forming of a recombinant system comprising the aforesaid expression vector, and a helper virus. The system is suitable for the manufacture of mono- and polyvalent vaccines against infectious agents of different animal species, especially pigs, dogs and cats, and as expression vehicles for antibodies protective against infectious agents.

16 Claims, 27 Drawing Sheets

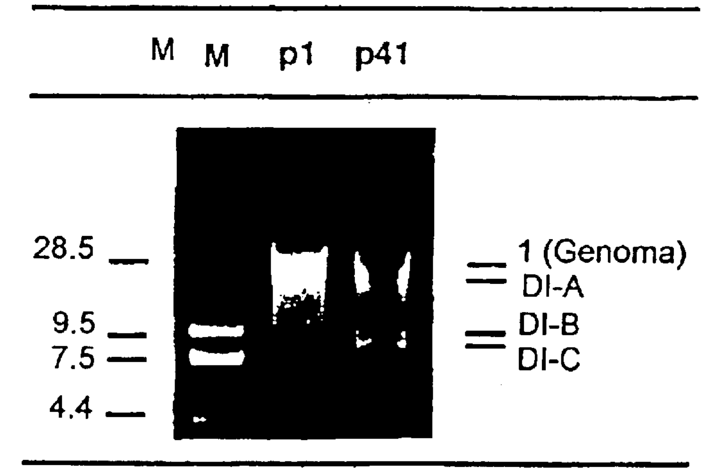
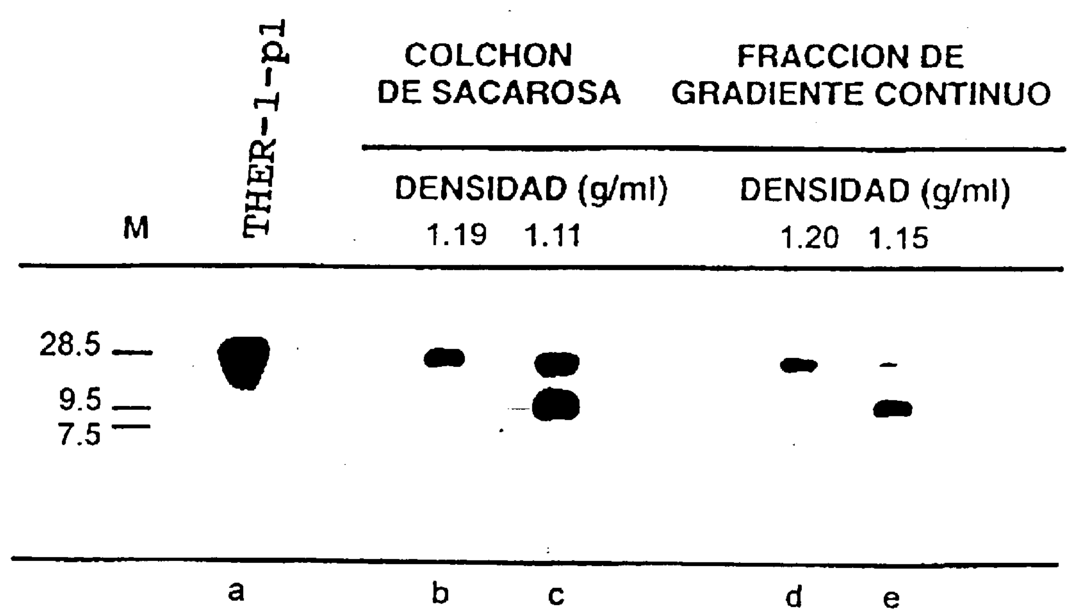
FIG.9

```
NCTTTTAAAGTAAAGTGAGTGTAGCGTGGCTATATCTCTTCTTTTACTTTAACTAGCCTTGTGCTAGATTTTGTCTTCGGACACCAACTC 90

GAACTAAACGAAATATTTGTCTTTCTATGAAATCATAGAGGACAAGCGTTGATTATTTCCATTCAGTTTGGCAATCACTCCTTGGAACGG 180

                    M  K  S  •
GGTTGAGCGAACGGTGCAGTAGGGTTCCGTCCCTATTTCGTAAGTCGCCTAGTAGTAGCGAGTGCGGTTCCGCCCGTACAACGTTGGGTA 270

GACCGGGTTCCGTCCTGTCATCTCCCTCGCCGGCCGCCAGGAGAATGAGTTCCAAACAATTCAAGATCCTTGTTAATGAGGACTATCAAG 360
                                         M  S  S  K  Q  F  K  I  L  V  N  E  D  Y  Q
TCAACGTGCCTAGTCTTCCTATTCGTGACGTGTTACAGGAAATTAAGTACTGCTACCGTAATGGATTTGAGGGCTATGTTTTCGTACCAG 450
V  N  V  P  S  L  P  I  R  D  V  L  Q  E  I  K  Y  C  Y  R  N  G  F  E  G  Y  V  F  V  P
AATACTGTCGTGACCTAGTTGATTGCGATCGTAAGGATCACTACGTCATTGGTGTTCTTGGTAACGGAGTAAGTGATCTTAAACCTGTTC 540
E  Y  C  R  D  L  V  D  C  D  R  K  D  H  Y  V  I  G  V  L  G  N  G  V  S  D  L  K  P  V
TTCTTACCGAACCCTCCGTCATGTTGCAAGGCTTTATTGTTAGAGCTAACTGCAATGGCGTTCTTGAGGACTTTGACCTTAAAATTGCTC 630
L  L  T  E  P  S  V  M  L  Q  G  F  I  V  R  A  N  C  N  G  V  L  E  D  F  D  L  K  I  A
GCACTGTCAGAGGTGCCATATATGTTGATCAATACATGTGTGGTGCTGATGGAAAACCAGTCATTGAAGGCGATTTTAAGGACTACTTCG 720
      G
R  T  V  R  G  A  I  Y  V  D  Q  Y  M  C  G  A  D  G  K  P  V  I  E  G  D  F  K  D  Y  F
GTGATGAAGACATCATTGAATTTGAAGGAGAGGAGTACCATTGCGCTTGGACAACTGTGCGCGATGAGAAACCGCTGAATCAGCAAACTC 810
G  D  E  D  I  I  E  F  E  G  E  E  Y  H  C  A  W  T  T  V  R  D  E  K  P  L  N  Q  Q  T
TCTTTACCATTCAGGAAATCCAATACAATCTGGACATTCCTCATAAATTGCCAAACTGTGCTACTAGACATGTAGCACCACCAGTCAAAA 900
L  F  T  I  Q  E  I  Q  Y  N  L  D  I  P  H  K  L  P  N  C  A  T  R  H  V  A  P  P  V  K
```

FIG. 12/1

AGAACTCTAAAATACTTCTGTCTGAAGATTACAAGAAGCTTTATGATATCTTCGGATCACCCTTTATGGGAAATGGTGACTGTCTTAGCA 890

K N S K I V L S E D Y K K L Y D I F G S P F M G N G D C L S

AATGCTTTGACACTCTTCATTTTATCGCTGCTACTCTTAGATGCCCGTGTGGTTCTGAAAGTAGCGGCGTTGGAGATTGGACTGGTTTTA 1080

K C F D T L H F I A A T L R C P C G S E S S G V G D W T G F

AGACTGCCTGTTGTGGTCTTTCTGGCAAAGTTAAGGGTGTCACTTTGGGTGATATTAAGCCTGGTGATGCTGTTGTCACTAGTATGAGCG 1170

K T A C C G L S G K V K G V T L G D I K P G D A V V T S M S

CAGGTAAGGGAGTTAAGTTCTTTGCCAATTGTGTTCTTCAATATGCTGGTGATGTTGAAGGTGTCTCCATCTGGAAAGTTATTAAAACTT 1260

A G K G V K F F A N C V L Q Y A G D V E G V S I W K V I K T

TTACAGTTGATGAGACTGTATGCACCCCTGGTTTTGAAGGCGAATTGAACGACTTCATCAAACCTGAGAGCAAATCACTAGTTGCATGCA 1350

F T V D E T V C T P G F E G E L N D F I K P E S K S L V A C

GCGTTAAAAGAGCATTCATTACTGGTGATATTGATGATGCTGTACATGATTGTATCATTACAGGAAAATTGGATCTTAGTACCAACCTTT 1440

S V K R A F I T G D I D D A V H D C I I T G K L D L S T N L

TTGGTAATGTTGGTCTATTATTCAAGAAGACTCCATGGTTTGTACAAAAGTGTGGTGCACTTTTTGTAGACGCTTGGAAAGTAGTAGAGG 1530

F G N V G L L F K K T P W F V Q K C G A L F V D A W K V V E

AGCTTTGTGGTTCACTCACACTTACATACAAGCAAATTTATGAAGTTGTAGCATCACTTTGCACTTCTGCTTTTACGATTGTAAACTACA 1620

E L C G S L T L T Y K Q I Y E V V A S L C T S A F T I V N Y

AGCCAACATTTGTGGTTCCAGACAATCGTGTTAAAGATCTTGTAGACAAGTGTGTGAAAGTTCTTGTAAAAGCATTTGATGTTTTTACGC 1710

```
AGATTATCACAATAGCTGGTATTGAGGCCAAATGCTTTGTGCTTGGTGCTAAATACCTGTTGTTCAATAATGCACTTGTCAAACTTGTCA 1800

Q I I T I A G I E A K C F V L G A K Y L L F N N A L V K L V

GTGTTAAAATCCTTGGCAAGAAGCAAAAGGGTCTTGAATGTGCATTCTTTGCTACTAGCTTGGTTGGTGCAACTGTTAATGTGACACCTA 1890

S V K I L G K K Q K G L E C A F F A T S L V G A T V N V T P

AAAGAACAGAGACTGCCACTATCAGCTTGAACAAGGTTGATGATGTTGTAGCACCAGGAGAGGGTTATATCGTCATTGTTGGTGATATGG 1980

K R T E T A T I S L N K V D D V V A P G E G Y I V I V G D M

CTTTCTACAAGAGTGGTGAATATTATTTCATGATGTCTAGTCCTAATTTTGTTCTTACTAACAATGTTTTTAAAGCAGTTAAAGTTCCAT 2070

A F Y K S G E Y Y F M M S S P N F V L T N N V F K A V K V P

CTTATGACATCGTTTATGATGTTGATAATGATACCAAAAGCAAAATGATTGCAAAACTTGGTTCATCATTTGAACAAATACCAACTGGCA 2160
                                                                        I ◄─┼─► II
S Y D I V Y D V D N D T K S K M I A K L G S S F E Q I P T G

CACAAGATCCAATTCGGTTCTGTATTGAAAATGAAGTTTGTGTTGTCTGTGGTTGTTGGCTTAACAATGGTTGCATGTGCGATCGTACTT 2250

T Q D P I R F C I E N E V C V V C G C W L N N G C M C D R T

CTATGCAGAGTTTTACTGTTGATCAAAGTTATTTAAACGACTGCCGGCTTCTAGTGCAGCTCGACTAGAACCCTGCAATGGTACTGATCC 2340
                        • S K L F K R V R G S S A A R L E P C N G T D P
S M Q S F T V D Q S Y L N D C G V L V Q L D •

AGACCATGTTAGTAGAGCTTTTGACATCTACAACAAAGATGTTGCCTGTATTGGTAAATTCCTTAAGACGAATTGTTCAAGATTTAGGAA 2430
 D H V S R A F D I Y N K D V A C I G K F L K T N C S R F R N

TTTGGACAAACATGATGCCTACTACATTGTCAAACGTTGTACAAAGACCGTTATGGACCATGAGCAAGTCTGTTATAACGATCTTAAAGA 2520
 L D K H D A Y Y I V K R C T K T V M D H E Q V C Y N D L K D
```

FIG. 12/3

TTCTGGTGCTGTTGCTGAGCATGACTTCTTCACATATAAAGAGGGTAGATGTGAGTTCGGTAATGTTGCACGTAGGAATCTTACAAAGTA 2610
S G A V A E H D F F T Y K E G R C E F G N V A R R N L T K Y

CACAATCATGGATCTTTGTTACGCTATCAGAAATTTTGATGAAAAGAACTGTGAAGTTCTCAAAGAAATACTCGTGACAGTAGGTGCTTG 2700
T H M D L C Y A I R N F D E K N C E V L K E I L V T Y G A C

CACTGAAGAATTCTTTGAAAATAAAGATTGGTTTGATCCAGTTGAAAATGAAGCCATACATGAAGTTTATGCAAAACTTGGACCCATTGT 2790
T E E F F E N K D W F D P V E N E A I H E V Y A K L G P I V

AGCCAATGCTATGCTTAAATGTGTTGCTTTTTGCGATGCGATAGTGGAAAAAGGCTATATAGGTGTTATAACACTTGACAACCAAGATCT 2880
A N A M L K C V A F C D A I V E K G Y I G V I T L D N Q D L

TAATGGCAATTTCTACGATTTCGGCGATTTCGTGAAGACTGCTCCGGGTTTTGGTTGCGCTTGTGTTACATCATATTATTCTTATATGAT 2970
N G N F Y D F G D F V K T A P G F G C A C V T S Y Y S Y M N

GCCTTTAATGGGGATGACTTCATGCTTAGAGTCTGAAAACTTTGTGAAAAGTGACATCTATGGTTCTGATTATAAGCAGTATGATTTACT 3060
P L M G M T S C L E S E N F V K S D I Y G S D Y K Q Y D L L

AGCTTATGATTTTACCGAACATAAGGAGTACCTTTTCCAAAAATACTTTAAGTACTGGGATCGCACATATCACCCAAATTGTTCTGATTG 3150
A Y D F T E H K E Y L F Q K Y F K Y W D R T Y H P N C S D C

TACTAGTGACGAGTGTATTATTCATTGTGCTAATTTTAACACATTGTTTTCTATGACAATACCAATGACAGCTTTTGGACCACTTGTCCG 3240
T S D E C I I H C A N F N T L F S M T I P M T A F G P L V R

TAAAGTTCATATTGATGGTGTACCAGTAGTTGTTACTGCAGGTTACCATTTCAAACAACTTGGTATAGTATGGAATCTTGATGTAAAATT 3330
K V H I D G V P V V V T A G Y H F K Q L G I V W N L D V K L

AGACACAATGAAGTTGAGCATGACTGATCTTCTTAGATTTGTCACAGATCCAACACTTCTTGTAGCATCAAGCCCTGCACTTTTAGACCA 3420
D T M K L S M T D L L R F V T D P T L L V A S S P A L L D Q

FIG. 12/4

```
GCGTACTGTCTGTTTCTCCATTGCAGCTTTGAGTACTGGTATTACATATCAGACAGTAAAACCAGGTCACTTTAACAAGGATTTCTACGA 3510
 R  T  V  C  F  S  I  A  A  L  S  T  G  I  T  Y  Q  T  V  K  P  G  H  F  N  K  D  F  Y  D

TTTCATAACAGAGCGTGGATTCTTTGAAGAGGGATCTGAGTTAACATTAAAACATTTTTTCTTTGCACAGGGTGGTGAAGCTGCTATGAC 3600
 F  I  T  E  R  G  F  F  E  E  G  S  E  L  T  L  K  H  F  F  F  A  Q  G  G  E  A  A  M  T

AGACTTCAATTATTATCGCTACAATAGAGTCACAGTACTTGATATTTGCCAAGCTCAATTTGTTTACAAAATAGTTGGCAAGTATTTTGA 3690
 D  F  N  Y  Y  R  Y  N  R  V  T  V  L  D  I  C  Q  A  Q  F  V  Y  K  I  V  G  K  Y  F  E

ATGTTATGACGGTGGGTGCATTAATGCTCGTGAAGTTGTTGTTACAAACTATGACAAGAGTGCTGGCTATCCTTTGAACAAATTTGGTAA 3780
 C  Y  D  G  G  C  I  N  A  R  E  V  V  V  T  N  Y  D  K  S  A  G  Y  P  L  N  K  F  G  K

AGCTAGACTTTACTACGAAACTCTTTCATATGAAGAGCAGGATGCACTTTTTGCTTTAACAAAGAGAAATGTTTTACCCACAATGACTCA 3870
 A  R  L  Y  Y  E  T  L  S  Y  E  E  Q  D  A  L  F  A  L  T  K  R  N  V  L  P  T  M  T  Q

AATGAATTTGAAATACGCTATTTCTGGTAAGGCAAGAGCTCGTACAGTAGGAGGAGTTTCACTTCTTTCTACCATGACTACGAGACAATA 3960
 M  N  L  K  Y  A  I  S  G  K  A  R  A  R  T  V  G  G  V  S  L  L  S  T  M  T  T  R  Q  Y

TCATCAGAAGCATTTGAAGTCAATTGCTGCAACACGCAATGCTACTGTGGTCATTGGTTCAACCAAGTTTTATGGTGGTTGGGACAATAT 4050
 H  Q  K  H  L  K  S  I  A  A  T  R  N  A  T  V  V  I  G  S  T  K  F  Y  G  G  W  D  N  M

GCTTAAAAATTTAATGCGTGATGTTGATAATGGTTGTTTGATGGGATGGGACTATCCTAAGTGTGACCGTGCTTTACCTAATATGATTAG 4140
 L  K  N  L  M  R  D  V  D  N  G  C  L  M  G  W  D  Y  P  K  C  D  R  A  L  P  N  M  I  R

AATGGCTTCTGCCATGATATTAGGTTCTAAGCATGTTGGTTGTTGTACACATAATGATAGGTTCTACCGCCTCTCCAATGACTTAGCTCA 4230
 M  A  S  A  M  I  L  G  S  K  H  V  G  C  C  T  H  N  D  R  F  Y  R  L  S  N  D  L  A  Q
```

FIG. 12/5

```
AGTACTCACAGAAGTTGTGCATTGCACAGGTGGTTTTTATTTTAAACCTGGTGGTACAACTAGCGGTGATGGTACTACAGCATATGCTAA 4320
 V  L  T  E  V  V  H  C  T  G  G  F  Y  F  K  P  G  G  T  T  S  G  D  G  T  T  A  Y  A  N

CTCTGCTTTTAACATCTTTCAAGCTGTTTCTGCTAATGTTAATAAGCTTTTGGGGGTTGATTCAAACGCTTGTAACAACGTTACAGTAAA 4410
 S  A  F  N  I  F  Q  A  V  S  A  N  V  N  K  L  L  G  V  D  S  N  A  C  N  N  V  T  V  K

ATCCATACAACGTAAAATTTACGATAATTGTTATCGTAGTAGCAGCATTGATGAAGAATTTGTTGTTGAGTACTTTAGTTATTTGAGAAA 4500
 S  I  Q  R  K  I  Y  D  N  C  Y  R  S  S  S  I  D  E  E  F  V  V  E  Y  F  S  Y  L  R  K

ACACTTTTCTATGATGATTTTATCTGATGATGGAGTTGTGTGCTACAACAAAGATTATGCGGATTTAGGTTATGTAGCTGACATTAATGC 4590
 H  F  S  M  M  I  L  S  D  D  G  V  V  C  Y  N  K  D  Y  A  D  L  G  Y  V  A  D  I  N  A
```

POLIMERASA

```
TTTTAAAGCAACACTTTATTACCAGAATAACGTCTTTATGTCCACTTCTAAGTGTTGGGTAGAACCAGATCTTAGTGTTGGACCACATGA 4680
 F  K  A  T  L  Y  Y  Q  N  N  V  F  M  S  T  S  K  C  W  V  E  P  D  L  S  V  G  P  H  E

ATTTTGTTCACAGCATACATTGCAGATTGTTGGGCCTGATGGAGACTACTATCTTCCCTATCCAGACCCGTCCAGAATTTTGTCAGCTGG 4770
 F  C  S  Q  H  T  L  Q  I  V  G  P  D  G  D  Y  Y  L  P  Y  P  D  P  S  R  I  L  S  A  G

TGTGTTTGTTGATGACATAGTTAAAACAGACAATGTTATTATGTTAGAACGTTACGTGTCATTGGCTATTGACGCATACCCGCTCACAAA 4860
 V  F  V  D  D  I  V  K  T  D  N  V  I  M  L  E  R  Y  V  S  L  A  I  D  A  Y  P  L  T  K

ACACCCTAAGCCTGCTTATCAAAAAGTGTTTTACACTCTACTAGATTGGGTTAAACATCTACAGAAAAATTTGAATGCAGGTGTTCTTGA 4950
 H  P  K  P  A  Y  Q  K  V  F  Y  T  L  L  D  W  V  K  H  L  Q  K  N  L  N  A  G  V  L  D

TTCGTTTTCAGTGACAATGTTAGAGCAAGGTCAAGATAAGTTCTGGAGTGAAGAGTTTTACGCTAGCCTCTATGAAAAGTCCACTGTCTT 5040
 S  F  S  V  T  M  L  E  Q  G  Q  D  K  F  W  S  E  E  F  Y  A  S  L  Y  E  K  S  T  V  L
```

DEDOS DE ZINC

```
GCAAGCTGCAGGCATGTGTGTAGTATGTGGTTCGCAAACTGTACTTCGTTGTGGAGACTGTCTTAGGAGACCACTTTTATGCACGAAATG 5130
 Q  A  A  G  M  C  V  V  C  G  S  Q  T  V  L  R  C  G  D  C  L  R  R  P  L  L  C  T  K  C
```

FIG. 12/6

TGCTTACGACCATGTTATGGGAACAAAGCATAAATTCATTATCTCTATCACACCATATGTCTCTACTTTTAATGCTTCTAATCTCAATCA 5220
A Y D H Y N C T K H K F I M S L I P Y Y C S F N G C N V N D

DEDOS DE ZINC

TGTTACAAAGTTGTTTTTAGGTGGTCTTAGTTATTATTGTATGAACCACAAACCACAGTTGTCATTCCCACTCTGTGCTAATGGCAACGT 5310
V T K L F L G G L S Y Y C M N H K P Q L S F P L C A N G N Y

TTTTGGTCTATATAAAAGTAGTGCAGTCGGCTCAGAGGCTGTTGAAGATTTCAACAAACTTGCAGTTTCTGACTGGACTAATGTAGAAGA 5400
F G L Y K S S A V C S E A V E D F N K L A V S D W T N V E D

CTACAAACTTGCTAACAATGTCAAGGAATCTCTGAAAATTTTCGCTGCTGAAACTGTCAAAGCTAAGGAGGAGTCTGTTAAATCTGAATA 5490
Y K L A N N V K E S L K I F A A E T V K A K E E S V K S E Y

TGCTTATGCTGTATTAAAGGAGGTTATCGGCCCTAAGGAAATTGTACTCCAATGGGAAGCTTCTAAGACTAAGCCTCCACTTAACAGAAA 5580
A Y A V L K E V I G P K E I V L Q W E A S K T K P P L N R N

TTCAGTTTTCACGTGTTTTCAGATAAGTAAGGATACTAAAATTCAATTAGGTGAATTTGTGTTTGAGCAATCTGAGTACGGTAGTGATTC 5670
S V F T C F Q I S K D T K I Q L G E F V F E Q S E Y G S D S

TGTTTATTACAAGAGCACGAGTACTTACAAATTGACACCAGGTATGATTTTTGTGTTGACTTCTCATAATGTGAGTCCTCTTAAAGCTCC 5760
V Y Y K S T S T Y K L T P G M I F V L T S H N V S P L K A P

AATTTTAGTCAACCAAGAAAAGTACAATACCATATCTAAGCTCTATCCTGTCTTTAATATAGCCGAGGCCTATAATACACTGGTTCCTTA 5850
I L V N Q E K Y N T I S K L Y P V F N I A E A Y N T L V P Y

CTACCAAATGATAGGTAAGCAAAAATTTACAACTATCCAAGGTCCTCCTGGTAGCGGTAAATCTCATTGTGTTATAGGTTTGGGTTTGTA 5940
Y Q M I G K Q K F T T I Q G P P G S G K S H C V I G L G L Y

HELICASA

FIG. 12/7

TTACCCTCAGGCGAGAATAGTCTACACTGCATGTTCTCATGCGGCTGTAGACGCTTTATGTGAAAAAGCAGCCAAAAACTTCAATGTTGA 6030
Y P Q A R I V Y T A C S H A A V D A L C E K A A K N F N V D

TAGATGTTCAAGGATAATACCTCAAAGAATCAGAGTTGATTGTTACACAGGCTTTAAGCCTAATAACACCAATGCGCAGTACTTGTTTTG 6120
R C S R I I P Q R I R V D C Y T G F K P N N T N A Q Y L F C

TACTGTTAATGCTCTACCAGAAGCAAGTTGTGACATTGTTGTAGTTGATGAGGTCTCTATGTGTACTAATTATGATCTTAGTGTCATAAA 6210
T V N A L P E A S C D I V V V D E V S M C T N Y D L S V I N

TAGCCGACTGAGTTACAAACATATTGTTTATGTTGGAGACCCACAGCAGCTACCAGCTCCTAGAACTTTGATTAATAAGGGTGTACTTCA 6300
S R L S Y K H I V Y V G D P Q Q L P A P R T L I N K G V L Q

ACCGCAGGATTACAATGTTGTAACCAAAAGAATGTGCACACTAGGACCTGATGTCTTTTTGCATAAATGTTACAGGTGCCCAGCTGAAAT 6390
P Q D Y N V V T K R M C T L G P D V F L H K C Y R C P A E I

TGTTAAAACAGTCTCTGCACTTGTTTATGAAAATAAATTTGTACCTGTCAACCCAGAATCAAAGCAGTGCTTCAAAATGTTTGTAAAAGG 6480
V K T V S A L V Y E N K F V P Y N P E S K Q C F K M F V K G

TCAGATTCAGATTGAGTCTAACTCTTCTATAAACAACAAGCAACTAGAGGTTGTCAAGGCCTTTTTAGCACATAATCCAAAATCGCGTAA 6570
Q I Q I E S N S S I N N K Q L E V V K A F L A H N P K V R K

AGCTGTTTTCATCTCACCCTATAATAGTCAAAATTATGTTGCTCGCCGTCTTCTTGGTTTGCAAACGCAAACTGTGGATTCCGCTCAGGG 6660
A V F I S P Y N S Q N Y V A R R L L G L Q T Q T V D S A Q G

TAGTGAGTATGATTACGTCATCTAGCTGCTCTGAAGATTTTTAATCCTGCTGCAATTCACGATGTGGGTAATCCAAAAGGCATCCGTTGT 6750
S E Y D Y V I ·

II ← → III

GCTACAACACCAATACCATGCTTTTGTTATGATCGTGATCCTATTAATAACAATGTTAGATGTCTGGATTATGACTATATGGTACATGGT 6840

FIG. 12/8

CAAATGAATGGTCTTATGTTATTTTGGAACTGTAATGTAGACATGTACCCAGAGTTTTCAATTGTTTCTAGATTTGATACTCGCACTCGC 6930

TCTAAATTGTCTTTAGAAGGTTGTAATGGTGGTGCATTGTATGTTAATAACCATGCTTTCCACACACCAGCTTATGATAGAAGAGCTTTT 7020

GCTAAGCTTAAACCTATGCCATTCTTTTACTATGATGATAGTAATTGTGAACTTGTTGATGGGCAACCTAATTATGTACCACTTAAGTCA 7110

AATGTTTGCATAACAAAATGCAACATTGGTGGTGCTGTCTGCAAGAAGCATGCTGCTCTTTACAGAGCGTATGTTGAGGATTACAACATT 7200

TTTATGCAGGCTGGTTTTACAATATGCTGTCCTCAAAACTTTGACACCTATATGCTTTGGCATGGTTTTGTTAATAGCAAAGCACTTCAG 7290

AGTCTAGAAAATGTGGCTTTTAATGTCGTTAAGAAAGGTGCCTTCACCGGTTTAAAAGGTGACTTACCAACTGCTGTTATTGCTGACAAA 7380

ATAATGGTAAGAGATGGACCTACTGACAAATGTATTTTTACAAATAAGACTAGTTTACCTACAAATGTAGCTTTTGAGTTATATGCAAAA 7470

CGCAAACTTGGACTCACACCTCCATTAACAATACTTAGGAATTTAGGTGTTGTCGCAACATATAAGTTTGTGTTGTGGGATTATGAAGCT 7560

GAACGTCCTTTCTCAAATTTCACTAAGCAAGTGTGTTCCTACACTGATCTTGATAGTGAAGTTGTAACATGTTTTGATAATAGTATTGCT 7650

GGCTCTTTTGAGCGTTTTACTACTACAAGAGATGCAGTGCTTATTTCTAATAACGCTGTGAAAGGGCTTAGTGCCATTAAATTACAATAT 7740

GGCCTTTTGAATGATCTACCTGTAAGTACTGTTGGAAATAAACCTGTCACATGGTATATCTATGTGCGCAAGAATGGTGAGTACGTCGAA 7830

CAAATCGATAGTTACTATACACAGGGACGTACTTTTGAAACCTTCAAACCTCGTAGTACAATGGAAGAAGATTTTCTTAGTATGGATACT 7920

ACACTCTTCATCCAAAAGTATGGTCTTGAGGATTATGGTTTTGAACACGTTGTATTTGGAGATGTCTCTAAAACTACCATTGGTGGTATG 8010

CATCTTCTTATATCGCAAGTGCGCCTTGCAAAAATGGGTTTGTTTTCCGTTCAAGAATTTATGAATAATTCTGACAGTACACTGAAAAGT 8100

TGTTGTATTACATATGCTGATGATCCATCTTCTAAGAATGTGTGCACTTATATGGACATACTCTTGGACGATTTTGTGACTATCATTAAG 8190

AGCTTAGATCTTAATGTTGTGTCCAAACTTGTGGATGTCATTGTAGATTGTAAGGCATGGAGATGGATGTTGTGGTGTGAGAATTCACAT 8280

ATTAAAACCTTCTATCCACAACTCCAATCTGCTGAATGGAATCCCGGCTATAGCATGCCTACACTGTACAAAATCCAGCGTATGTGTCTC 8370

GAACGGTGTAATCTCTACAATTATGGTGCACAAGTGAAATTACCTGATGGCATTACTACTAATGTCGTTAAGTATACTCAGTTGTGTCAA 8460

TACCTTAACACTACTACATTGTGTGTACCACACAAAATGCGTGTATTGCATTTAGGAGCTGCTGGTGCATCTGGTGTTGCTCCTGGTAGT 8550

ACTGTATTAAGAAGATGGTTACCAGATGATGCCATATTGGTTGATAATGATTTGAGAGATTACGTTTCCGACGCAGACTTCAGTGTTACA 8640

FIG. 12/9

GCTGATTGTACTAGTCTTTACATCGAAGACAAGTTTGATTTGCTCGTCTCTGATTTATATGATGGCTCCACAAAATCAATTGACGGTCAA 8730

AACACGTCGAAAGATGGTTTCTTTACTTATATTAATGGTTTCATTAAAGAGAAACTGTCACTTGGTGGATCTGTTGCCATTAAAATCACG 8820

GAATTTAGTTGGAATAAAGATTTATATGAATTGATTCAAAGATTTGAGTATTGGACTGTGTTTTGTACAAGTGTTAACACGTCATCATCA 8910

GAAGGCTTTCTGATTGGTATTAACTACTTAGGACCATACTGTGACAAAGCAATAGTAGATGGAAATATAATGCATGCCAATTATATATTT 9000

TGGAGAAACTCTACAATTATGGCTCTATCACATAACTCAGTCCTAGACACTCCTAAATTCAAGTGTCGTTGTAACAACGCACTTATTGTT 9090

AATTTAAAAGAAAAAGAATTGAATGAAATGGTCATTGGATTACTAAGGAAGGGTAAGTTGCTCATTAGAAATAATGGTAAGTTACTAAAC 9180

TTTGGTAACCACTTCGTTAACACACCATGAAAAAATGCTGTATTTATTACAGTTTTAATCTTACTACTAATTGGTAGACTCCAATTATTA 9270

III IV

M K K C C I Y Y S F N L T T N W •

GAAAGACTATTACTTAATCACTCTTTCAATCTTAAAACTGTCAATGACTTTAATATCTTATATAGGAGTTTAGCAGAAACCAGATTACTA 9360

AAAGTGGTGCTTCGAGTAATCTTTCTAGTCTTACTAGGATTTTGCTGCTACAGATTGTTAGTCACATTAATGTAAGGCAACCCGATGTCT 9450

AAAACTGGTTTTTCCGAGGAATTACTGGTCATCGCGCTGTCTACTCTTGTACAGAATGGTAAGCACGTGTAATAGGAGGTACAAGCAACC 9540

CTATTGCATATTAGGAAGTTTAGATTTGATTTGGCAATGCTAGATTTAGTAATTTAGAGAAGTTTAAAGATCCGCTACGACGAGCCAACA 9630

ATGGAAGAGCTAACGTCTGGATCTAGTGATTGTTTAAAATGTAAAATTGTTTGAAAATTTTCCTTTTGATAGTGATACAAAAAA 9714

FIG. 12/10

A
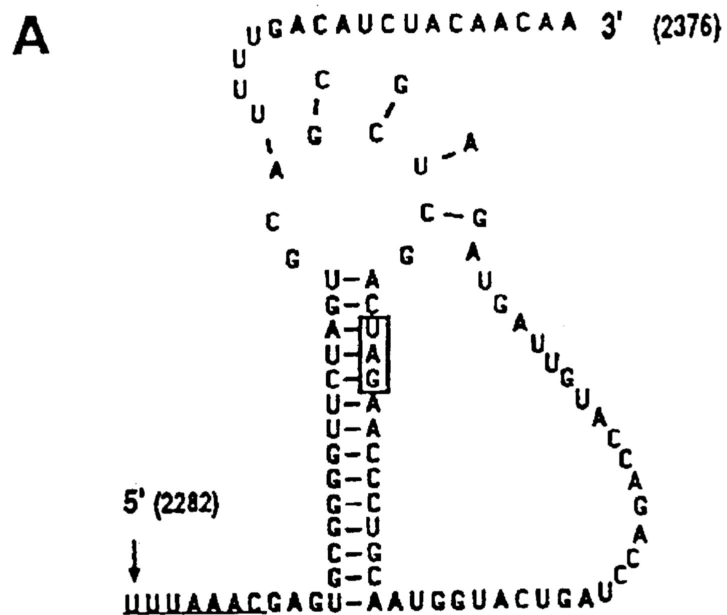
B
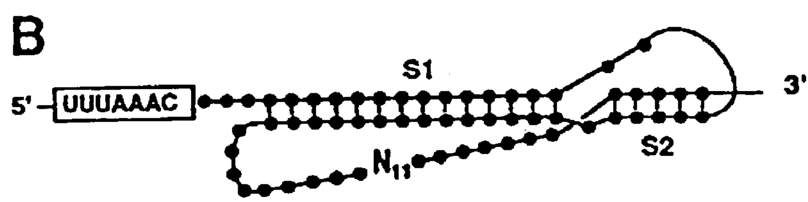
C
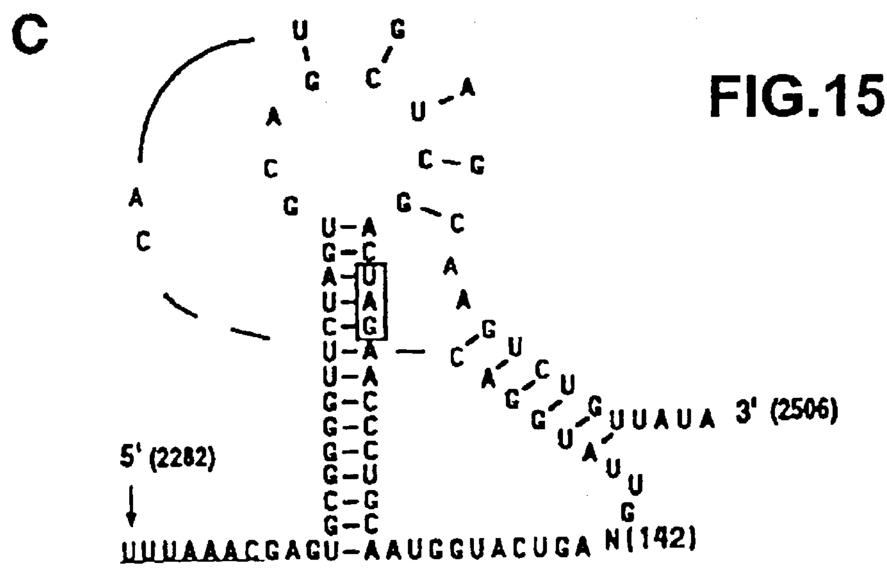
FIG.15
D
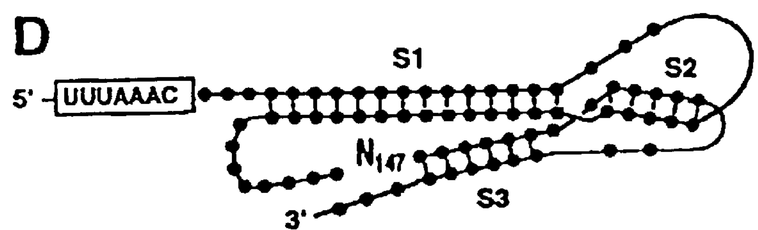

SEQUENCE LISTING

```
<160> NUMBER OF SEQ ID NOS: 32

<210> SEQ ID NO 1
<211> LENGTH: 27
<212> TYPE: DNA
<213> ORGANISM: Transmissible gastroenteritis coronavirus

<400> SEQUENCE: 1

gtgagtgtag cgtggctata tctcttc                                       27


<210> SEQ ID NO 2
<211> LENGTH: 21
<212> TYPE: DNA
<213> ORGANISM: Transmissible gastroenteritis coronavirus

<400> SEQUENCE: 2

ccgttgtggt gtcacattaa c                                             21


<210> SEQ ID NO 3
<211> LENGTH: 32
<212> TYPE: DNA
<213> ORGANISM: Transmissible gastroenteritis coronavirus

<400> SEQUENCE: 3

gcctctagag gagctttgtg gttcacttac ac                                 32
```

-continued

<210> SEQ ID NO 4
<211> LENGTH: 32
<212> TYPE: DNA
<213> ORGANISM: Transmissible gastroenteritis coronavirus

<400> SEQUENCE: 4
gctctagagc gtttgaatca acccccaaaa gc 32

<210> SEQ ID NO 5
<211> LENGTH: 26
<212> TYPE: DNA
<213> ORGANISM: Transmissible gastroenteritis coronavirus

<400> SEQUENCE: 5
ggaattccgg gactatccta agtgtg 26

<210> SEQ ID NO 6
<211> LENGTH: 25
<212> TYPE: DNA
<213> ORGANISM: Transmissible gastroenteritis coronavirus

<400> SEQUENCE: 6
ggaattccag caatactatt atcaa 25

<210> SEQ ID NO 7
<211> LENGTH: 20
<212> TYPE: DNA
<213> ORGANISM: Transmissible gastroenteritis coronavirus

<400> SEQUENCE: 7
ttgataatag tattgctggc 20

<210> SEQ ID NO 8
<211> LENGTH: 23
<212> TYPE: DNA
<213> ORGANISM: Transmissible gastroenteritis coronavirus

<400> SEQUENCE: 8
ggactagtat cactatcaaa agg 23

<210> SEQ ID NO 9
<211> LENGTH: 20
<212> TYPE: DNA
<213> ORGANISM: Transmissible gastroenteritis coronavirus

<400> SEQUENCE: 9
gatggatgtt gtggtgtgag 20

<210> SEQ ID NO 10
<211> LENGTH: 26
<212> TYPE: DNA
<213> ORGANISM: Transmissible gastroenteritis coronavirus

<400> SEQUENCE: 10
cgagttggtg tccgaagaca aaatct 26

<210> SEQ ID NO 11
<211> LENGTH: 20
<212> TYPE: DNA
<213> ORGANISM: Transmissible gastroenteritis coronavirus

<400> SEQUENCE: 11
atacgagcat caatatcacc 20

<210> SEQ ID NO 12
<211> LENGTH: 20
<212> TYPE: DNA
<213> ORGANISM: Transmissible gastroenteritis coronavirus

<400> SEQUENCE: 12
agagttgcca cagactgcag 20

<210> SEQ ID NO 13
<211> LENGTH: 19
<212> TYPE: DNA
<213> ORGANISM: Transmissible gastroenteritis coronavirus

<400> SEQUENCE: 13
cagcagttca aagttaccc 19

<210> SEQ ID NO 14
<211> LENGTH: 20
<212> TYPE: DNA
<213> ORGANISM: Transmissible gastroenteritis coronavirus

<400> SEQUENCE: 14
ccattgttaa gccaacaacc 20

<210> SEQ ID NO 15
<211> LENGTH: 20
<212> TYPE: DNA
<213> ORGANISM: Transmissible gastroenteritis coronavirus

<400> SEQUENCE: 15
atcacactta ggatagtccc 20

<210> SEQ ID NO 16
<211> LENGTH: 19
<212> TYPE: DNA
<213> ORGANISM: Transmissible gastroenteritis coronavirus

<400> SEQUENCE: 16
gtctaacaat gtgccaagg 19

<210> SEQ ID NO 17
<211> LENGTH: 20
<212> TYPE: DNA
<213> ORGANISM: Transmissible gastroenteritis coronavirus

<400> SEQUENCE: 17
gccagcaata ctattatcaa 20

<210> SEQ ID NO 18
<211> LENGTH: 20
<212> TYPE: DNA
<213> ORGANISM: Transmissible gastroenteritis coronavirus

<400> SEQUENCE: 18
cactgtggca cccttacctg 20

<210> SEQ ID NO 19
<211> LENGTH: 20
<212> TYPE: DNA
<213> ORGANISM: Transmissible gastroenteritis coronavirus

<400> SEQUENCE: 19

-continued

```
gtacacccac tatgttgtct                                              20


<210> SEQ ID NO 20
<211> LENGTH: 20
<212> TYPE: DNA
<213> ORGANISM: Transmissible gastroenteritis coronavirus

<400> SEQUENCE: 20

ttgcgagtga aaacaaatgt                                              20


<210> SEQ ID NO 21
<211> LENGTH: 20
<212> TYPE: DNA
<213> ORGANISM: Transmissible gastroenteritis coronavirus

<400> SEQUENCE: 21

ctcacaatca gacgctgtac                                              20


<210> SEQ ID NO 22
<211> LENGTH: 20
<212> TYPE: DNA
<213> ORGANISM: Transmissible gastroenteritis coronavirus

<400> SEQUENCE: 22

gacacgttgt ccctggttgg                                              20


<210> SEQ ID NO 23
<211> LENGTH: 20
<212> TYPE: DNA
<213> ORGANISM: Transmissible gastroenteritis coronavirus

<400> SEQUENCE: 23

acattttaaa caatcactag                                              20


<210> SEQ ID NO 24
<211> LENGTH: 9714
<212> TYPE: DNA
<213> ORGANISM: Transmissible gastroenteritis coronavirus
<220> FEATURE:
<221> NAME/KEY: CDS
<222> LOCATION: (315)..(2315)
<220> FEATURE:
<221> NAME/KEY: modified_base
<222> LOCATION: (1)
<223> OTHER INFORMATION: a, t, c, g, other or unknown

<400> SEQUENCE: 24

nctttttaaag taaagtgagt gtagcgtggc tatatctctt cttttacttt aactagcctt    60

gtgctagatt ttgtcttcgg acaccaactc gaactaaacg aaatatttgt ctttctatga   120

aatcatagag gacaagcgtt gattatttcc attcagtttg gcaatcactc cttggaacgg   180

ggttgagcga acggtgcagt agggttccgt ccctatttcg taagtcgcct agtagtagcg   240

agtgcggttc cgcccgtaca acgttgggta gaccgggttc cgtcctgtga tctccctcgc   300

cggccgccag gaga atg agt tcc aaa caa ttc aag atc ctt gtt aat gag     350
                Met Ser Ser Lys Gln Phe Lys Ile Leu Val Asn Glu
                 1               5                  10

gac tat caa gtc aac gtg cct agt ctt cct att cgt gac gtg tta cag     398
Asp Tyr Gln Val Asn Val Pro Ser Leu Pro Ile Arg Asp Val Leu Gln
        15                  20                  25

gaa att aag tac tgc tac cgt aat gga ttt gag ggc tat gtt ttc gta     446
Glu Ile Lys Tyr Cys Tyr Arg Asn Gly Phe Glu Gly Tyr Val Phe Val
    30                  35                  40
```

-continued

```
cca gaa tac tgt cgt gac cta gtt gat tgc gat cgt aag gat cac tac      494
Pro Glu Tyr Cys Arg Asp Leu Val Asp Cys Asp Arg Lys Asp His Tyr
 45                  50                  55                  60

gtc att ggt gtt ctt ggt aac gga gta agt gat ctt aaa cct gtt ctt      542
Val Ile Gly Val Leu Gly Asn Gly Val Ser Asp Leu Lys Pro Val Leu
                 65                  70                  75

ctt acc gaa ccc tcc gtc atg ttg caa ggc ttt att gtt aga gct aac      590
Leu Thr Glu Pro Ser Val Met Leu Gln Gly Phe Ile Val Arg Ala Asn
             80                  85                  90

tgc aat ggc gtt ctt gag gac ttt gac ctt aaa att gct cgc act gkc      638
Cys Asn Gly Val Leu Glu Asp Phe Asp Leu Lys Ile Ala Arg Thr Xaa
         95                 100                 105

aga ggt gcc ata tat gtt gat caa tac atg tgt ggt gct gat gga aaa      686
Arg Gly Ala Ile Tyr Val Asp Gln Tyr Met Cys Gly Ala Asp Gly Lys
    110                 115                 120

cca gtc att gaa ggc gat ttt aag gac tac ttc ggt gat gaa gac atc      734
Pro Val Ile Glu Gly Asp Phe Lys Asp Tyr Phe Gly Asp Glu Asp Ile
125                 130                 135                 140

att gaa ttt gaa gga gag gag tac cat tgc gct tgg aca act gtg cgc      782
Ile Glu Phe Glu Gly Glu Glu Tyr His Cys Ala Trp Thr Thr Val Arg
                145                 150                 155

gat gag aaa ccg ctg aat cag caa act ctc ttt acc att cag gaa atc      830
Asp Glu Lys Pro Leu Asn Gln Gln Thr Leu Phe Thr Ile Gln Glu Ile
            160                 165                 170

caa tac aat ctg gac att cct cat aaa ttg cca aac tgt gct act aga      878
Gln Tyr Asn Leu Asp Ile Pro His Lys Leu Pro Asn Cys Ala Thr Arg
        175                 180                 185

cat gta gca cca cca gtc aaa aag aac tct aaa ata gtt ctg tct gaa      926
His Val Ala Pro Pro Val Lys Lys Asn Ser Lys Ile Val Leu Ser Glu
    190                 195                 200

gat tac aag aag ctt tat gat atc ttc gga tca ccc ttt atg gga aat      974
Asp Tyr Lys Lys Leu Tyr Asp Ile Phe Gly Ser Pro Phe Met Gly Asn
205                 210                 215                 220

ggt gac tgt ctt agc aaa tgc ttt gac act ctt cat ttt atc gct gct     1022
Gly Asp Cys Leu Ser Lys Cys Phe Asp Thr Leu His Phe Ile Ala Ala
                225                 230                 235

act ctt aga tgc ccg tgt ggt tct gaa agt agc ggc gtt gga gat tgg     1070
Thr Leu Arg Cys Pro Cys Gly Ser Glu Ser Ser Gly Val Gly Asp Trp
            240                 245                 250

act ggt ttt aag act gcc tgt tgt ggt ctt tct ggc aaa gtt aag ggt     1118
Thr Gly Phe Lys Thr Ala Cys Cys Gly Leu Ser Gly Lys Val Lys Gly
        255                 260                 265

gtc act ttg ggt gat att aag cct ggt gat gct gtt gtc act agt atg     1166
Val Thr Leu Gly Asp Ile Lys Pro Gly Asp Ala Val Val Thr Ser Met
    270                 275                 280

agc gca ggt aag gga gtt aag ttc ttt gcc aat tgt gtt ctt caa tat     1214
Ser Ala Gly Lys Gly Val Lys Phe Phe Ala Asn Cys Val Leu Gln Tyr
285                 290                 295                 300

gct ggt gat gtt gaa ggt gtc tcc atc tgg aaa gtt att aaa act ttt     1262
Ala Gly Asp Val Glu Gly Val Ser Ile Trp Lys Val Ile Lys Thr Phe
                305                 310                 315

aca gtt gat gag act gta tgc acc cct ggt ttt gaa ggc gaa ttg aac     1310
Thr Val Asp Glu Thr Val Cys Thr Pro Gly Phe Glu Gly Glu Leu Asn
            320                 325                 330

gac ttc atc aaa cct gag agc aaa tca cta gtt gca tgc agc gtt aaa     1358
Asp Phe Ile Lys Pro Glu Ser Lys Ser Leu Val Ala Cys Ser Val Lys
        335                 340                 345

aga gca ttc att act ggt gat att gat gat gct gta cat gat tgt atc     1406
Arg Ala Phe Ile Thr Gly Asp Ile Asp Asp Ala Val His Asp Cys Ile
    350                 355                 360
```

-continued

```
att aca gga aaa ttg gat ctt agt acc aac ctt ttt ggt aat gtt ggt      1454
Ile Thr Gly Lys Leu Asp Leu Ser Thr Asn Leu Phe Gly Asn Val Gly
365                 370                 375                 380

cta tta ttc aag aag act cca tgg ttt gta caa aag tgt ggt gca ctt      1502
Leu Leu Phe Lys Lys Thr Pro Trp Phe Val Gln Lys Cys Gly Ala Leu
                385                 390                 395

ttt gta gac gct tgg aaa gta gta gag gag ctt tgt ggt tca ctc aca      1550
Phe Val Asp Ala Trp Lys Val Val Glu Glu Leu Cys Gly Ser Leu Thr
            400                 405                 410

ctt aca tac aag caa att tat gaa gtt gta gca tca ctt tgc act tct      1598
Leu Thr Tyr Lys Gln Ile Tyr Glu Val Val Ala Ser Leu Cys Thr Ser
        415                 420                 425

gct ttt acg att gta aac tac aag cca aca ttt gtg gtt cca gac aat      1646
Ala Phe Thr Ile Val Asn Tyr Lys Pro Thr Phe Val Val Pro Asp Asn
    430                 435                 440

cgt gtt aaa gat ctt gta gac aag tgt gtg aaa gtt ctt gta aaa gca      1694
Arg Val Lys Asp Leu Val Asp Lys Cys Val Lys Val Leu Val Lys Ala
445                 450                 455                 460

ttt gat gtt ttt acg cag att atc aca ata gct ggt att gag gcc aaa      1742
Phe Asp Val Phe Thr Gln Ile Ile Thr Ile Ala Gly Ile Glu Ala Lys
                465                 470                 475

tgc ttt gtg ctt ggt gct aaa tac ctg ttg ttc aat aat gca ctt gtc      1790
Cys Phe Val Leu Gly Ala Lys Tyr Leu Leu Phe Asn Asn Ala Leu Val
            480                 485                 490

aaa ctt gtc agt gtt aaa atc ctt ggc aag aag caa aag ggt ctt gaa      1838
Lys Leu Val Ser Val Lys Ile Leu Gly Lys Lys Gln Lys Gly Leu Glu
        495                 500                 505

tgt gca ttc ttt gct act agc ttg gtt ggt gca act gtt aat gtg aca      1886
Cys Ala Phe Phe Ala Thr Ser Leu Val Gly Ala Thr Val Asn Val Thr
    510                 515                 520

cct aaa aga aca gag act gcc act atc agc ttg aac aag gtt gat gat      1934
Pro Lys Arg Thr Glu Thr Ala Thr Ile Ser Leu Asn Lys Val Asp Asp
525                 530                 535                 540

gtt gta gca cca gga gag ggt tat atc gtc att gtt ggt gat atg gct      1982
Val Val Ala Pro Gly Glu Gly Tyr Ile Val Ile Val Gly Asp Met Ala
                545                 550                 555

ttc tac aag agt ggt gaa tat tat ttc atg atg tct agt cct aat ttt      2030
Phe Tyr Lys Ser Gly Glu Tyr Tyr Phe Met Met Ser Ser Pro Asn Phe
            560                 565                 570

gtt ctt act aac aat gtt ttt aaa gca gtt aaa gtt cca tct tat gac      2078
Val Leu Thr Asn Asn Val Phe Lys Ala Val Lys Val Pro Ser Tyr Asp
        575                 580                 585

atc gtt tat gat gtt gat aat gat acc aaa agc aaa atg att gca aaa      2126
Ile Val Tyr Asp Val Asp Asn Asp Thr Lys Ser Lys Met Ile Ala Lys
    590                 595                 600

ctt ggt tca tca ttt gaa caa ata cca act ggc aca caa gat cca att      2174
Leu Gly Ser Ser Phe Glu Gln Ile Pro Thr Gly Thr Gln Asp Pro Ile
605                 610                 615                 620

cgg ttc tgt att gaa aat gaa gtt tgt gtt gtc tgt ggt tgt tgg ctt      2222
Arg Phe Cys Ile Glu Asn Glu Val Cys Val Val Cys Gly Cys Trp Leu
                625                 630                 635

aac aat ggt tgc atg tgc gat cgt act tct atg cag agt ttt act gtt      2270
Asn Asn Gly Cys Met Cys Asp Arg Thr Ser Met Gln Ser Phe Thr Val
            640                 645                 650

gat caa agt tat tta aac gag tgc ggg gtt cta gtg cag ctc gac          2315
Asp Gln Ser Tyr Leu Asn Glu Cys Gly Val Leu Val Gln Leu Asp
        655                 660                 665

tagaaccctg caatggtact gatccagacc atgttagtag agcttttgac atctacaaca    2375
```

-continued

```
aagatgttgc gtgtattggt aaattcctta agacgaattg ttcaagattt aggaatttgg   2435
acaaacatga tgcctactac attgtcaaac gttgtacaaa gaccgttatg gaccatgagc   2495
aagtctgtta taacgatctt aaagattctg gtgctgttgc tgagcatgac ttcttcacat   2555
ataaagaggg tagatgtgag ttcggtaatg ttgcacgtag gaatcttaca aagtacacaa   2615
tgatggatct ttgttacgct atcagaaatt ttgatgaaaa gaactgtgaa gttctcaaag   2675
aaatactcgt gacagtaggt gcttgcactg aagaattctt tgaaaataaa gattggtttg   2735
atccagttga aaatgaagcc atacatgaag tttatgcaaa acttggaccc attgtagcca   2795
atgctatgct taaatgtgtt gctttttgcg atgcgatagt ggaaaaaggc tatataggtg   2855
ttataacact tgacaaccaa gatcttaatg gcaatttcta cgatttcggc gatttcgtga   2915
agactgctcc gggttttggt tgcgcttgtg ttacatcata ttattcttat atgatgcctt   2975
taatggggat gacttcatgc ttagagtctg aaaactttgt gaaaagtgac atctatggtt   3035
ctgattataa gcagtatgat ttactagctt atgattttac cgaacataag gagtaccttt   3095
tccaaaaata ctttaagtac tgggatcgca catatcaccc aaattgttct gattgtacta   3155
gtgacgagtg tattattcat tgtgctaatt ttaacacatt gttttctatg acaataccaa   3215
tgacagcttt tggaccactt gtccgtaaag ttcatattga tggtgtacca gtagttgtta   3275
ctgcaggtta ccatttcaaa caacttggta tagtatggaa tcttgatgta aaattagaca   3335
caatgaagtt gagcatgact gatcttctta gatttgtcac agatccaaca cttcttgtag   3395
catcaagccc tgcactttta gaccagcgta ctgtctgttt ctccattgca gctttgagta   3455
ctggtattac atatcagaca gtaaaaccag gtcactttaa caaggatttc tacgatttca   3515
taacagagcg tggattcttt gaagagggat ctgagttaac attaaaacat tttttctttg   3575
cacagggtgg tgaagctgct atgacagact tcaattatta tcgctacaat agagtcacag   3635
tacttgatat ttgccaagct caatttgttt acaaaatagt tggcaagtat tttgaatgtt   3695
atgacggtgg gtgcattaat gctcgtgaag ttgttgttac aaactatgac aagagtgctg   3755
gctatccttt gaacaaattt ggtaaagcta gactttacta cgaaactctt tcatatgaag   3815
agcaggatgc actttttgct ttaacaaaga gaaatgtttt acccacaatg actcaaatga   3875
atttgaaata cgctatttct ggtaaggcaa gagctcgtac agtaggagga gtttcacttc   3935
tttctaccat gactacgaga caatatcatc agaagcattt gaagtcaatt gctgcaacac   3995
gcaatgctac tgtggtcatt ggttcaacca agttttatgg tggttgggac aatatgctta   4055
aaaatttaat gcgtgatgtt gataatggtt gtttgatggg atgggactat cctaagtgtg   4115
accgtgcttt acctaatatg attagaatgg cttctgccat gatattaggt tctaagcatg   4175
ttggttgttg tacacataat gataggttct accgcctctc caatgagtta gctcaagtac   4235
tcacagaagt tgtgcattgc acaggtggtt tttattttaa acctggtggt acaactagcg   4295
gtgatggtac tacagcatat gctaactctg cttttaacat ctttcaagct gtttctgcta   4355
atgttaataa gcttttgggg gttgattcaa acgcttgtaa caacgttaca gtaaaatcca   4415
tacaacgtaa aatttacgat aattgttatc gtagtagcag cattgatgaa gaatttgttg   4475
ttgagtactt tagttatttg agaaaacact tttctatgat gattttatct gatgatggag   4535
ttgtgtgcta caacaaagat tatgcggatt taggttatgt agctgacatt aatgctttta   4595
aagcaacact ttattaccag aataacgtct ttatgtccac ttctaagtgt tgggtagaac   4655
cagatcttag tgttggacca catgaatttt gttcacagca tacattgcag attgttgggc   4715
ctgatggaga ctactatctt ccctatccag acccgtccag aattttgtca gctggtgtgt   4775
```

-continued

```
ttgttgatga catagttaaa acagacaatg ttattatgtt agaacgttac gtgtcattgg   4835
ctattgacgc atacccgctc acaaaacacc ctaagcctgc ttatcaaaaa gtgttttaca   4895
ctctactaga ttgggttaaa catctacaga aaaatttgaa tgcaggtgtt cttgattcgt   4955
tttcagtgac aatgttagag gaaggtcaag ataagttctg gagtgaagag ttttacgcta   5015
gcctctatga aaagtccact gtcttgcaag ctgcaggcat gtgtgtagta tgtggttcgc   5075
aaactgtact tcgttgtgga gactgtctta ggagaccact tttatgcacg aaatgtgctt   5135
acgaccatgt tatgggaaca aagcataaat tcattatgtc tatcacacca tatgtgtgta   5195
gttttaatgg ttgtaatgtc aatgatgtta caaagttgtt tttaggtggt cttagttatt   5255
attgtatgaa ccacaaacca cagttgtcat tcccactctg tgctaatggc aacgtttttg   5315
gtctatataa aagtagtgca gtcggctcag aggctgttga agatttcaac aaacttgcag   5375
tttctgactg gactaatgta gaagactaca aacttgctaa caatgtcaag gaatctctga   5435
aaattttcgc tgctgaaact gtgaaagcta aggaggagtc tgttaaatct gaatatgctt   5495
atgctgtatt aaaggaggtt atcggcccta aggaaattgt actccaatgg gaagcttcta   5555
agactaagcc tccacttaac agaaattcag ttttcacgtg ttttcagata agtaaggata   5615
ctaaaattca attaggtgaa tttgtgtttg agcaatctga gtacggtagt gattctgttt   5675
attacaagag cacgagtact tacaaattga caccaggtat gatttttgtg ttgacttctc   5735
ataatgtgag tcctcttaaa gctccaattt tagtcaacca agaaaagtac aataccatat   5795
ctaagctcta tcctgtcttt aatatagcgg aggcctataa tacactggtt ccttactacc   5855
aaatgatagg taagcaaaaa tttacaacta tccaaggtcc tcctggtagc ggtaaatctc   5915
attgtgttat aggtttgggt ttgtattacc ctcaggcgag aatagtctac actgcatgtt   5975
ctcatgcggc tgtagacgct ttatgtgaaa aagcagccaa aaacttcaat gttgatagat   6035
gttcaaggat aatacctcaa agaatcagag ttgattgtta cacaggcttt aagcctaata   6095
acaccaatgc gcagtacttg ttttgtactg ttaatgctct accagaagca agttgtgaca   6155
ttgttgtagt tgatgaggtc tctatgtgta ctaattatga tcttagtgtc ataaatagcc   6215
gactgagtta caaacatatt gtttatgttg gagacccaca gcagctacca gctcctagaa   6275
ctttgattaa taagggtgta cttcaaccgc aggattacaa tgttgtaacc aaaagaatgt   6335
gcacactagg acctgatgtc tttttgcata aatgttacag gtgcccagct gaaattgtta   6395
aracagtctc tgcacttgtt tatgaaaata aatttgtacc tgtcaaccca gaatcaaagc   6455
agtgcttcaa aatgtttgta aaaggtcagr ttcagattga gtctaactct tctataaaca   6515
acaagcaact agaggttgtc aaggcctttt tagcacataa tccaaaatgg cgtaaagctg   6575
ttttcatctc accctataat agtcaaaatt atgttgctcg gcgtcttctt ggtttgcaaa   6635
cgcaaactgt ggattccgct cagggtagtg agtatgatta cgtcatctag ctgctctgaa   6695
gatttttaat cctgctgcaa ttcacgatgt gggtaatcca aaaggcatcc gttgtgctac   6755
aacaccaata ccatggtttt gttatgatcg tgatcctatt aataacaatg ttagatgtct   6815
ggattatgac tatatggtac atggtcaaat gaatggtctt atgttatttt ggaactgtaa   6875
tgtagacatg tacccagagt tttcaattgt ttgtagattt gatactcgca ctcgctctaa   6935
attgtcttta gaaggttgta atggtggtgc attgtatgtt aataaccatg ctttccacac   6995
accagcttat gatagaagag cttttgctaa gcttaaacct atgccattct tttactatga   7055
tgatagtaat tgtgaacttg ttgatgggca acctaattat gtaccactta agtcaaatgt   7115
```

-continued

```
ttgcataaca aaatgcaaca ttggtggtgc tgtctgcaag aagcatgctg ctctttacag   7175
agcgtatgtt gaggattaca acatttttat gcaggctggt tttacaatat ggtgtcctca   7235
aaactttgac acctatatgc tttggcatgg ttttgttaat agcaaagcac ttcagagtct   7295
agaaaatgtg gcttttaatg tcgttaagaa aggtgccttc accggtttaa aaggtgactt   7355
accaactgct gttattgctg acaaaataat ggtaagagat ggacctactg acaaatgtat   7415
ttttacaaat aagactagtt tacctacaaa tgtagctttt gagttatatg caaaacgcaa   7475
acttggactc acacctccat taacaatact taggaattta ggtgttgtcg caacatataa   7535
gtttgtgttg tgggattatg aagctgaacg tcctttctca aatttcacta agcaagtgtg   7595
ttcctacact gatcttgata gtgaagttgt aacatgtttt gataatagta ttgctggctc   7655
ttttgagcgt tttactacta caagagatgc agtgcttatt tctaataacg ctgtgaaagg   7715
gcttagtgcc attaaattac aatatggcct tttgaatgat ctacctgtaa gtactgttgg   7775
aaataaacct gtcacatggt atatctatgt gcgcaagaat ggtgagtacg tcgaacaaat   7835
cgatagttac tatacacagg gacgtacttt tgaaaccttc aaacctcgta gtacaatgga   7895
agaagatttt cttagtatgg atactacact cttcatccaa aagtatggtc ttgaggatta   7955
tggttttgaa cacgttgtat ttggagatgt ctctaaaact accattggtg gtatgcatct   8015
tcttatatcg caagtgcgcc ttgcaaaaat gggtttgttt tccgttcaag aatttatgaa   8075
taattctgac agtacactga aaagttgttg tattacatat gctgatgatc catcttctaa   8135
gaatgtgtgc acttatatgg acatactctt ggacgatttt gtgactatca ttaagagctt   8195
agatcttaat gttgtgtcca aagttgtgga tgtcattgta gattgtaagg catggagatg   8255
gatgttgtgg tgtgagaatt cacatattaa aaccttctat ccacaactcc aatctgctga   8315
atggaatccc ggctatagca tgcctacact gtacaaaatc cagcgtatgt gtctcgaacg   8375
gtgtaatctc tacaattatg gtgcacaagt gaaattacct gatggcatta ctactaatgt   8435
cgttaagtat actcagttgt gtcaatacct taacactact acattgtgtg taccacacaa   8495
aatgcgtgta ttgcatttag gagctgctgg tgcatctggt gttgctcctg gtagtactgt   8555
attaagaaga tggttaccag atgatgccat attggttgat aatgatttga gagattacgt   8615
ttccgacgca gacttcagtg ttacaggtga ttgtactagt ctttacatcg aagacaagtt   8675
tgatttgctc gtctctgatt tatatgatgg ctccacaaaa tcaattgacg gtgaaaacac   8735
gtcgaaagat ggtttcttta cttatattaa tggtttcatt aaagagaaac tgtcacttgg   8795
tggatctgtt gccattaaaa tcacggaatt tagttggaat aaagatttat atgaattgat   8855
tcaaagattt gagtattgga ctgtgttttg tacaagtgtt aacacgtcat catcagaagg   8915
ctttctgatt ggtattaact acttaggacc atactgtgac aaagcaatag tagatggaaa   8975
tataatgcat gccaattata tattttggag aaactctaca attatggctc tatcacataa   9035
ctcagtccta gacactccta aattcaagtg tcgttgtaac aacgcactta ttgttaattt   9095
aaaagaaaaa gaattgaatg aaatggtcat tggattacta aggaagggta agttgctcat   9155
tagaaataat ggtaagttac taaactttgg taaccacttc gttaacacac catgaaaaaa   9215
tgctgtattt attacagttt taatcttact actaattggt agactccaat tattagaaag   9275
actattactt aatcactctt tcaatcttaa aactgtcaat gactttaata tcttatatag   9335
gagtttagca gaaaccagat tactaaaagt ggtgcttcga gtaatctttc tagtcttact   9395
aggattttgc tgctacagat tgttagtcac attaatgtaa ggcaacccga tgtctaaaac   9455
tggtttttcc gaggaattac tggtcatcgc gctgtctact cttgtacaga atggtaagca   9515
```

```
cgtgtaatag gaggtacaag caaccctatt gcatattagg aagtttagat ttgatttggc   9575

aatgctagat ttagtaattt agagaagttt aaagatccgc tacgacgagc caacaatgga   9635

agagctaacg tctggatcta gtgattgttt aaaatgtaaa attgtttgaa aattttcctt   9695

ttgatagtga tacaaaaaa                                                9714


<210> SEQ ID NO 25
<211> LENGTH: 667
<212> TYPE: PRT
<213> ORGANISM: Transmissible gastroenteritis coronavirus
<220> FEATURE:
<221> NAME/KEY: MOD_RES
<222> LOCATION: (108)
<223> OTHER INFORMATION: Gly or Val

<400> SEQUENCE: 25

Met Ser Ser Lys Gln Phe Lys Ile Leu Val Asn Glu Asp Tyr Gln Val
  1               5                  10                  15

Asn Val Pro Ser Leu Pro Ile Arg Asp Val Leu Gln Glu Ile Lys Tyr
             20                  25                  30

Cys Tyr Arg Asn Gly Phe Glu Gly Tyr Val Phe Val Pro Glu Tyr Cys
         35                  40                  45

Arg Asp Leu Val Asp Cys Asp Arg Lys Asp His Tyr Val Ile Gly Val
     50                  55                  60

Leu Gly Asn Gly Val Ser Asp Leu Lys Pro Val Leu Leu Thr Glu Pro
 65                  70                  75                  80

Ser Val Met Leu Gln Gly Phe Ile Val Arg Ala Asn Cys Asn Gly Val
                 85                  90                  95

Leu Glu Asp Phe Asp Leu Lys Ile Ala Arg Thr Xaa Arg Gly Ala Ile
            100                 105                 110

Tyr Val Asp Gln Tyr Met Cys Gly Ala Asp Gly Lys Pro Val Ile Glu
        115                 120                 125

Gly Asp Phe Lys Asp Tyr Phe Gly Asp Glu Asp Ile Ile Glu Phe Glu
    130                 135                 140

Gly Glu Glu Tyr His Cys Ala Trp Thr Thr Val Arg Asp Glu Lys Pro
145                 150                 155                 160

Leu Asn Gln Gln Thr Leu Phe Thr Ile Gln Glu Ile Gln Tyr Asn Leu
                165                 170                 175

Asp Ile Pro His Lys Leu Pro Asn Cys Ala Thr Arg His Val Ala Pro
            180                 185                 190

Pro Val Lys Lys Asn Ser Lys Ile Val Leu Ser Glu Asp Tyr Lys Lys
        195                 200                 205

Leu Tyr Asp Ile Phe Gly Ser Pro Phe Met Gly Asn Gly Asp Cys Leu
    210                 215                 220

Ser Lys Cys Phe Asp Thr Leu His Phe Ile Ala Ala Thr Leu Arg Cys
225                 230                 235                 240

Pro Cys Gly Ser Glu Ser Ser Gly Val Gly Asp Trp Thr Gly Phe Lys
                245                 250                 255

Thr Ala Cys Cys Gly Leu Ser Gly Lys Val Lys Gly Val Thr Leu Gly
            260                 265                 270

Asp Ile Lys Pro Gly Asp Ala Val Val Thr Ser Met Ser Ala Gly Lys
        275                 280                 285

Gly Val Lys Phe Phe Ala Asn Cys Val Leu Gln Tyr Ala Gly Asp Val
    290                 295                 300

Glu Gly Val Ser Ile Trp Lys Val Ile Lys Thr Phe Thr Val Asp Glu
```

-continued

```
305                 310                 315                 320

Thr Val Cys Thr Pro Gly Phe Glu Gly Glu Leu Asn Asp Phe Ile Lys
                325                 330                 335

Pro Glu Ser Lys Ser Leu Val Ala Cys Ser Val Lys Arg Ala Phe Ile
            340                 345                 350

Thr Gly Asp Ile Asp Asp Ala Val His Asp Cys Ile Ile Thr Gly Lys
        355                 360                 365

Leu Asp Leu Ser Thr Asn Leu Phe Gly Asn Val Gly Leu Leu Phe Lys
    370                 375                 380

Lys Thr Pro Trp Phe Val Gln Lys Cys Gly Ala Leu Phe Val Asp Ala
385                 390                 395                 400

Trp Lys Val Val Glu Glu Leu Cys Gly Ser Leu Thr Leu Thr Tyr Lys
                405                 410                 415

Gln Ile Tyr Glu Val Val Ala Ser Leu Cys Thr Ser Ala Phe Thr Ile
            420                 425                 430

Val Asn Tyr Lys Pro Thr Phe Val Val Pro Asp Asn Arg Val Lys Asp
        435                 440                 445

Leu Val Asp Lys Cys Val Lys Val Leu Val Lys Ala Phe Asp Val Phe
    450                 455                 460

Thr Gln Ile Ile Thr Ile Ala Gly Ile Glu Ala Lys Cys Phe Val Leu
465                 470                 475                 480

Gly Ala Lys Tyr Leu Leu Phe Asn Asn Ala Leu Val Lys Leu Val Ser
                485                 490                 495

Val Lys Ile Leu Gly Lys Lys Gln Lys Gly Leu Glu Cys Ala Phe Phe
            500                 505                 510

Ala Thr Ser Leu Val Gly Ala Thr Val Asn Val Thr Pro Lys Arg Thr
        515                 520                 525

Glu Thr Ala Thr Ile Ser Leu Asn Lys Val Asp Asp Val Val Ala Pro
    530                 535                 540

Gly Glu Gly Tyr Ile Val Ile Val Gly Asp Met Ala Phe Tyr Lys Ser
545                 550                 555                 560

Gly Glu Tyr Tyr Phe Met Met Ser Ser Pro Asn Phe Val Leu Thr Asn
                565                 570                 575

Asn Val Phe Lys Ala Val Lys Val Pro Ser Tyr Asp Ile Val Tyr Asp
            580                 585                 590

Val Asp Asn Asp Thr Lys Ser Lys Met Ile Ala Lys Leu Gly Ser Ser
        595                 600                 605

Phe Glu Gln Ile Pro Thr Gly Thr Gln Asp Pro Ile Arg Phe Cys Ile
    610                 615                 620

Glu Asn Glu Val Cys Val Val Cys Gly Cys Trp Leu Asn Asn Gly Cys
625                 630                 635                 640

Met Cys Asp Arg Thr Ser Met Gln Ser Phe Thr Val Asp Gln Ser Tyr
                645                 650                 655

Leu Asn Glu Cys Gly Val Leu Val Gln Leu Asp
            660                 665
```

```
<210> SEQ ID NO 26
<211> LENGTH: 1470
<212> TYPE: PRT
<213> ORGANISM: Transmissible gastroenteritis coronavirus
<220> FEATURE:
<221> NAME/KEY: MOD_RES
<222> LOCATION: (1405)
<223> OTHER INFORMATION: Ile or Val

<400> SEQUENCE: 26
```

```
Ser Lys Leu Phe Lys Arg Val Arg Gly Ser Ser Ala Ala Arg Leu Glu
  1               5                  10                  15

Pro Cys Asn Gly Thr Asp Pro Asp His Val Ser Arg Ala Phe Asp Ile
             20                  25                  30

Tyr Asn Lys Asp Val Ala Cys Ile Gly Lys Phe Leu Lys Thr Asn Cys
         35                  40                  45

Ser Arg Phe Arg Asn Leu Asp Lys His Asp Ala Tyr Tyr Ile Val Lys
     50                  55                  60

Arg Cys Thr Lys Thr Val Met Asp His Glu Gln Val Cys Tyr Asn Asp
 65                  70                  75                  80

Leu Lys Asp Ser Gly Ala Val Ala Glu His Asp Phe Phe Thr Tyr Lys
                 85                  90                  95

Glu Gly Arg Cys Glu Phe Gly Asn Val Ala Arg Arg Asn Leu Thr Lys
            100                 105                 110

Tyr Thr Met Met Asp Leu Cys Tyr Ala Ile Arg Asn Phe Asp Glu Lys
        115                 120                 125

Asn Cys Glu Val Leu Lys Glu Ile Leu Val Thr Val Gly Ala Cys Thr
    130                 135                 140

Glu Glu Phe Phe Glu Asn Lys Asp Trp Phe Asp Pro Val Glu Asn Glu
145                 150                 155                 160

Ala Ile His Glu Val Tyr Ala Lys Leu Gly Pro Ile Val Ala Asn Ala
                165                 170                 175

Met Leu Lys Cys Val Ala Phe Cys Asp Ala Ile Val Glu Lys Gly Tyr
            180                 185                 190

Ile Gly Val Ile Thr Leu Asp Asn Gln Asp Leu Asn Gly Asn Phe Tyr
        195                 200                 205

Asp Phe Gly Asp Phe Val Lys Thr Ala Pro Gly Phe Gly Cys Ala Cys
    210                 215                 220

Val Thr Ser Tyr Tyr Ser Tyr Met Met Pro Leu Met Gly Met Thr Ser
225                 230                 235                 240

Cys Leu Glu Ser Glu Asn Phe Val Lys Ser Asp Ile Tyr Gly Ser Asp
                245                 250                 255

Tyr Lys Gln Tyr Asp Leu Leu Ala Tyr Asp Phe Thr Glu His Lys Glu
            260                 265                 270

Tyr Leu Phe Gln Lys Tyr Phe Lys Tyr Trp Asp Arg Thr Tyr His Pro
        275                 280                 285

Asn Cys Ser Asp Cys Thr Ser Asp Glu Cys Ile Ile His Cys Ala Asn
    290                 295                 300

Phe Asn Thr Leu Phe Ser Met Thr Ile Pro Met Thr Ala Phe Gly Pro
305                 310                 315                 320

Leu Val Arg Lys Val His Ile Asp Gly Val Pro Val Val Val Thr Ala
                325                 330                 335

Gly Tyr His Phe Lys Gln Leu Gly Ile Val Trp Asn Leu Asp Val Lys
            340                 345                 350

Leu Asp Thr Met Lys Leu Ser Met Thr Asp Leu Leu Arg Phe Val Thr
        355                 360                 365

Asp Pro Thr Leu Leu Val Ala Ser Ser Pro Ala Leu Leu Asp Gln Arg
    370                 375                 380

Thr Val Cys Phe Ser Ile Ala Ala Leu Ser Thr Gly Ile Thr Tyr Gln
385                 390                 395                 400

Thr Val Lys Pro Gly His Phe Asn Lys Asp Phe Tyr Asp Phe Ile Thr
                405                 410                 415
```

-continued

```
Glu Arg Gly Phe Phe Glu Glu Gly Ser Glu Leu Thr Leu Lys His Phe
            420                 425                 430

Phe Phe Ala Gln Gly Gly Glu Ala Ala Met Thr Asp Phe Asn Tyr Tyr
        435                 440                 445

Arg Tyr Asn Arg Val Thr Val Leu Asp Ile Cys Gln Ala Gln Phe Val
    450                 455                 460

Tyr Lys Ile Val Gly Lys Tyr Phe Glu Cys Tyr Asp Gly Gly Cys Ile
465                 470                 475                 480

Asn Ala Arg Glu Val Val Val Thr Asn Tyr Asp Lys Ser Ala Gly Tyr
                485                 490                 495

Pro Leu Asn Lys Phe Gly Lys Ala Arg Leu Tyr Tyr Glu Thr Leu Ser
            500                 505                 510

Tyr Glu Glu Gln Asp Ala Leu Phe Ala Leu Thr Lys Arg Asn Val Leu
        515                 520                 525

Pro Thr Met Thr Gln Met Asn Leu Lys Tyr Ala Ile Ser Gly Lys Ala
    530                 535                 540

Arg Ala Arg Thr Val Gly Gly Val Ser Leu Leu Ser Thr Met Thr Thr
545                 550                 555                 560

Arg Gln Tyr His Gln Lys His Leu Lys Ser Ile Ala Ala Thr Arg Asn
                565                 570                 575

Ala Thr Val Val Ile Gly Ser Thr Lys Phe Tyr Gly Gly Trp Asp Asn
            580                 585                 590

Met Leu Lys Asn Leu Met Arg Asp Val Asp Asn Gly Cys Leu Met Gly
        595                 600                 605

Trp Asp Tyr Pro Lys Cys Asp Arg Ala Leu Pro Asn Met Ile Arg Met
    610                 615                 620

Ala Ser Ala Met Ile Leu Gly Ser Lys His Val Gly Cys Cys Thr His
625                 630                 635                 640

Asn Asp Arg Phe Tyr Arg Leu Ser Asn Glu Leu Ala Gln Val Leu Thr
                645                 650                 655

Glu Val Val His Cys Thr Gly Gly Phe Tyr Phe Lys Pro Gly Gly Thr
            660                 665                 670

Thr Ser Gly Asp Gly Thr Thr Ala Tyr Ala Asn Ser Ala Phe Asn Ile
        675                 680                 685

Phe Gln Ala Val Ser Ala Asn Val Asn Lys Leu Leu Gly Val Asp Ser
    690                 695                 700

Asn Ala Cys Asn Asn Val Thr Val Lys Ser Ile Gln Arg Lys Ile Tyr
705                 710                 715                 720

Asp Asn Cys Tyr Arg Ser Ser Ser Ile Asp Glu Glu Phe Val Val Glu
                725                 730                 735

Tyr Phe Ser Tyr Leu Arg Lys His Phe Ser Met Met Ile Leu Ser Asp
            740                 745                 750

Asp Gly Val Val Cys Tyr Asn Lys Asp Tyr Ala Asp Leu Gly Tyr Val
        755                 760                 765

Ala Asp Ile Asn Ala Phe Lys Ala Thr Leu Tyr Tyr Gln Asn Asn Val
    770                 775                 780

Phe Met Ser Thr Ser Lys Cys Trp Val Glu Pro Asp Leu Ser Val Gly
785                 790                 795                 800

Pro His Glu Phe Cys Ser Gln His Thr Leu Gln Ile Val Gly Pro Asp
                805                 810                 815

Gly Asp Tyr Tyr Leu Pro Tyr Pro Asp Pro Ser Arg Ile Leu Ser Ala
            820                 825                 830

Gly Val Phe Val Asp Asp Ile Val Lys Thr Asp Asn Val Ile Met Leu
```

-continued

```
        835                 840                 845

Glu Arg Tyr Val Ser Leu Ala Ile Asp Ala Tyr Pro Leu Thr Lys His
    850                 855                 860

Pro Lys Pro Ala Tyr Gln Lys Val Phe Tyr Thr Leu Leu Asp Trp Val
865                 870                 875                 880

Lys His Leu Gln Lys Asn Leu Asn Ala Gly Val Leu Asp Ser Phe Ser
                885                 890                 895

Val Thr Met Leu Glu Glu Gly Gln Asp Lys Phe Trp Ser Glu Glu Phe
            900                 905                 910

Tyr Ala Ser Leu Tyr Glu Lys Ser Thr Val Leu Gln Ala Ala Gly Met
        915                 920                 925

Cys Val Val Cys Gly Ser Gln Thr Val Leu Arg Cys Gly Asp Cys Leu
    930                 935                 940

Arg Arg Pro Leu Leu Cys Thr Lys Cys Ala Tyr Asp His Val Met Gly
945                 950                 955                 960

Thr Lys His Lys Phe Ile Met Ser Ile Thr Pro Tyr Val Cys Ser Phe
                965                 970                 975

Asn Gly Cys Asn Val Asn Asp Val Thr Lys Leu Phe Leu Gly Gly Leu
            980                 985                 990

Ser Tyr Tyr Cys Met Asn His Lys Pro Gln Leu Ser Phe Pro Leu Cys
        995                 1000                1005

Ala Asn Gly Asn Val Phe Gly Leu Tyr Lys Ser Ser Ala Val Gly Ser
   1010                1015                1020

Glu Ala Val Glu Asp Phe Asn Lys Leu Ala Val Ser Asp Trp Thr Asn
1025                1030                1035                1040

Val Glu Asp Tyr Lys Leu Ala Asn Asn Val Lys Glu Ser Leu Lys Ile
               1045                1050                1055

Phe Ala Ala Glu Thr Val Lys Ala Lys Glu Glu Ser Val Lys Ser Glu
           1060                1065                1070

Tyr Ala Tyr Ala Val Leu Lys Glu Val Ile Gly Pro Lys Glu Ile Val
       1075                1080                1085

Leu Gln Trp Glu Ala Ser Lys Thr Lys Pro Pro Leu Asn Arg Asn Ser
   1090                1095                1100

Val Phe Thr Cys Phe Gln Ile Ser Lys Asp Thr Lys Ile Gln Leu Gly
1105                1110                1115                1120

Glu Phe Val Phe Glu Gln Ser Glu Tyr Gly Ser Asp Ser Val Tyr Tyr
               1125                1130                1135

Lys Ser Thr Ser Thr Tyr Lys Leu Thr Pro Gly Met Ile Phe Val Leu
           1140                1145                1150

Thr Ser His Asn Val Ser Pro Leu Lys Ala Pro Ile Leu Val Asn Gln
       1155                1160                1165

Glu Lys Tyr Asn Thr Ile Ser Lys Leu Tyr Pro Val Phe Asn Ile Ala
   1170                1175                1180

Glu Ala Tyr Asn Thr Leu Val Pro Tyr Tyr Gln Met Ile Gly Lys Gln
1185                1190                1195                1200

Lys Phe Thr Thr Ile Gln Gly Pro Pro Gly Ser Gly Lys Ser His Cys
               1205                1210                1215

Val Ile Gly Leu Gly Leu Tyr Tyr Pro Gln Ala Arg Ile Val Tyr Thr
           1220                1225                1230

Ala Cys Ser His Ala Ala Val Asp Ala Leu Cys Glu Lys Ala Ala Lys
       1235                1240                1245

Asn Phe Asn Val Asp Arg Cys Ser Arg Ile Ile Pro Gln Arg Ile Arg
   1250                1255                1260
```

```
Val Asp Cys Tyr Thr Gly Phe Lys Pro Asn Asn Thr Asn Ala Gln Tyr
1265                1270                1275                1280

Leu Phe Cys Thr Val Asn Ala Leu Pro Glu Ala Ser Cys Asp Ile Val
                1285                1290                1295

Val Val Asp Glu Val Ser Met Cys Thr Asn Tyr Asp Leu Ser Val Ile
            1300                1305                1310

Asn Ser Arg Leu Ser Tyr Lys His Ile Val Tyr Val Gly Asp Pro Gln
        1315                1320                1325

Gln Leu Pro Ala Pro Arg Thr Leu Ile Asn Lys Gly Val Leu Gln Pro
    1330                1335                1340

Gln Asp Tyr Asn Val Val Thr Lys Arg Met Cys Thr Leu Gly Pro Asp
1345                1350                1355                1360

Val Phe Leu His Lys Cys Tyr Arg Cys Pro Ala Glu Ile Val Lys Thr
                1365                1370                1375

Val Ser Ala Leu Val Tyr Glu Asn Lys Phe Val Pro Val Asn Pro Glu
            1380                1385                1390

Ser Lys Gln Cys Phe Lys Met Phe Val Lys Gly Gln Xaa Gln Ile Glu
        1395                1400                1405

Ser Asn Ser Ser Ile Asn Asn Lys Gln Leu Glu Val Val Lys Ala Phe
    1410                1415                1420

Leu Ala His Asn Pro Lys Trp Arg Lys Ala Val Phe Ile Ser Pro Tyr
1425                1430                1435                1440

Asn Ser Gln Asn Tyr Val Ala Arg Arg Leu Leu Gly Leu Gln Thr Gln
                1445                1450                1455

Thr Val Asp Ser Ala Gln Gly Ser Glu Tyr Asp Tyr Val Ile
            1460                1465                1470


<210> SEQ ID NO 27
<211> LENGTH: 16
<212> TYPE: PRT
<213> ORGANISM: Transmissible gastroenteritis coronavirus

<400> SEQUENCE: 27

Met Lys Lys Cys Cys Ile Tyr Tyr Ser Phe Asn Leu Thr Thr Asn Trp
  1               5                  10                  15


<210> SEQ ID NO 28
<211> LENGTH: 95
<212> TYPE: RNA
<213> ORGANISM: Transmissible gastroenteritis coronavirus

<400> SEQUENCE: 28

uuuaaacgag ugcgggguuc uagugcagcu cgacuagaac ccugcaaugg uacugaucca      60

gaccauguua guagagcuuu ugacaucuac aacaa                                 95


<210> SEQ ID NO 29
<211> LENGTH: 207
<212> TYPE: RNA
<213> ORGANISM: Transmissible gastroenteritis coronavirus
<220> FEATURE:
<221> NAME/KEY: modified_base
<222> LOCATION: (57)..(198)
<223> OTHER INFORMATION: a, u, c, g, other or unknown

<400> SEQUENCE: 29

uuuaaacgag ugcgggguuc uagugcagcu cgacuagaac ccugcaaugg uacugannnn      60

nnnnnnnnnn nnnnnnnnnn nnnnnnnnnn nnnnnnnnnn nnnnnnnnnn nnnnnnnnnn     120
```

-continued

```
nnnnnnnnnn nnnnnnnnnn nnnnnnnnnn nnnnnnnnnn nnnnnnnnnn nnnnnnnnnn    180

nnnnnnnnnn nnnnnnnngu uauggac                                        207


<210> SEQ ID NO 30
<211> LENGTH: 19
<212> TYPE: RNA
<213> ORGANISM: Transmissible gastroenteritis coronavirus

<400> SEQUENCE: 30

caugagcaag ucuguuaua                                                  19


<210> SEQ ID NO 31
<211> LENGTH: 20
<212> TYPE: DNA
<213> ORGANISM: Transmissible gastroenteritis coronavirus

<400> SEQUENCE: 31

taatacgact cactataggg                                                 20


<210> SEQ ID NO 32
<211> LENGTH: 19
<212> TYPE: DNA
<213> ORGANISM: Transmissible gastroenteritis coronavirus

<400> SEQUENCE: 32

aaaaaaaggg tcggcatgg                                                  19
```

VECTORS BASED ON RECOMBINANT DEFECTIVE VIRAL GENOMES, AND THEIR USE IN THE FORMULATION OF VACCINES

The vectors comprise a recombinant defective viral genome expressing at least one antigen suitable for the induction of systemic and secretory immune responses. The defective viral genome comprises the parental virus genome having viral replicase recognition signals located on ends 3' and 5' further comprising internal deletions, and wherein said defective viral genome depends on a helper virus for its replication. These vectors are suitable for the forming of a recombinant system comprising (a) the aforesaid expression vector, and (b) a helper virus which supplies functional and structural proteins for the replication and encapsidation of the defective genome. This system is suitable for the manufacture of mono- and polyvalent vaccines against infectious agents of various animal species, especially pigs, dogs and cats.

FIELD OF THE INVENTION

This invention relates to a number of vectors based on recombinant defective virus genomes expressing antigens suitable for the induction of systemic and secretory immune responses for the prevention of infections in the mucosae, and to their use with vaccinal purposes together with a suitable helper virus.

BACKGROUND OF THE INVENTION

The attainment of recombinant proteins using expression vectors is a well-known fact in general, prokaryotic and yeast expression systems are highly efficacious and easy to use, whereas the expression systems used containing superior eukaryotic cells present a number of drawbacks relative to low protein production levels and limitations in the host range. Of the existing expression systems for superior eukaryotic cells, baculovirus-based vectors are the most efficacious in terms of protein production. However, they can only be used in insect cells that, as is known, glycosilate proteins differently from the way animal cells do. In addition, the construction of the recombinant virus takes place through a homologous recombination, which is a laborious technique, especially when numerous genetic variants have to be analyzed.

On the other hand, vectors based on DNA viruses suitable for heterologous gene expression are known. However, the use of DNA-based vectors presents numerous drawbacks for, as they replicate in the nucleus of the host cell and can become integrated in the genome, they are therefore not reliable. On the contrary, the use of RNA-based vectors overcomes the drawbacks associated with the use of DNA viruses because, since they replicate not in the genome of the host cell but in the cytoplasm, replication takes place via RNA and not via DNA, and the possibilities of integration in the genome are very low, making the vectors based on these RNA viruses more reliable.

Also well-known are defective interfering particles (DI) containing the virion capsid and a defective genome, which are deletion subgenomic mutants mostly generated form infectious viral genomes by a replication error. In general, the term "DI particle" refers to defective viruses lacking a region of the RNA or DNA genome, containing the proteins and antigens of the virus, requiring co-infection of the infectious parental virus (helper virus) for replication and which specifically interfere with the homologous helper virus, as they replicate at its expense [Huang and Baltimore, Nature, 226, 325–327 (1970)]. DI genomes arise from genome reorganizations as a result of shifts of the RNA polymerase from one RNA template to another or from one segment of an RNA template to another segment of the same molecule. These DI genomes, once they have been generated, self amplify at the expense of the parental genome or the amplifying virus coding for the proteins involved in replication and encapsidation and which has to compete with defective genomes for such products.

DI particles have been obtained and characterized from some coronaviruses, such as the murine hepatitis virus (MHV), infectious bronchitis virus (IBV), and bovine coronavirus (BCV), although DI particles derived from porcine transmissible gastroenteritis virus (TGEV) have not been described. One of the MHV natural DI particles has been used as the basis for the development of an expression vector in which the exogenous gene is inserted under the control of an internal promoter transcription sequence [Lin and Lai, J. Virol., 6110–6118, October. (1993)].

Generally, known heterologous gene expression vectors based on DI particles have some drawbacks related with their species and target organ specificity and their limited capacity for cloning, that limit their possibilities of use, both in basic research and in research applied to the development of such vectors for therapeutical purposes, including vaccines.

Consequently, there is still need of heterologous gene expression vectors that may successfully overcome the mentioned drawbacks. Specifically, it would be highly advantageous to have available some heterologous gene expression vectors with a high level of safety and cloning capacity and which could be designed so that their species specificity and tropism might be easily controlled.

The present invention provides a solution to the existing problem, comprising a vector based on a recombinant defective viral genome expressing antigens suitable for the induction of an immune response and for the prevention of infections caused by different infectious agents in various animal species. The heterologous gene expression vectors (or DNA sequences) provided by this invention have a high level of safety, as well as high cloning capacity, and may be designed so that their species specificity and tropism may easily be controlled, making such vectors suitable for the formulation of vaccines capable of conferring protection against infections caused by the different infectious agents in various animal species.

Therefore, an object of the present invention is a vector based on a recombinant defective viral genome expressing at least one antigen suitable for the induction of immune response—specifically, a systemic and secretory immune response against infectious agents in various animal species—, or an antibody providing protection against an infectious agent provided with a high level of safety and cloning capacity, and which may be designed so that its species specificity and tropism may be easily controlled.

The defective viral genome which serves as a basis for the construction of the said vector is also an additional objective of this invention.

Another additional object of this invention is a recombinant expression system of heterologous proteins comprising (a) the vector described above and (b) a helper virus that will provide the proteins involved in the replication and encapsidation of the recombinant defective viral genome.

Another additional objective of this invention is vaccines capable of inducing protection against infections caused by different infectious agents in various animal species, comprising the recombinant system described above, together with a pharmaceutically acceptable excipient. These vectors can be uni-, or multivalent, depending on whether the expression vectors present in the recombinant system express one, or more antigens capable of inducing an immune response against one, or more infectious agents, or one or more antibodies providing protection against one or more infectious agents.

Other objects provided by this invention comprise a method for the immunization of animals, consisting of the administration of the said recombinant system or vaccine, as well as a method for the protection of newborn animals from infectious agents that infect the mentioned species.

BRIEF DESCRIPTION OF THE FIGURES

FIGS. 8A and 8B: evolution of the virus titer with the number of the passage in IPEC and PM, respectively. FIG. 8C: analysis of the RNA of ST cells infected with virus from passages 1 and 10 in IPEC (by metabolic labeling with $32P_i$), or of passages 1 and 5 in PM cells (by hybridization with one oligonucleotide complementary to the leading RNA).

FIG. 9 shows the encapsidation of defective genomes A, B and C. FIG. 9A shows an agarose gel stained with ethidium bromide, in which the RNA extracted from purified virions of passage 1 and passage 41 are analyzed by means of centrifugation through a 15% sucrose cushion (w/v). In the lane of passage 41, RNAs A, B and C can be observed, as well as the parental genome. The bars on the left indicate mobility markers in kb. FIG. 9B shows the results of the analysis of the RNA of passage 41 virions purified by centrifugation through sucrose cushions or continuous gradient, by Northern-blot assay with an oligonucleotide complementary to the leader RNA. Commercial GibcoBRL RNAs and RNA from passage 1 virions (lane a) were used as markers. Lanes b and c, RNA extracted from virions sedimented through 31% and 15% sucrose cushions (w/v), respectively. Lanes d and e, RNA extracted from virus purified through a continuous sucrose cushion, fractions of 1.20 and 1.15 g/ml density, respectively.

RNAs B+C, RNAs B and C: purified bands in an experiment where the RNAs of THER-1 STp41 virus were fractionated in gel. RNAs B and C migrate very close, and where cut as a single band.

FIG. 12 (SEQ ID NOS: 24–27) shows the complete RNA DI-C cDNA sequence (See SEQ ID NO: 24) obtained by the sequencing of overlapping fragments of the a, b, c, and d cloning. RNA DI-C has kept four discontinuous parental genome regions: I, II, III and IV. The flanking sites of these regions are indicated with arrows. The translation of the three ORFs present in genome DI-C is indicated: chimeric ORF of 6.7 kb resulting from the fusion of discontinuous regions I and II in phase; the mini-ORF of three amino acids preceding it in phase; and the ORF, which initiates at the AUG of gene S. Highly homologous regions—with the proteic domains described for other coronaviruses as those responsible for the polymerase and helicase activities, and metal ion binding sites—appear shaded. CTAAAC transcription promoter sequences appear shaded. The overlapping area between ORFs 1a and 1b (41 nucleotides) appears shaded, the slippery sequence of the ribosome is underlined, and the ORF1a termination codon is in a box. In positions 637, 6397, and 6485, the specific changes with respect to the parental genome are indicated. The nucleotides present in the parental genome in these positions are indicated.

Figure 13:
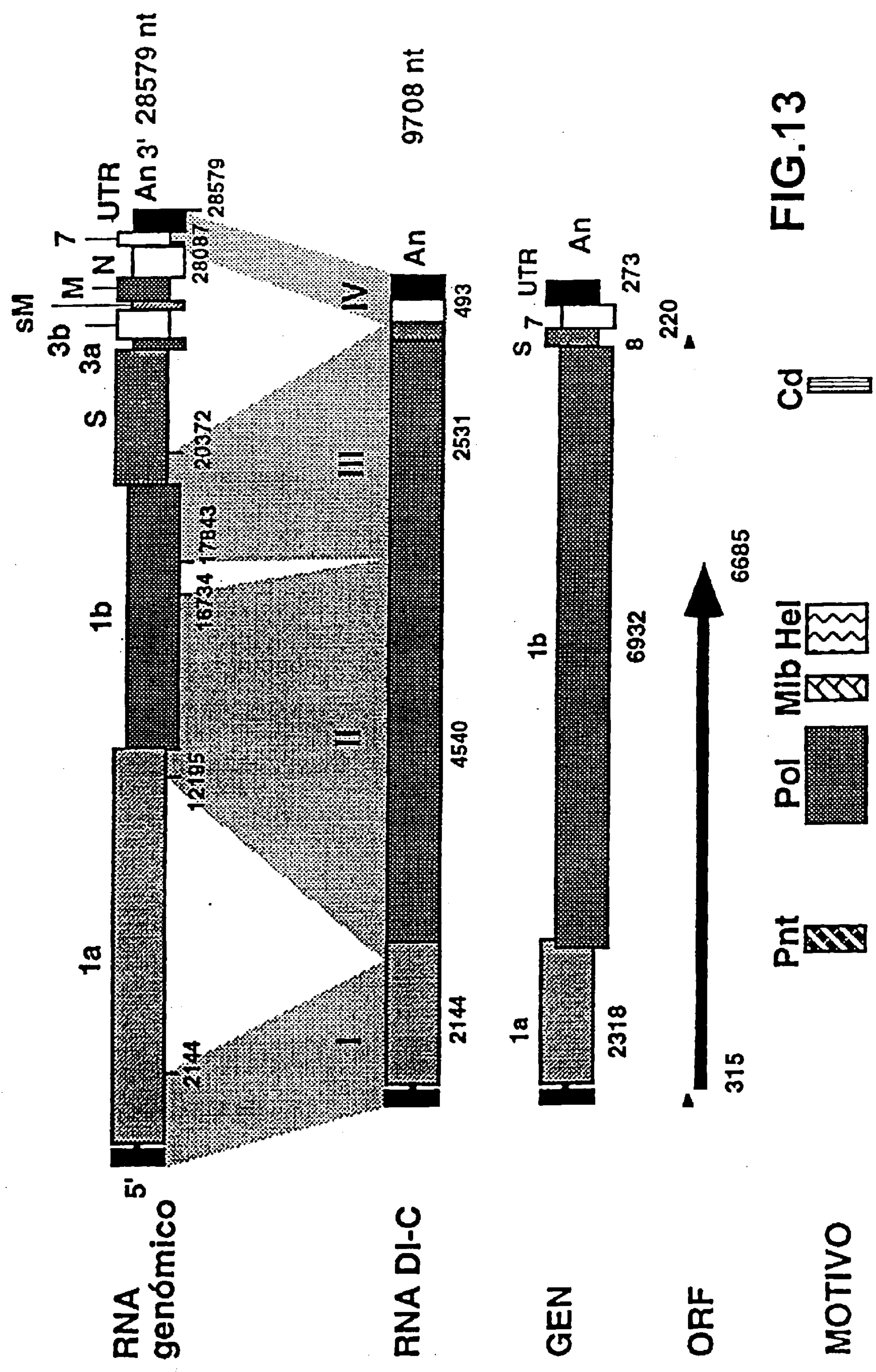

FIG. 13 shows a diagram of the RNA DI-C structure. Total genomic length appears to the right of the boxes. RNA DI-C contains four discontinuous TGEV genome regions (I, II, III and IV). These regions comprise 2.1 kb of the 5' end of the genome, almost complete ORF1b including the overlapping area between ORFs 1a and 1b, the initiation of gene S, incomplete ORF7 and untranslated region 3'. The letters and numbers above the parental genome box indicate viral genes. The numbers below the box indicate the position of the flanking nucleotides of the discontinuous regions in the parental genome, taking as reference the sequence of the TGEV PUR46-PAR isolate. In the box corresponding to RNA DI-C, the length of the four discontinuous regions is indicated in nucleotides. In the third box it is indicated the number of nucleotides derived from each viral gene, taking into account that ORFs 1a and 1b overlap with each other 43 nucleotides in the parental genome. The ORFs predicted in the computer analysis are indicated with arrows or arrowheads. Pnt, pseudoknot; Pol, polymerase; Mib, metal ion binding; Hel, helicase; Cd, conserved domain.

Figure 14:
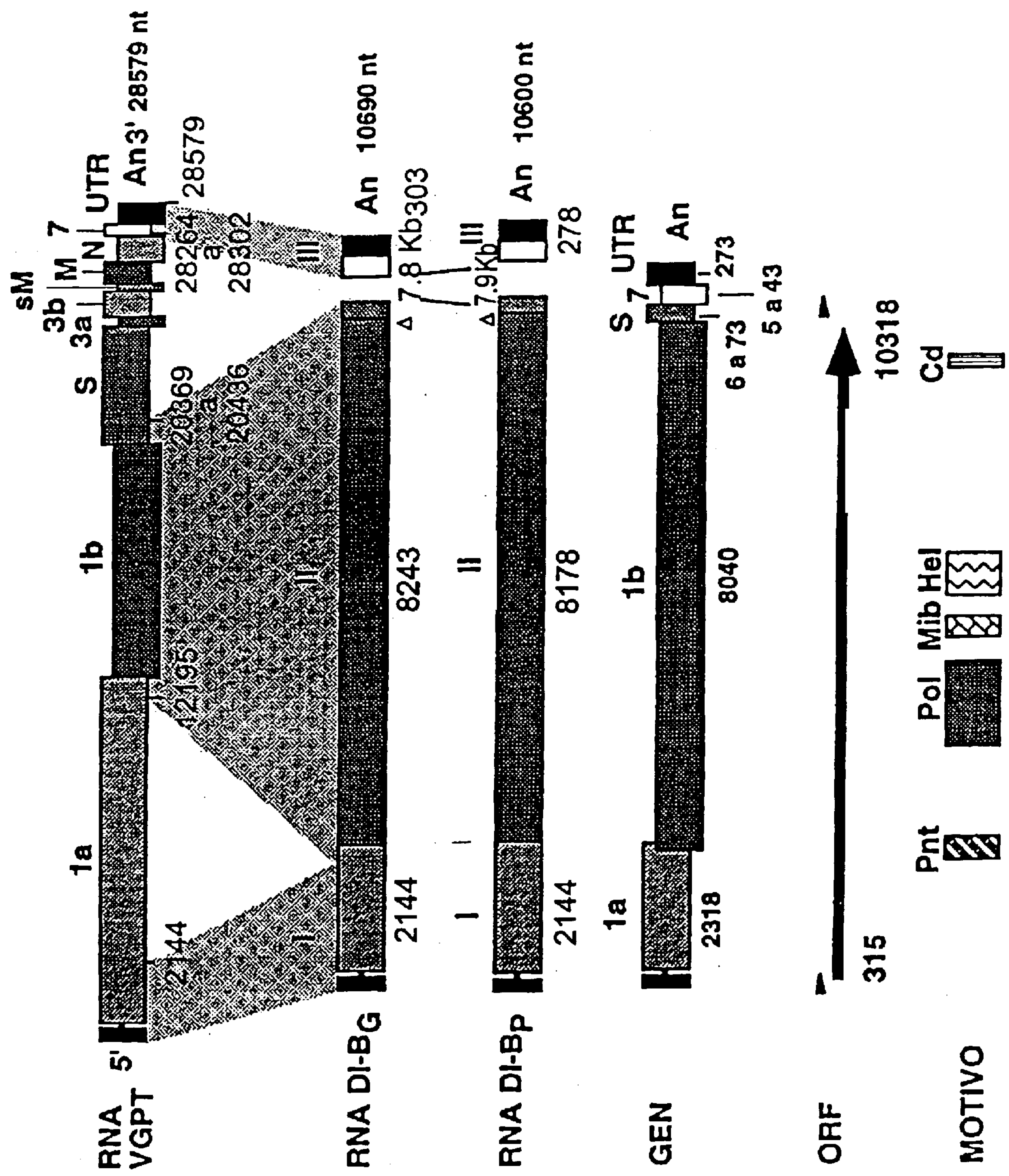

FIG. 14 shows the structure of the RNA DI-B. RNA DI-B contains three discontinuous regions (I, II and III) of the TGEV genome, comprising, 2.1 kb of the 5' end of the genome, complete ORF1b including the overlapping area between ORFs 1a and o 1b, the initiation of gene S, the termination of ORF7, and the untranslated region of 3' end. Letters and numbers over the parental genome box indicate viral genes. The numbers underneath the box indicate the position in the parental genome of the flanking nucleotides of the discontinuous regions, taking as reference the sequence of the TGEV PUR46-PAR isolate. Size heterogeneity of the deletion occurring between discontinuous regions II and III is responsible for the actual existence of a DI-B genome population. In the second and third boxes are indicated the length in nucleotides of the three discontinuous regions for the largest and smallest sized genomes, respectively. In the third box it is indicated the number of nucleotides derived from each viral gene, taking into account that ORFs 1a and 1b overlap each other for 43 nucleotides in the parental genome. The ORFs predicted by the computer analysis are indicated with arrows or arrowheads. Pnt, pseudoknot; Pol, polymerase; Mib, metal ion binding; Hel, helicase; Cd, conserved domain.

FIG. 15 shows the secondary and tertiary RNA structures in the overlapping zone between ORFs 1a and 1b in the RNA DI-C. (A) (SEQ ID NO: 28) Structure predicted when considering the region closest to the fork-like structure presenting complementarity to the nucleotides of the knot thus constituting the pseudoknot (nucleotides 2354 to 2358). The slippery sequence UUUAAAC is underlined. ORF1a termination codon is indicated in the box. (B) Schematic representation of this pseudoknot, which involves two sequence complementarity sections (stems: S1 and S2). The slippery sequence is represented in a box. (C) (SEQ ID NO: 29 and SEQ ID NO: 30) An alternative model taking into account the sequence of nucleotide 2489 to 2493 in the folding of the pseudoknot. This structure contains an additional complementarity sequence (stem) section. (D) Schematic representation of the pseudoknot, in which the three stems are marked: S1, S2 and S3.

Figure 16:
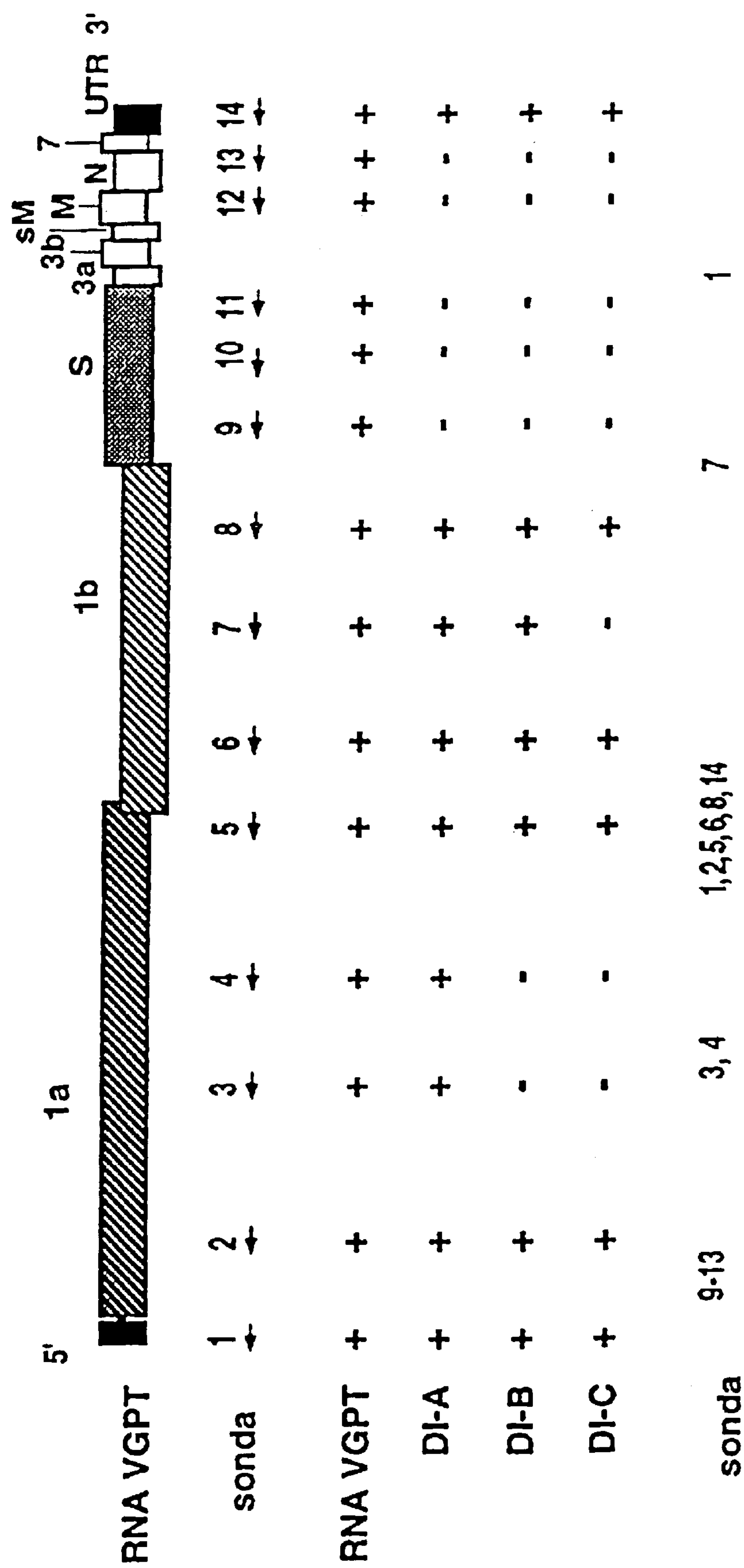

FIG. 16 shows the mapping of RNAs DI by hybridization with oligonucleotides specific to the virus in Northern-blot assays. The RNA of THER-1-STp41 virus was fractionated in agarose gels until a clear separation of the parental genome RNAs and DI A, B and C was obtained. The RNA was transferred to nylon filters which were hybridized with several oligonucleotides labeled with $^{32}P_i$, hybridized with the parental genome (+), and hybridized (+) or not (−) with the defective genomes. The approximate localization of the sequences complementary to the oligonucleotides in the parental genome is indicated by arrows. Their exact sequence and position are indicated in Table 3. All the oligonucleotides hybridized with the parental genome and gave the expected results with RNAs B and C.

Figure 17:
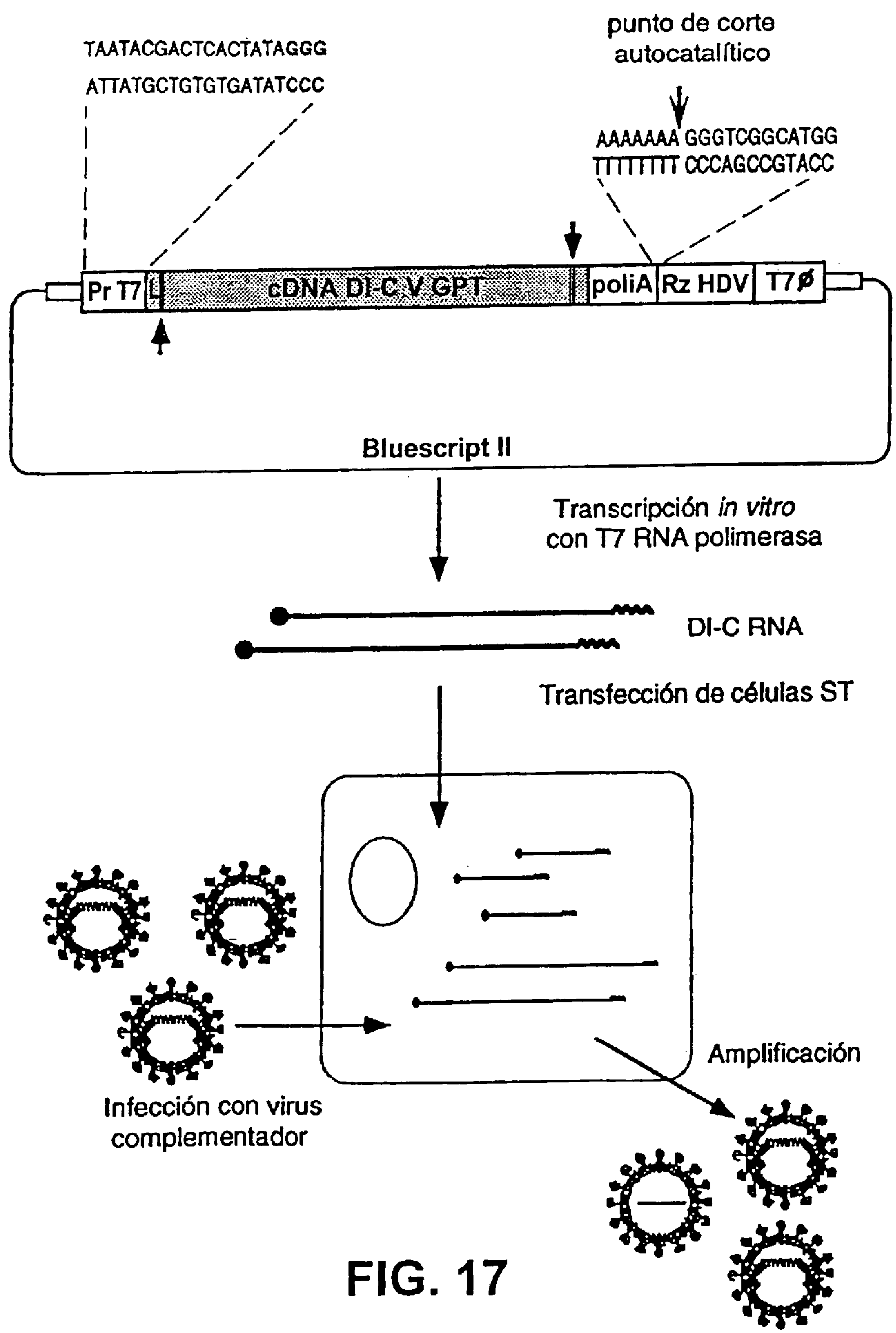

FIG. 17 shows an outline of the method for the obtainment of vaccinal viruses by transfection of infected cells with RNA DI-C. A prototype outline is illustrated with the construction that enabled the production of DI-C RNA by in vitro transcription, maintaining the 5' and 3' ends present in the original defective particle. The sequence of the T7 promoter [PrT7] (SEQ ID NO: 31) and the sequence of the autocatalytic ribozyme of the hepatitis delta virus (HDV) [Rz HDV] (SEQ ID NO: 32) were cloned flanking the DI-C RNA sequence. The position of the autocatalytic cleavage introduced by the ribozyme is marked above the sequence. The arrows indicate the positions of the internal transcription promoter sequences maintained in a natural form in the RNA DI-C. L: leader. T7ϕ: T7 bacteriophage transcription termination signals. Virions encapsidating both the helper virus as well as the defective genomes in which the heterologous genes had been cloned were recovered, when the in vitro transcribed RNAs were transfected into ST cells infected with the corresponding helper virus.

Figure 18:
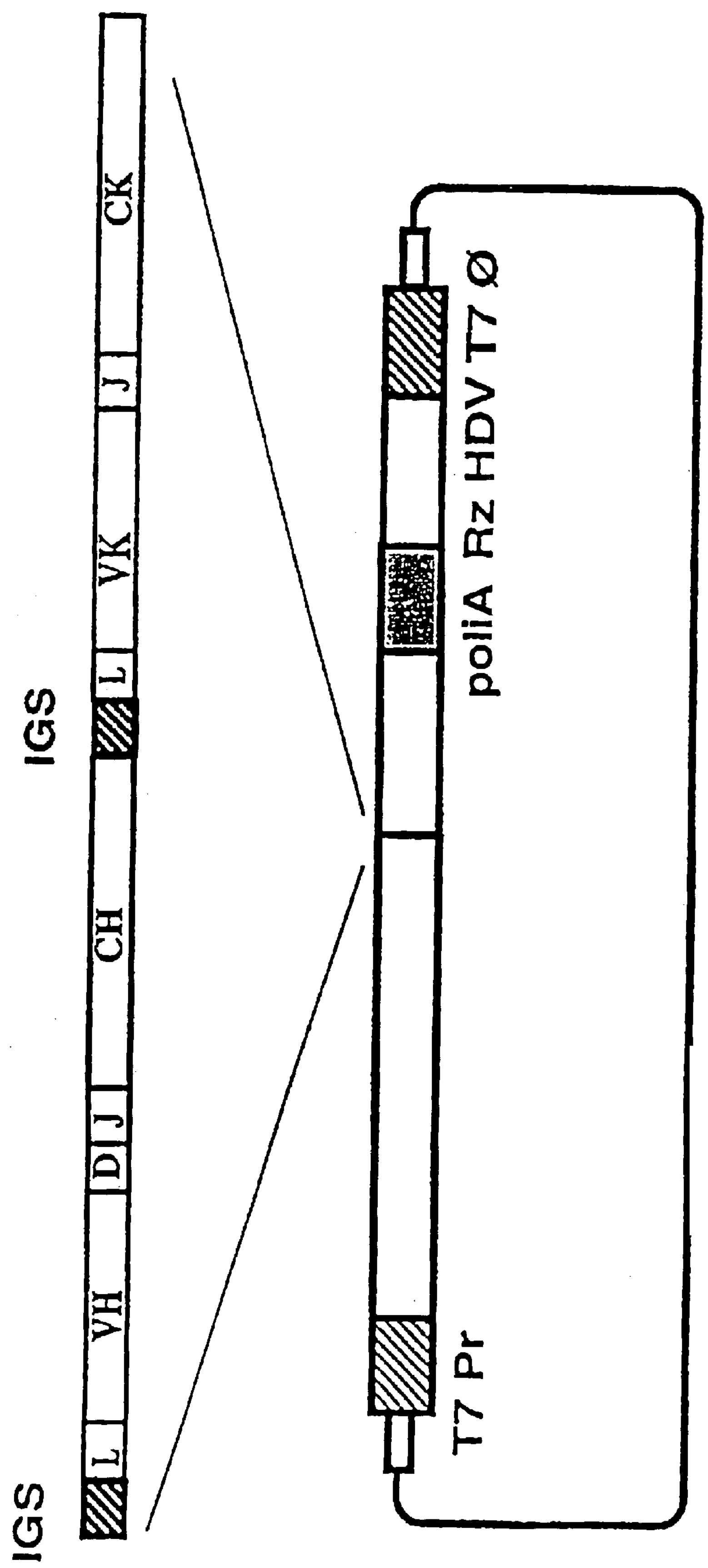

FIG. 18 shows a prototype outline of the construction that enabled the production of pDIA-6A.C3 by in vitro transcription, maintaining the 3' and 5' ends present in the original defective particle. The sequence of the bacteriophage T7 promoter [PrT7] and the presence of the autocatalytic ribozyme of the hepatitis delta virus (HDV) [RzHDV] were cloned flanking the cDNA sequence coding for an autoreplicative RNA. Plasmid pDIA-6A.C3 contains the gene coding for monoclonal antibody 6A.C3 which neutralizes TGEV [see Example 4]. The cloning of the heterologous gene was done after ORF1b, following the S gene initiation codon (AUG), and in reading phase with this gene (IGS: intergenic sequence; L leader sequence; D: diversity region; J: joining region; VH: variable module of the immunoglobulin heavy chain; CH: constant module of the immunoglobulin heavy chain; VK: variable module of the immunoglobulin light chain; CK: constant module of the immunoglobulin light chain; polyA: polyA sequence; T7ϕ: 17 transcription terminator].

DETAILED DESCRIPTION OF THE INVENTION

This invention provides heterologous DNA expression vectors, based on recombinant defective viral genomes expressing, at least, an antigen suitable for the induction of immune response against various infectious agents of different animal species, or an antibody affording protection against an infectious agent, provided with high safety and cloning capacity, and which may be designed so that their species specificity and tropism may be easily controlled.

The term "infectious agent" in the sense in which it is used in this description includes any viral, bacterial or parasitic infectious agent that can infect an animal and cause a pathology.

The term "animal species" includes animals of any species, usually mammalians, and swine, canine or feline in particular.

In a specific realization of this invention, expression vectors are obtained based on recombinant defective viral genomes expressing antigens suitable for the induction of systemic and secretory immune responses, for the prevention of mucosal infections, designed to enable an easy control of species specificity and their tropism for the infection of enteric or respiratory mucosae, which makes them quite adequate for the induction of mucosal and lactogenic immunity, of particular interest in the protection of newborn animals against infections of the intestinal tract in another specific realization of this invention, an expression vector is provided based on a recombinant defective viral genome expressing, at least, one antibody which affords protection against an infectious agent.

The expression vectors obtained by means of this invention comprise a defective viral genome derived from a virus, preferably, a virus with RNA genome and positive polarity, that maintains the 3' and 5' ends of the parental virus, has internal deletions and depends on a helper virus for its replication. Therefore, the invention provides, additionally, a defective virus genome comprising the genome of a parental virus having viral replicase recognition signals located at the 3' and 5' ends, comprising also internal deletions, and in which the aforesaid defective viral genome depends on a helper virus supplying the functional and structural proteins for the replication and encapsidation of the recombinant defective viral genome. In a specific realization, the defective viral genome comprises, additionally, the complete sequence coding for the parental virus replicase. In this case, if so desired, the helper virus can provide only the structural proteins required for the encapsidation of the recombinant defective viral genome or, alternatively, the functional and structural proteins for the replication and encapsidation of the recombinant defective viral genome. When the virus from which the recombinant defective genome derives is a virus with RNA genome, the expression vector comprises the cDNA complementing the aforesaid defective RNA or a cDNA substantially complementing the aforesaid defective RNA.

The vectors provided by this invention have a high cloning capacity—at least 18 kb—which is the greatest cloning capacity described for a vector based on RNA eukaryotic viruses. Additionally, these vectors have a high safety level because they (a) are based on defective genomes, (b) comprise RNA genomes and do not use DNA as a replicative intermediary, and c) are based on viruses growing in the cytoplasm of infected cells, all of which prevents the defective genome from recombining with the cell chromosome.

In a specific realization of this invention, the obtainment of defective RNA genomes derived from coronaviruses, in particular from TGEV, is described. These genomes have the additional advantage of a very low TGEV recombination frequency ($<1\times10^9$), which prevents the defective genome from recombining easily with the helper virus genome. However, even though this recombination might actually take place, an attenuated virus would be obtained since the invention contemplates the convenience of using the same attenuated virus both as helper virus as well as starting material for the obtainment of the defective genome.

The defective genomes constituting the basis of such vectors can be obtained in different cell systems by means of undiluted serial passages of the virus from which they derive. The DI particle generation frequency can vary much in different virus-cell systems; for this reason it is advisable to make the passages with different virus isolates in different cell lines with the aim of selecting the proper isolate and cell line. After a certain number of passages, the viruses are isolated and then used to analyze the intracellular RNAs produced in the infection with the purpose of observing the possible appearance of bands not corresponding to any viral mRNA, in which case, in order to analyze the nature of these new RNAs—subgenomic or defective—the undiluted serial passages with the parental virus are continued. After some passages, the evolution of the RNA pattern is analyzed throughout the serial passages and, for this purpose, cells of the suitable cellular system are infected with viruses originating from different passages and the produced RNAs are analyzed by conventional techniques, for example, metabolic labeling with $^{32}P_i$ or hybridization with a suitable oligonucleotide. A detailed description of the obtainment and characterization of some defective RNAs derived from TGEV is made in Example 1.

With the defective RNAs it is possible to obtain the corresponding cDNA—complementing or substantially complementing—the aforesaid defective RNAs, by means of a, reverse transcriptase (RT) reaction and polymerase chain reaction (PCR) amplification, hereinafter RT-PCR. After this, it is possible to clone the cDNA in appropriate plasmids, for example Bluescript II, under the control of efficient promoters.

The resulting plasmids contain the defective viral genome under the control of some regulatory elements, containing signals for the regulation and control of replication and for the initiation and termination of transcription and translation. Therefore, these plasmids can include polyA sequences, auto-catalytic cut sequences or for the recognition of restriction enzymes allowing the insertion of the heterologous DNA, and the corresponding regulation, control and termination signals.

The plasmids thus obtained, containing the defective genome, or the corresponding cDNA, can be manipulated by conventional genetic engineering techniques in order to clone with increased efficiency, at least, one heterologous DNA sequence coding for a specific activity, under the control of the promoter of a gene present in the defective genomes or any other promoter of the virus from which the defective genome or variant of these promoters derives, and of the regulatory sequences contained in the resulting expression vector. Example 2 describes the generation of expression vectors coding for antigens inducing protection against different viruses.

The expression vectors obtained from this invention can express one or more activities, such as one or more antigens capable of inducing immune responses against different infectious agents, or one or more antibodies providing protection against one or more infectious agents. In one specific and preferred realization, these vectors express at least one antigen capable of inducing a systemic immune response or mucosal immune response against different infectious agents that propagate in respiratory or enteric mucosae. In another specific and preferred realization, the said expression vectors express, at least, one gene coding for the heavy and light chains of an antibody of any isotype (for example: $IgG_1$, IgA, etc.) that confers protection against an infectious agent. In a specific case the antibody expressed is the monoclonal antibody identified as 6A.C3 (see Example 4) which neutralizes TGEV, expressed with isotypes $IgG_1$, or IgA in which the constant part of the immunoglobulin is of porcine origin.

In a specific realization of this invention, cloning of the heterologous genes in a plasmid, containing one cDNA of a defective RNA derived from, was done after ORF1b, following the S gene initiation codon (AUG), and in reading frame with this gene (Example 2). Alternatively, the heterologous DNA sequences can be cloned in other areas of the genome, for example, in the zones corresponding to ORFs 1, 2 or 3 of TGEV. From the resulting plasmids, RNAs were expressed using a suitable polymerase, with which appropriate cells—previously infected with an attenuated helper virus—were transformed, enabling to recover virions containing the helper virus genome and other virions with defective genome (FIG. 17).

Alternatively, this invention's expression vectors allow the expression of one or several genes using the strategy described above. To that end, one or several promoters can be used, or a promoter and several internal ribosome entry sites (IRES) or, alternatively, several promoters and an internal ribosome entry site.

This invention also provides a recombinant system to express heterologous proteins comprising (a) the vector described above and (b) a helper virus which facilitates the proteins involved in the replication and encapsidation of the recombinant defective viral genome. Therefore, a recombinant system for the expression of heterologous proteins is provided, based on recombinant defective viral genomes expressing protein with at least one specific activity, comprising:

a) a recombinant vector containing a defective viral genome for which, in its case, a cDNA has been obtained, capable of being manipulated by means of conventional genetic engineering, containing the viral replicase recognition signals located at the 3' and 5' ends, comprising, additionally, internal deletions, and at least one internal DNA sequences coding for one activity, for example, an antigen capable of conferring systemic and mucosal immunity; or an antibody conferring protection against and infectious agent; and b) a helper virus providing the functional and structural proteins for the replication and encapsidation of the defective genome.

Alternatively, the aforesaid recombinant system for the expression of heterologous proteins comprises an expression vector, of the type described above, comprising the complete sequence coding for the parental virus replicase and a helper parental virus which provides structural proteins for the encapsidation of the defective genome and, optionally, the functional proteins (replicase) for the replication of the defective viral genome.

These systems enable the expression, either of antigens capable of inducing an immune response or of antibodies that confer protection against infectious agents, for which reason they are suitable to be used with vaccinal purposes and for protection against infections.

This invention also provides vaccines capable of inducing protection against infections caused by various infectious agents in different animal species comprising (i) the recombinant system described above, consisting of: (a) an expression vector based on a defective viral genome in which the heterologous DNA sequence is cloned, and (b) the helper virus collaborating in the replication of the defective genome together with, optionally, (ii) a pharmaceutically acceptable excipient. The vaccines provided by this invention are, therefore, suitable for the conferring of immunity against various infectious agents affecting different animal species.

"To confer immunity", in the sense used in this description, should be understood to mean the starting in a receptor organism (animal to be treated), by the recombinant system as described above, of the suitable mechanisms, such as antigen-presenting cells, B and T lymphocytes, antibodies, substances potentiating cell immune response (interleukines, interferons, etc.), cell necrosis factors and similar substances that produce protection in animals against infections caused by pathogenic agents.

The vaccines provided by this invention can be monovalent or multivalent, depending on whether the expression vectors present in the recombinant system express one or more antigens capable of inducing an immune response against one or more infectious agent. The expression vectors can be monovalent or polyvalent depending on whether they express one or more antibodies conferring protection against one or more infectious agent.

Species specificity is controlled in such a way that the helper virus will express an envelope protein suitable for recognition by the cell receptors of the corresponding species. A specific group of vaccines obtained from this invention comprise as helper virus a coronavirus, preferably a porcine, canine or feline coronavirus.

These vaccines are especially indicated against infectious agents that affect the porcine, canine and feline species, infecting the mucosae or using mucosae as the route of entrance.

A specific realization of this invention provides monovalent vaccines capable of protecting pigs, dogs and cats against various porcine, canine and feline infectious agents, and tropism is controlled by expressing the S glycoprotein of a coronavirus.

The monovalent vaccines against porcine infectious agents can contain an expression vector expressing an antigen selected from the group composed essentially of antigens of the following porcine pathogens: *Actinobacillus pleuropneumoniae, Actinobacillus suis, Haemophilus parasuis, Porcine parvovirus, Leptospira, Escherichia coli, Erysipelothrix rhusiopathiae, Pasteurella multocida, Bordetella bronchiseptica, Clostridium sp., Serpulina hyodisenteriae, Mycoplasma hyopneumoniae*, porcine epidemic diarrhea virus (PEDV), porcine respiratory coronavirus, rotavirus, or against the pathogens that cause porcine reproductive and respiratory syndrome, Aujeszky's disease (pseudorabies), swine influenza, transmissible gastroenteritis and the etiologic agent of atrophic rhinitis and proliferative ileitis.

The monovalent vaccines against canine infectious agents can contain an expression vector expressing an antigen selected from the group constituted essentially of antigens of the following canine pathogens: canine herpesviruses, canine adenovirus types 1 and 2, canine parvovirus types 1 and 2, canine reovirus, canine rotavirus, canine coronavirus, canine parainfluenza virus, canine influenza virus, distemper virus, rabies virus, retrovirus and canine calicivirus.

The monovalent vaccines against feline infectious agents can contain an expression vector expressing an antigen selected from the group constituted essentially of antigens of the following feline pathogens: feline calicivirus, feline immunodeficiency virus, feline herpesviruses, feline panleukopenia virus, feline reovirus, feline rotavirus, feline coronavirus, feline infectious peritonitis virus, rabies virus, feline *Chlamydia psittaci*, and feline leukemia virus.

The vectors can express an antibody that confers protection against an infectious agent, for example, a porcine, canine or feline infectious agent, such as those described above. In a specific realization, some vectors were produced expressing the recombinant monoclonal antibody identified as 6A.C3 which neutralizes VGPT.

The vaccines obtained from this invention are capable of protecting piglets by means of inducing lactogenic immunity, which is of special interest in the protection of neonatal piglets against infections of the intestinal tract.

In general, the vaccines obtained from this invention can contain a quantity of antigen capable of introducing into the animal to be immunized a helper virus a titer of, at last, $10^8$ plaque forming units (pfu).

As excipient, a diluent such as physiological saline serum or other similar saline solutions may be used. Likewise, these vaccines can also contain an adjuvant like those commonly used in the formulation of vaccines: aqueous (aluminum hydroxide, QuilA, alumina gel suspensions and similar), or oily [based on mineral oils, glycerides and fatty acid by-products and their mixtures, for example, Marcol 52 (ESSO Española S.A.), Simulsol 5100 (SEPIC) and Montanide 888 (SEPIC)].

These vaccines can also contain cell response potentiator substances (CRP), i.e., T helper cell ($Th_1$ and $Th_2$) subpopulation potentiator substances, such as interleukin 1 (IL-1), IL-2, IL4, IL-5, IL6, IL-12, g-IFN (gamma interferon), cell necrosis factor and similar substances that might, in theory, provoke cell immunity in vaccinated animals. These CRP substances could be used in vaccine formulations with aqueous or oily adjuvants. Other types of adjuvants that modulate and immunostimulate cell response can also be used, such as MDP (muramyl dipeptide), ISCOM. (immuno stimulant complex) or liposomes.

This invention provides multivalent vaccines capable of preventing and protecting animals from different infections. These multivalent vaccines can be prepared from expression vectors in which the different sequences coding for the corresponding antigens have been inserted in the same recombinant vector, or by constructing independent recombinant vectors that will be mixed afterwards for their co-inoculation together with the helper virus. Therefore, these multivalent vaccines comprise a is recombinant system in which the expression vector itself contains more than one DNA sequence coding for more than one infectious agent or, alternatively, the recombinant system used in the preparation of the vaccine can contain different expression vectors, each one of which expresses at least one different antigen. The actual limitation in this type of multivalent vaccines is that the mentioned expression vectors must express antigens of infectious agents of the same animal species and that the helper virus must be the suitable one for that particular species. Analogously, multivalent vaccines can be prepared that comprise multivalent vectors using sequences coding for antibodies that confer protection against infectious agents instead of sequences coding for the antigens. These vectors can contain a recombinant system comprising either an expression vector containing more than one DNA sequence coding for more than one antibody or different expression vectors expressing, each one of them, at least, one different antibody.

A specific realization of this invention provides vaccines capable of protecting pigs, dogs and cats against various porcine, canine and feline infectious agents, respectively.

To that end, the expression vectors contained in the recombinant system of the vaccine must express different antigens of the mentioned porcine, canine or feline pathogens.

The vaccines of this invention can be presented in liquid or freeze-dried form and can be prepared by suspending the recombinant systems in the excipient. If the said systems are in freeze-dried form, the excipient itself can be the diluent.

Alternatively, the vaccines attained by means of this invention can be used in combination with other conventional vaccines, either as part of them or as diluent or freeze-drying fraction to be diluted with other, either conventional or recombinant, vaccines The vaccines provided by this invention can be administered to the animal via oral, nasal, subcutaneous, intradermal, intraperitoneal or intramuscular routes, or by aerosol.

The invention also provides a method for the immunization of animals, especially pigs, dogs and cats, against various infectious agents simultaneously—comprising the administration via oral, nasal, subcutaneous, intradermal, intraperitoneal or intramuscular routes, or by aerosol (or their combined forms)—of a vaccine containing an immunologically efficacious quantity of a recombinant system provided by the present invention.

Additionally, the invention also provides a method for the protection of newborn animals against infectious agents that infect the said animals, consisting of the administration via oral, nasal, subcutaneous, intradermal, intraperitoneal and intramuscular routes, or by aerosol (or their combined forms), to mothers, before or during the period of gestation, or to their progeny, of a vaccine containing an immunologically efficacious quantity of a recombinant system provided by this invention.

The invention is illustrated by means of the following examples that describe in detail the obtainment of defective viral genomes, their characterization, the construction of plasmids and their manipulation with the purpose of obtaining the expression vectors and the induction of neutralizing antibodies against different infectious agents of various species.

EXAMPLE 1

Generation of Defective Particles Derived from TGEV 1.1 Undiluted Serial Passages of TGEV Strains at High Multiplicity of Infection (m.o.i.)

In order to promote the generation of defective particles, or the imposition of those already existing in small proportion in the viral population, serial passages of different undiluted TGEV isolates were made in different cell systems. Because the frequency with which DI particles are generated can vary much in different virus-cell systems, the passages were done with different TGEV isolates (THER-1 and PUR46-mar 1CC12) in ST (swine tests, swine testicle epithelial cells) cell lines.

Strain THER-1 (transmissible gastroenteritis Helper Enteric and Respiratory coronavirus, strain 1) is a mutant attenuated by 20 passages in ST cell cultures derived from the PUR46-MAD strain [Sanchez et al., Virology 174, 410–417 (1990)]. Strain PUR46-mar 1CC12 is also described by Sanchez et al (supra).

Figure 1:
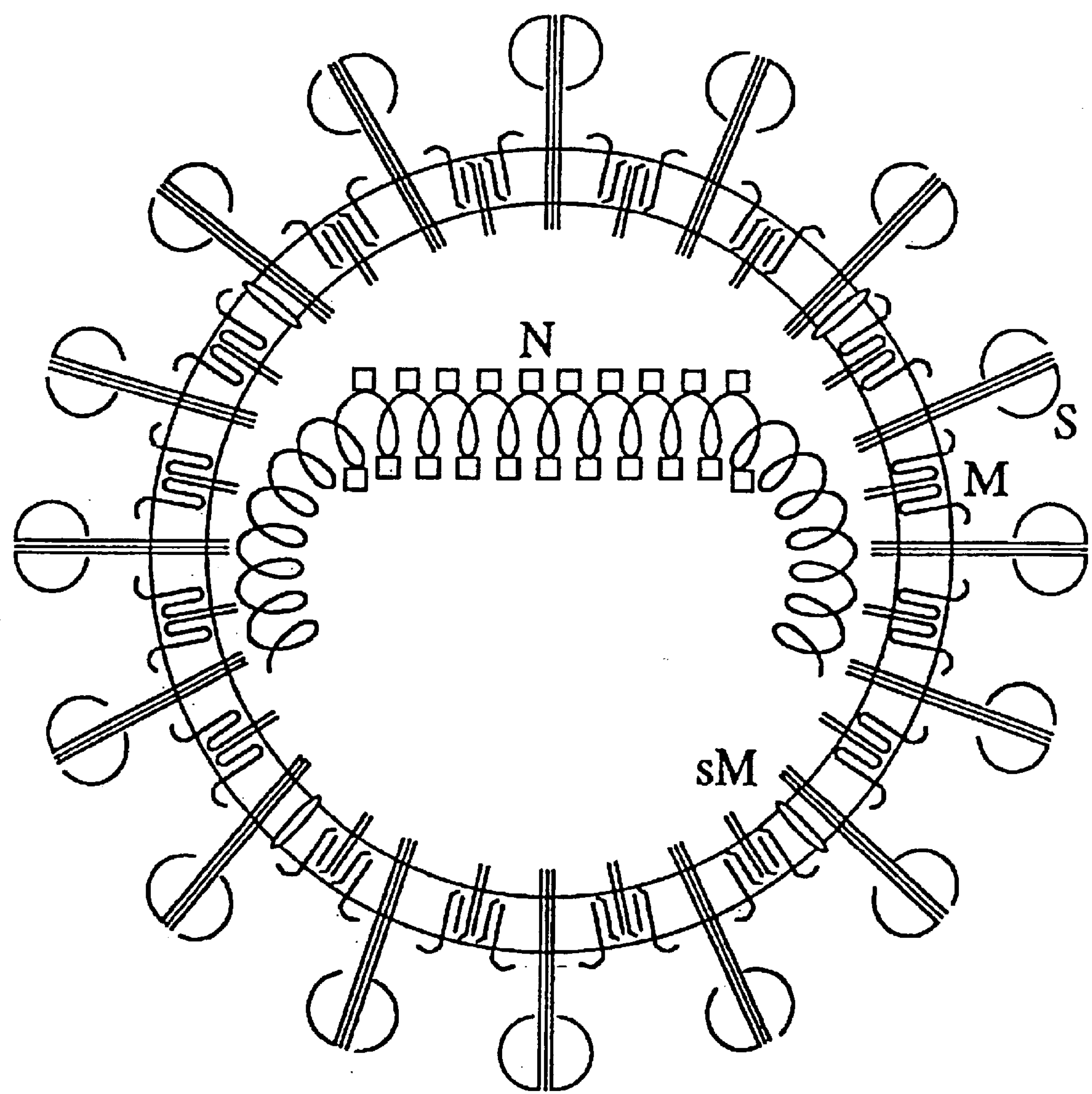
FIG. 1 shows the structure of TGEV. The virion is a spherical particle consisting of a lipidic envelope in whose interior is a single-chain, positive-polarity RNA molecule of 28.5 kilobases (kb). This RNA is associated to an N protein forming the nucleocapsid. M and sM structural proteins are included in the membrane. Protein S groups itself into trimers, and is anchored on the external part of the envelope forming the peplomers.
Figure 2:
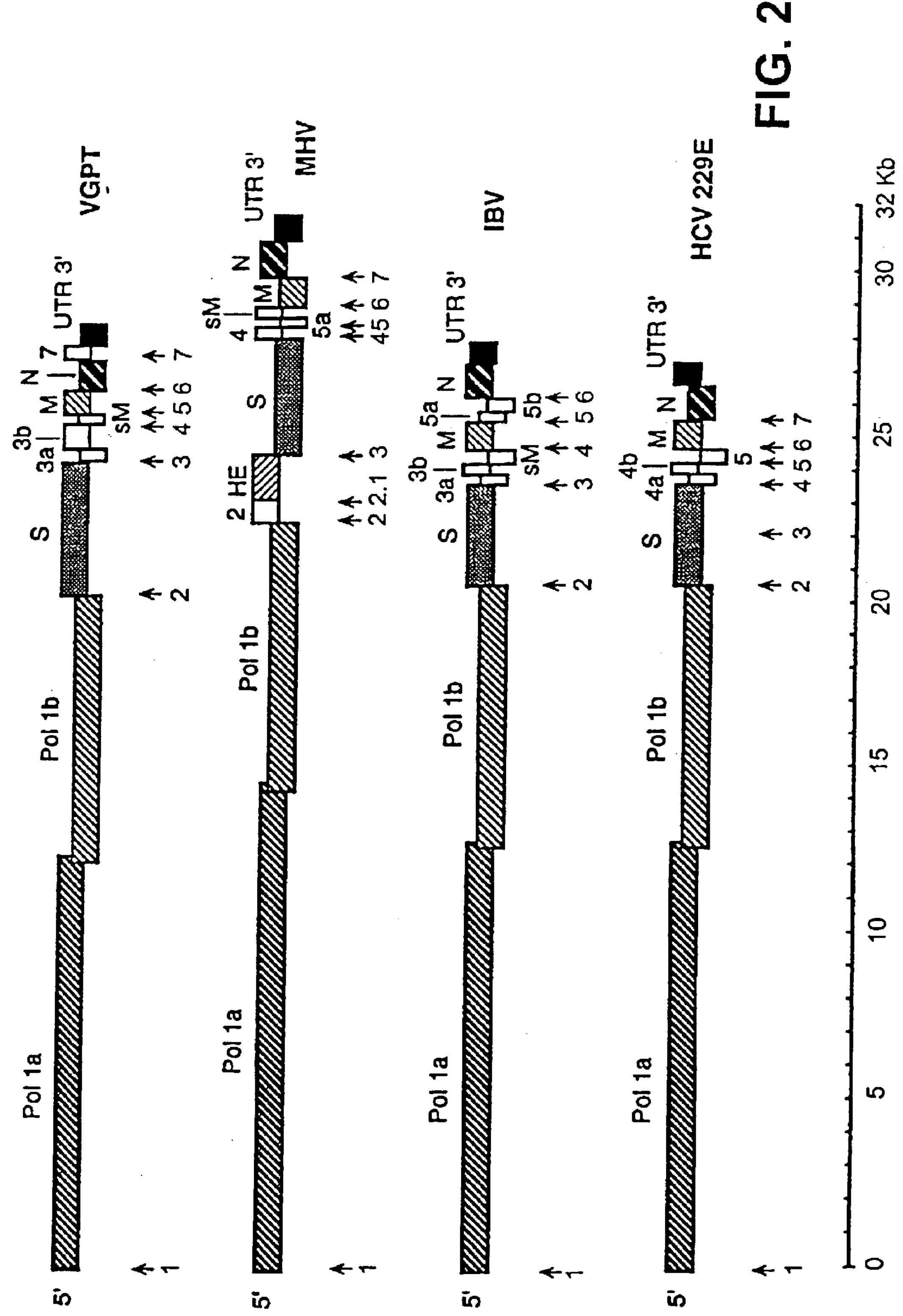
FIG. 2 shows the genomic organization of the four sequenced coronaviruses: is MHV, IBV, HCV229E (human coronavirus 229E) and TGEV. The open reading frames coding for each protein are shown to scale. In each genome, the beginning of the RNAs expressing each virus is indicated with an arrow. The number of messenger RNAs (mRNA) expressed by viruses MHV or TGEV may vary depending on the viral strain. In this outline, the TGEV arrows correspond to the mRNAs expressed by strain THER-1. The mRNAs are 3'-coterminal and are numbered in decreasing size order.
Figure 3:
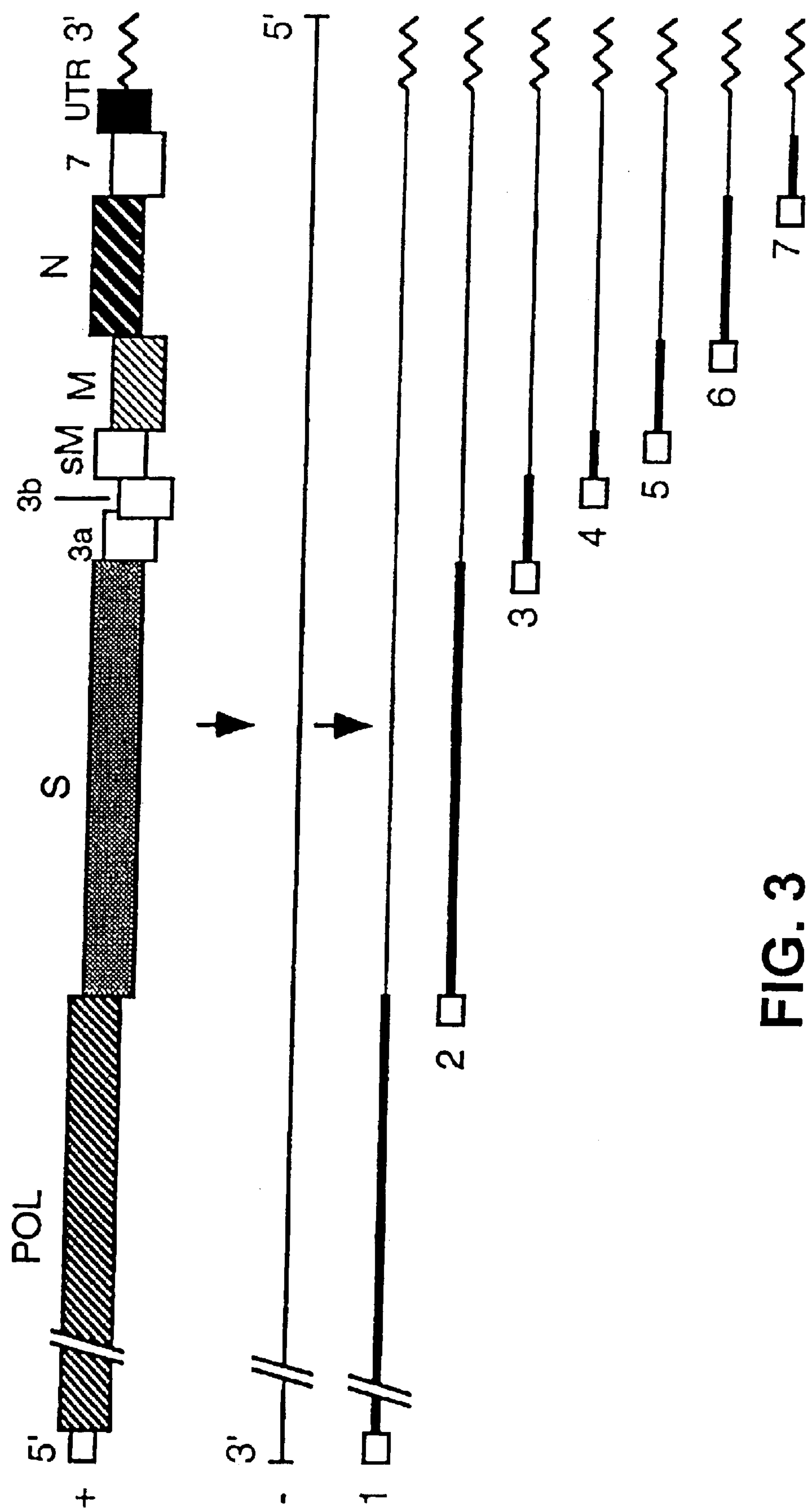
FIG. 3 shows the expression of the TGEV genome, strain THER-1. The disposition of the open reading frames (ORF) in the genome is indicated: Pol, polymerase; S, sM, M and N, structural proteins; nsp 3a, 3b and 7, non-structural proteins (protein 3b is not produced with this virus). The genome is transcribed in an RNA of equal length but of negative polarity (−) that will serve as a template for the synthesis of the 7 mRNAs (1 to 7). In each mRNA are represented the common sequence, leader, of the 5' end (square), the polyadenine section at the 3' end and the zone which is translated in each one of them (thick lines).
Figure 4:
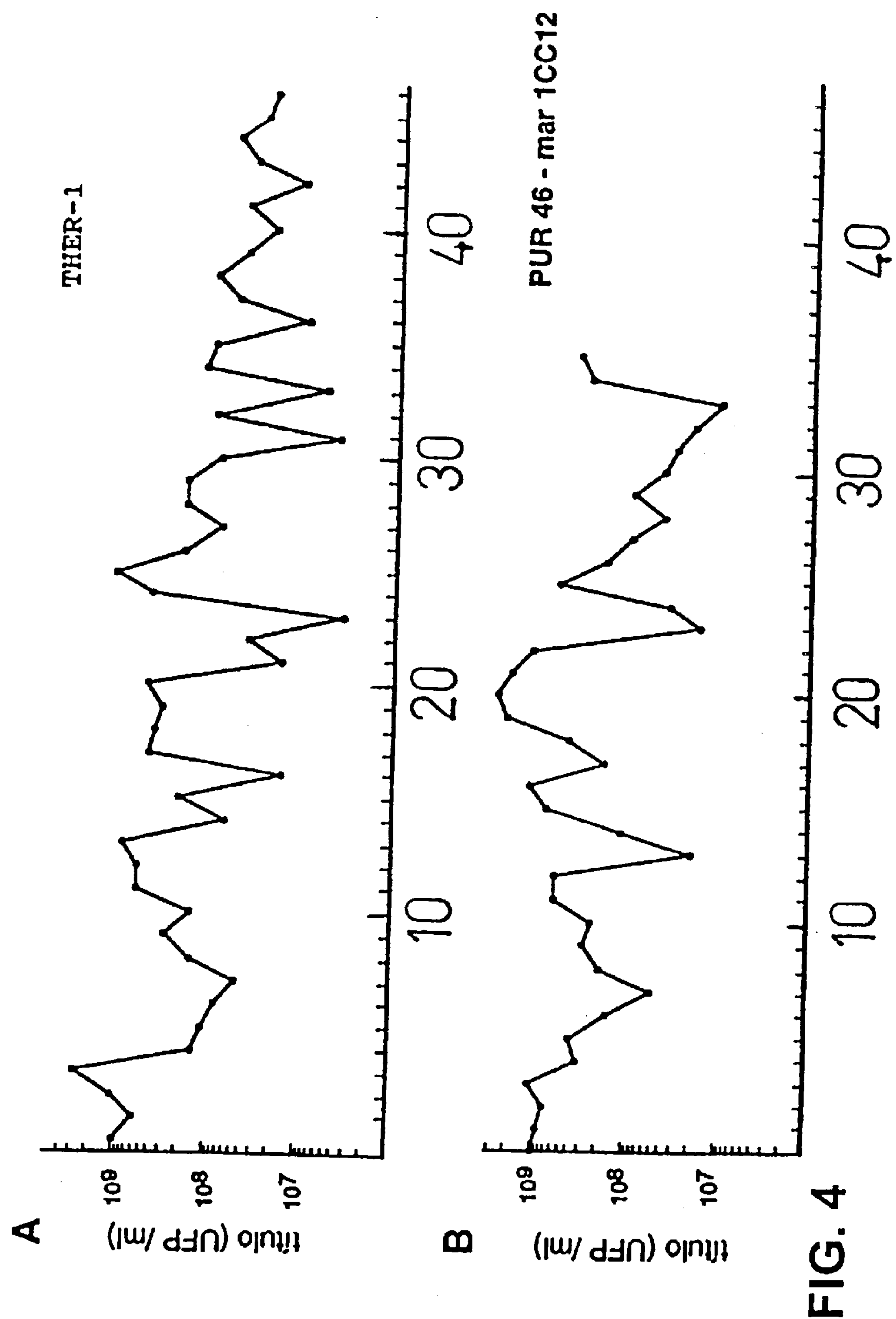
FIG. 4 shows the evolution of the titer of TGEV THER-1 (A) and PUR46-mar 1CC12 (B) isolates with the passage number at high multiplicity of infection (m.o.i.) in ST cells.

Each TGEV strain was passaged undiluted 35 times in ST cells. The m.o.i. of the first passage in each one of the three cases was 100 pfu per cell. The supernatant of each passage was collected between 20 and 48 hours post infection (h.p.i.), upon observance of a clear cytopathic effect—normally when the said effect was affecting more than half of the cell monolayer—, and half of the volume of this supernatant was used in the infection of the next passage. Virus titer variation with passage number is shown in FIG. 4. Viral titer ranged between two logarithmic units throughout the serial passages of each virus. In the case of strain THER-1, the titer in passages 30 to 46 was lower than in the first thirty passages.

Figure 5:
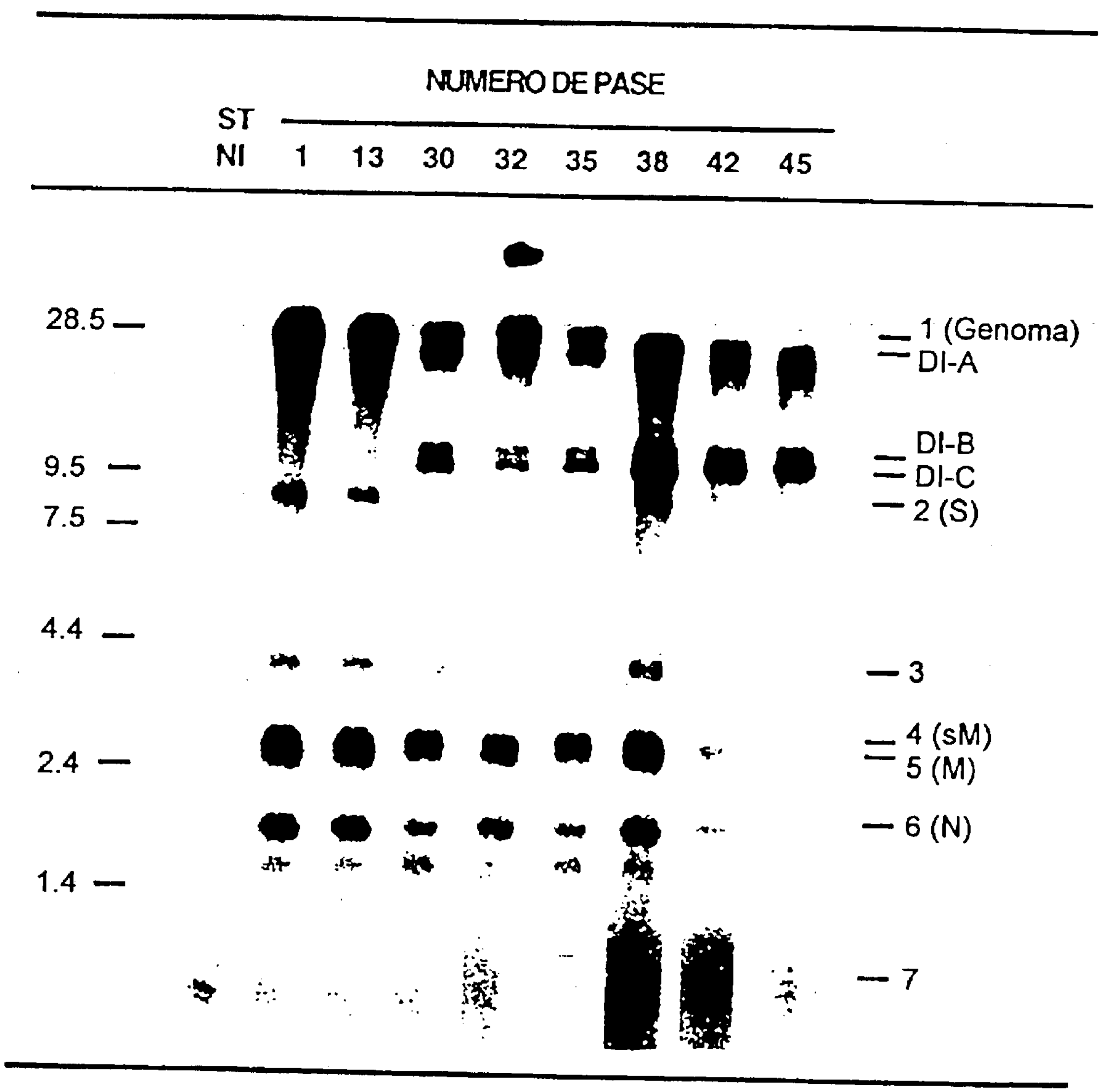
FIG. 5 shows the results of the electrophoretic analysis of the RNAs produced in ST cells infected with THER-1 virus passaged 46 times at high m.o.i. The passage number is indicated above each lane and the bars to the left indicate the position of the molecular weight markers (genomic RNA of the TGEV and GibcoBRL markers), expressed in kb. The bars to the right indicate the TGEV mRNAs and the defective interfering (DI) RNAs. NI, not infected.

The viruses that had been passaged 35 times in ST cells were used for the analysis of intracellular RNAs produced in the infection. The RNAs, metabolically labeled with $^{32}P_1$ between hours 6 and 9 post infection, were analyzed [Maniatis et al., *Molecular cloning: A Laboratory Manual*, Cold Spring Harbor Laboratory, (1982)]. In THER-1-p35 infection (THER-1 strain virus passaged 35 times at high m.o.i.) three intense bands were observed which did not correspond to any viral mRNA. These bands were located between the genomic RNA and the S gene messenger (FIG. 5). To analyze the nature of these new subgenomic RNAs, undiluted serial passages were continued with strain THER-1. After 46 passages, the evolution of the RNA pattern throughout the serial passages was analyzed. To that end, ST cells were infected with virus from various passages and the produced RNAs, metabolically labeled, were analyzed in a denaturing agarose gel (FIG. 5). Whereas only genomic RNAs and subgenomic viral messengers were detected in the first passages, in passage 30 three new RNAs of 22, 10.6 and 9.7 kb (RNAs A, B and C shown in FIG. 5 as DI-A, DI-B and DI-C, respectively) were detected. These subgenomic RNAs remained in stable form throughout the following 15 passages, interfering notably with genomic RNA replication and the synthesis of the mRNAs of the helper virus (FIG. 5, lanes 30 to 45). These results indicate that the three RNAs generated or amplified by the undiluted serial passages are stable and that at least one of them is interfering.

1.2 Characterization of Subgenomic RNAs 1.2.1 Analysis of the Ends and Internal Regions To determine if subgenomic RNAs A, B and C had the standard structure of a coronavirus defective RNA, and especially, if they preserved the 5' and 3' ends of the wild genome and that its small size was due to internal deletions, several hybridization assays were carried out with probes specific for the virus. To that end, the RNA from cells infected with the THER-1-STp35 virus (THER-1 strain viruses, passaged 35 times in ST cells) was extracted and its hybridization was analyzed with specific viral probes in a Northern-blot assay (Maniatis et al., supra) using oligonucleotides complementary to the leader and the viral 3' end sequence. In each case, the RNA from cells infected with THER-1-p1 virus (strain THER-1 virus passaged once in ST cells) and from uninfected ST cells (NI) (lanes 1 and 2 of each filter, respectively) were used as control. The oligonucleotides used as probes are complementary to the leader RNA (positions 66–91 of the 5' end of the parental genome), to the untranslated region of the 3' end (nucleotides 28524–28543 of the 5' end of the parental genome), and to structural genes M and N (positions 97–116 and 5–24 starting from the primer AUG of each gene, respectively). The bars on the right indicate the positions of the viral mRNAs and subgenomic RNAs A, B and C.

Figure 6:
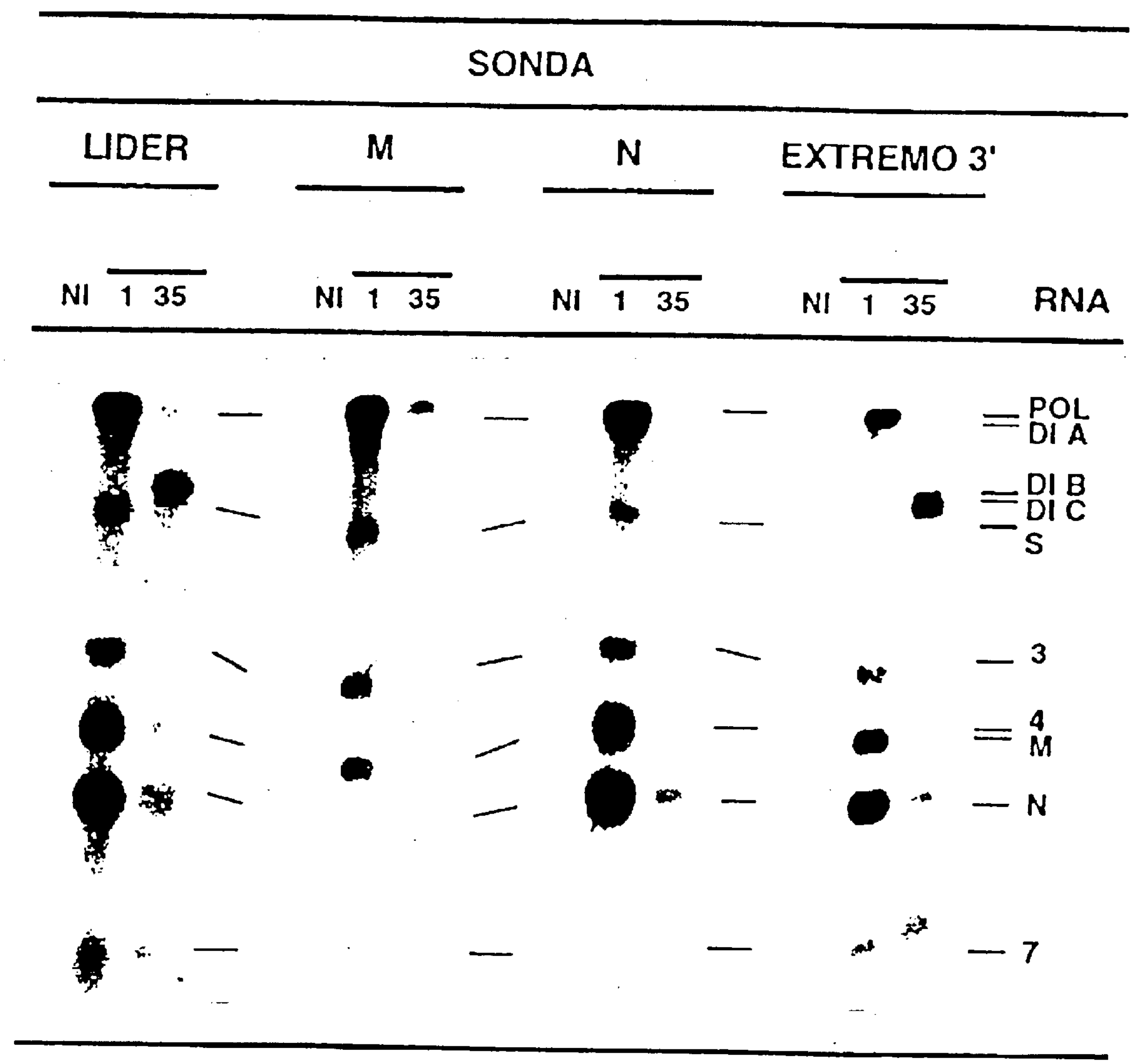
FIG. 6 shows the results of the Northern-blot assay of the RNA of ST cells infected with the THER-1p35 virus.

As shown in FIG. 6, the two oligonucleotides hybridized with all the parental virus mRNAs, and they also detected RNAs A, B and C, indicating that these RNAs have gone through internal deletions and maintained their ends. As an initial approach to an analysis in regard to which genomic sequences were present in these RNAs, the RNA of infected cells was hybridized with oligonucleotides complementary to the genes of structural viral proteins S, M and N. None of them hybridized with the defective RNAs, suggesting that the structural protein genes had been deleted. Thus, subgenomic RNAs A, B and C maintain the parental virus ends and have internal deletions.

1.2.2 Propagation of RNAs A. B and C

Figure 7:
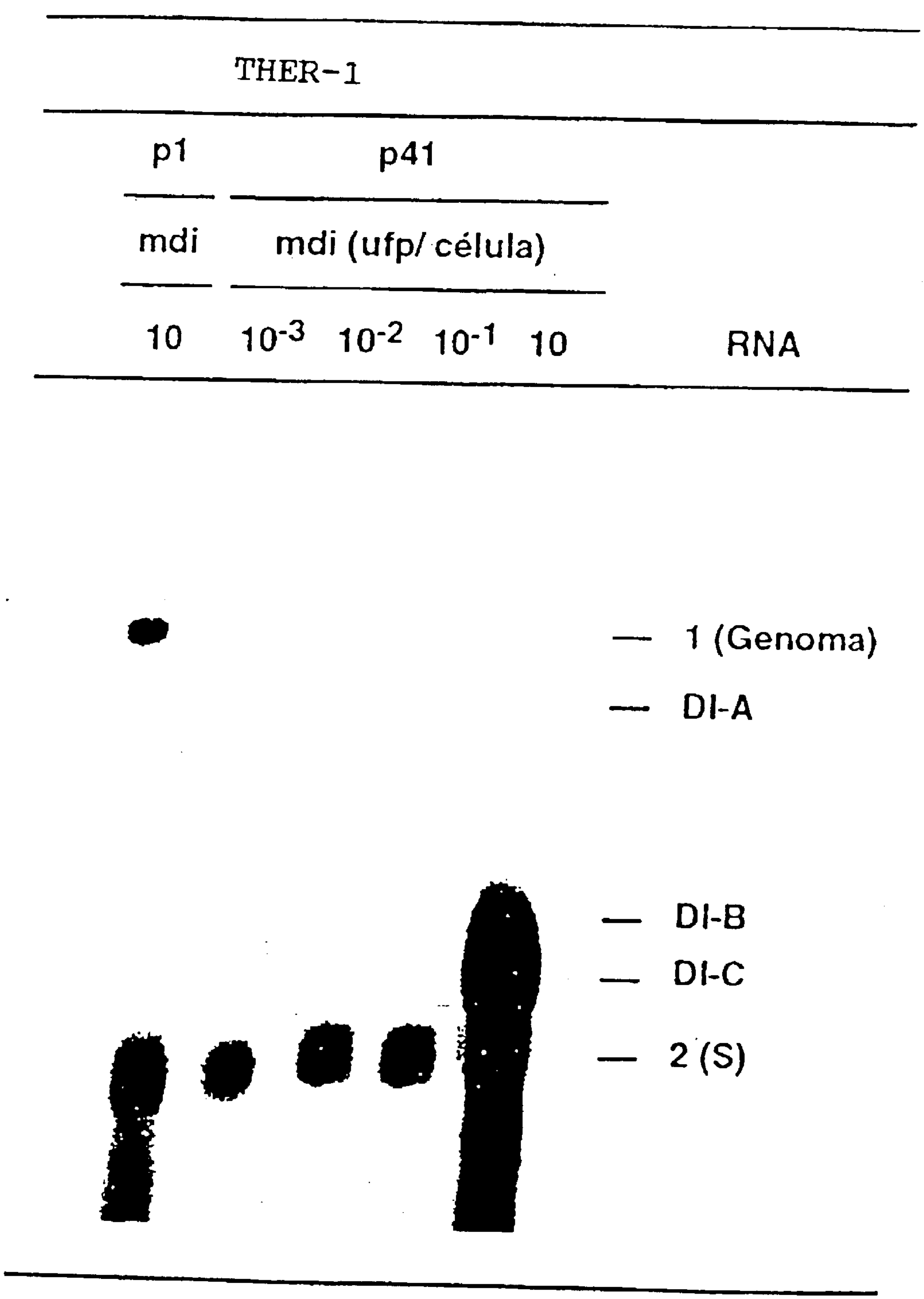
FIG. 7 shows the results of the Northern-blot assay of the RNA proceeding from diluted passages of the THER-1-STp41 virus in ST cells.

In order to verify that RNAs A, B and C are defective genomes, dependent on the parental virus for their propagation in culture, ST cells were infected with virus THER-1-STp41 (THER-1 virus strain passaged 41 times in ST cells) at different m.o.i.: 10, 0.1, 0.01 and 0.001 pfu/cell. The virus resulting from this passage, collected at 10 h.p.i., was titrated and amplified in a second passage in ST cells, which in turn was used to infect new cells from which the cytoplasmic RNA was extracted (Maniatis et al., supra). The RNA was analyzed in a Northern-blot assay using an oligonucleotide complementary to the leader RNA FIG. 7 shows the results obtained. The m.o.i. are indicated over each lane ($10^{-3}$, $10^{-2}$, $10^{-1}$ and 10 pfu/cell). As negative control was included the RNA from an infection of ST cells with THER-1-p1 virus, which does not contain subgenomic RNAs, at m.o.i. of 10 pfu/cell (first lane). In the lane corresponding to the infection with THER-1-STp41 virus at m.o.i. of 10 pfu/cell, positive control, the genomic RNAs (mRNA 1) are labeled, and so are defective RNAs A, B and C (represented as DI-A, DI-B, DI-C) and the corresponding S gene (mRNA 2).

It is observed that when the m.o.i. of the first passage (the "bottleneck" in this experiment, as the passages that follow are amplification passages) is 0.1 pfu/cell or less, RNAs A, B and C are lost, in conditions in which the genomic RNA and the mRNA of the virus are detected in the expected proportions (FIG. 7). The three defective RNAs are maintained when the m.o.i. is 10 pfu/cell. Because RNAs A, B and C are found in higher proportion than genomic RNA in the THER-1-p41 virus used in the infection, these results show that the replication or propagation of these RNAs requires that the cells be infected by defective virus and also by the helper virus. Thus, RNAs A, B and C require functions of the helper virus which are to be provided in trans. Therefore, RNAs A, B and C are defective genomes, depending on a helper virus for their propagation.

Figure 8:
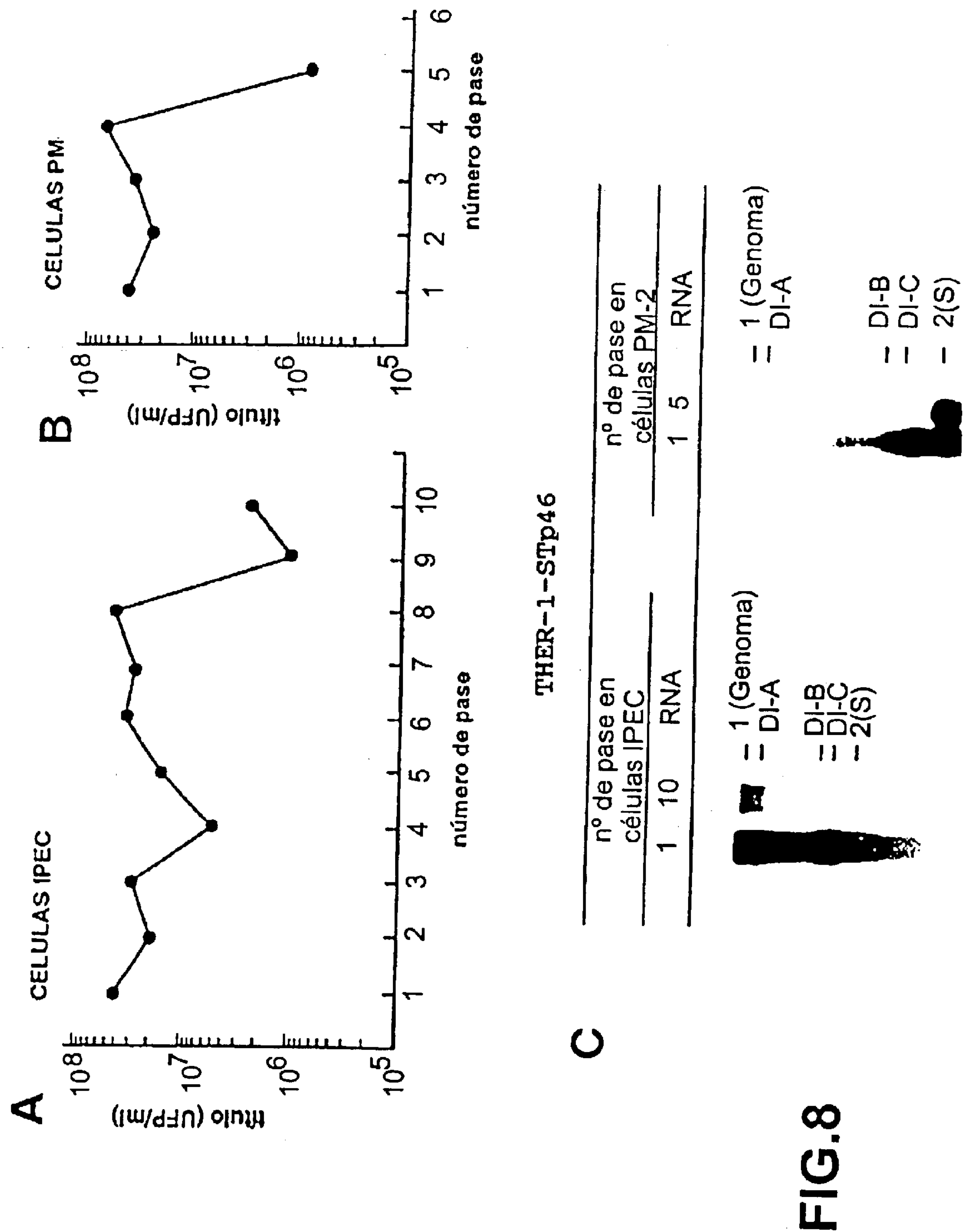
FIG. 8 shows the effect of the cell line change on the propagation of defective RNAs A, B and C. Virus THER-1-STp46 was passaged ten times undiluted in IPEC (intestinal pig epithelium cells), and five times in PM (porcine macrophage) cells.

1.2.3 In Vitro Generation, Amplification. Propagation and Interference of DI RNA in Another Cell Line In vitro generation, amplification, propagation and interference of RNA DI are specific to the cell line, and for this reason the effect that a change of cell line might have on defective RNAs was studied. To that end, the THER-1-STp46 virus (THER-1 virus passaged 46 times at a high m.o.i. in ST cells) was subjected to a new series of undiluted passages, in intestinal porcine epithelial cells (IPEC) and porcine macrophages (PM). FIG. 8 shows titer variation and passage number through 10 passages in IPEC (Figure 8A) and 5 passages in PM (FIG. 8B). Viral yield in both cell lines was lower than what was obtained in ST cells, and the estimate is that there was a variation ranging between 20 and 0.2 pfu/cell in the m.o.i. of each passage.

The RNA produced in ST cells infected with THER-1-STp46-IPECp1 (THER-1-STp46 virus passaged one time in IPEC cells) and THER-1-STp46-IPECp10 (THER-1-STp46 virus passaged 10 times in IPEC cells) was labeled with $^{33}P_1$ and analyzed in a denaturant agarose gel (FIG. 8C).

The RNA of ST cells infected with THER-1-STp46-PMp1 virus (THER-1-STp46 virus passaged one time in PM cells) and THER-1-STp46-PMp5 (THER-1-STp46 virus passaged 5 times in PM cells) was analyzed in a Northern-blot assay with an oligonucleotide complementary to the leader RNA (FIG. 8C).

The results appear on FIG. 8C, which shows that the three defective RNAs remained in the first passage in both cell lines, but only RNA A persisted throughout, at least, five passages in PM, and ten passages in IPEC. In both cases the positions of the RNAs corresponding to the wild genome (1) are marked, RNAs A, B and C (DI-A, DI-B and DI-C respectively) and mRNA 2 (protein S). In the lane corresponding to the THER-1-STp46-PMp5 virus RNA, the position of genomic RNA is indicated—observed only when the exposition period of the autoradiograph was tenfold the period shown on FIG. 8C.

1.3 Encapsidation of Defective Genomes

In order to study whether defective RNAs have the capacity to encapsidate, a partial purification was done simultaneously on viruses THER-1-STp1 (THER-1 virus passaged one time in ST cells) and THER-1-STp41 (THER-1 virus passaged 41 times in ST cells) by means of centrifugation through a 15% weight/volume (w/v) sucrose cushion. The RNA was extracted from the purified virions, and analyzed in agarose gel by means of ethidium bromide staining (FIG. 9A). In passage 41 virions, RNAs A, B and C were detected with the same intensity as genomic RNA, indicating that the three defective RNAs encapsidate efficiently.

To determine if the defective genomes co-encapsidate with the complete genome, or if, on the contrary, they encapsidate independently, THER-1-STp41 virus was purified by centrifugation through sucrose cushions of varying densities, or through continuous sucrose gradients. The RNA of the purified virions in each case was analyzed in a Northern-blot assay with an oligonucleotide complementary to the leader RNA (FIG. 9B). When centrifugation was done through a sucrose cushion of 31% (w/v) (d=1.19 g/ml), only wild genome was detected in the sedimented virions. However, when a sucrose cushion of lower density, 15% (w/v) (d=1.11 g/ml), was used, the three defective RNAs were detected, in addition to the complete genome. In a continuous sucrose cushion (15–42%, w/v) it was possible to enrich the defective virions in the upper fractions of the gradient (density close to 1.15 g/ml), and the standard virions in the lower fractions (density close to 1.20 g/ml), as shown on lanes d and e of FIG. 9B. The upper band in each lane corresponds to the wild type genomes and to defective genome A (DI-A), and the lower band corresponds to defective genomes B and C (DI-B and DI-C). These results indicate that RNAs A, B and C encapsidate efficiently, and that genomes DI-B and DI-C (10.6 and 9.7 kb) do so independently from the wild type genome, in defective virions that are lighter than standard virions.

1.4 Cloning and Sequencing of Defective RNAs B and C. Determination of Their Primary Structure.

1.4.1 Synthesis of Complementary DNA and Amplification of RNAs B and C.

Figure 10:
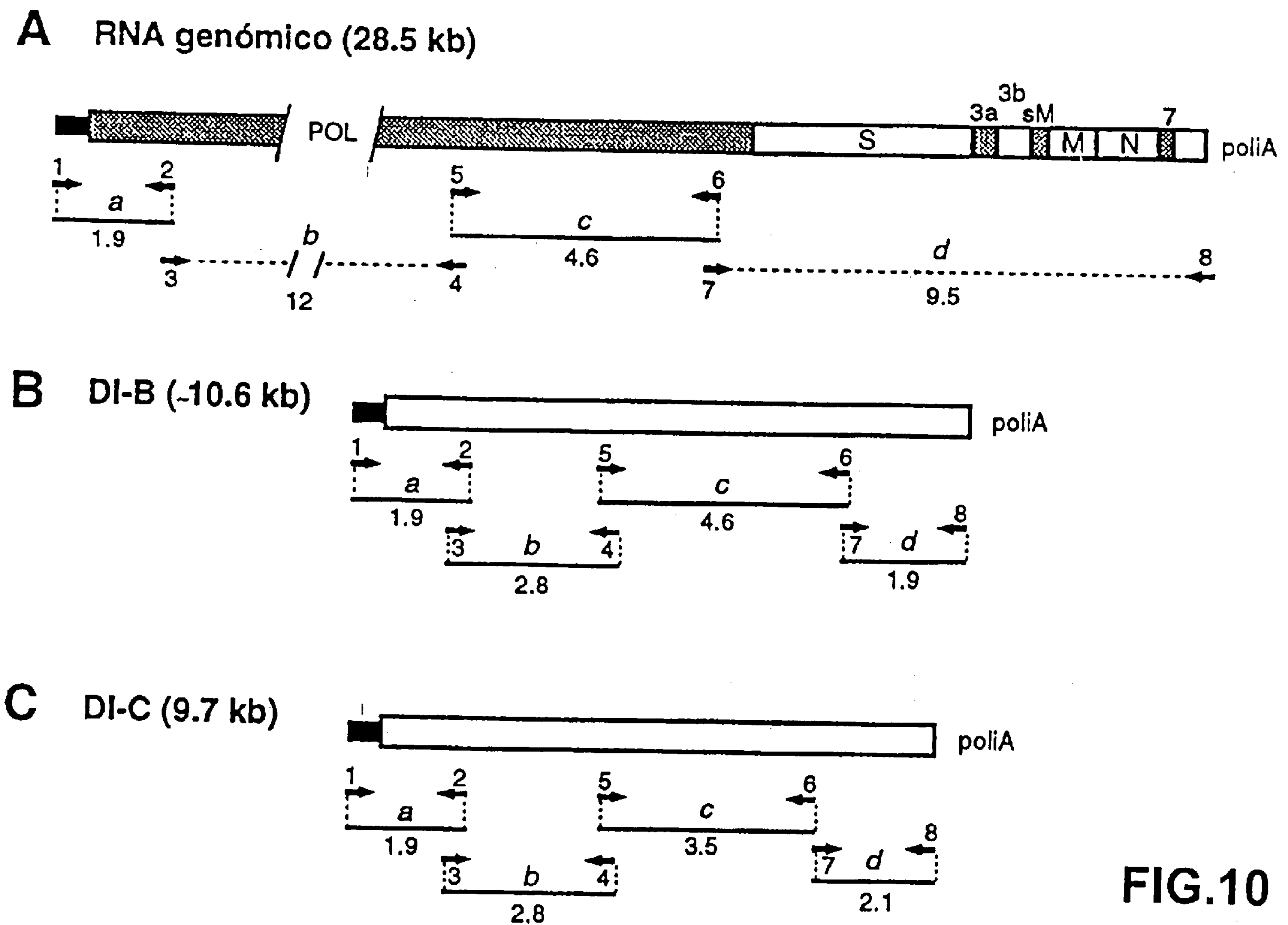
FIG. 10 shows the strategy for the cloning of defective RNAs DI-B and DI-C, in which a schematic representation can be observed of the complementary DNA fragments (cDNA) obtained by RT-PCR, using as template genomic RNA of total length (A), DI-B (B) and DI-C (C). The dotted lines indicate absence of the anticipated fragment due to its large size. The defective RNAs were cloned into four overlapping fragments (a, b, c and d), represented by lines; the numbers below these lines indicate fragment size determined in agarose gels. The oligonucleotides used as primers and their polarity are indicated by means of arrows and numbers. Oligonucleotide sequence is shown in Table 2. Striped or open boxes in (A) indicate the relative position of the viral genes: pol, polymerase; S, M and N, structural genes; 3a, 3b, sM and 7, small ORFs. The shaded thin boxes indicate the leader sequence.

The size of defective RNAs B and C had been estimated, based on their mobility in electrophoresis gels, in 10.6 and 9.7 kb, respectively. On account of their large size, it was not possible to amplify the defective RNAs in a single reverse transcriptase and polymerase chain reaction (RT-PCR) using primers complementary to genome ends. In order to overcome this limitation, the defective genomes were amplified in four independent reactions, using pairs of primers allowing four overlapping fragments to cover the total genome length in every case. These overlapping fragments were designated as a, b, c and d, arranged from the 5' end to the 3' end (FIG. 10). The THER-1-STp41 virus RNA extracted from purified virions was used as a template. This RNA contained the three defective RNAs A, B and C, in addition to the parental genome. As a control, an amplification of the genomic RNA of the THER-1 wild virus was carried out simultaneously.

The sequence and position of the oligonucleotides used as primers in the RT-PCR reaction is indicated in Table 2.

TABLE 2

Characteristics of the oligonucleotides used as primers in the RT-PCR reactions

| SEC. ID. No. | Polarity | ORF Coronavirus | Position in the RNA DI-C[b)] | Restriction Site |
|---|---|---|---|---|
| 1 | + | Leader TGEV | 15–41 | — |
| 2 | – | ORF1a FIPV | 1874–1887 | — |
| 3[a)] | + | ORF1a TGEV | 1524–1550 | XbaI |
| 4[a)] | – | ORF1b TGEV | 4365–4389 | XbaI |
| 5[a)] | + | ORF1b HCV229E | 4097–4114 | EcoRI |
| 6[a)] | – | ORF1b TGEV | 7633–7650 | EcoRI |
| 7 | + | ORF1b TGEV | 7633–7650 | — |
| 8[a)] | – | 3'UTR TGEV | 9691–9707 | SpeI |
| 9 | + | ORF1b TGEV | 8251–8270 | — |

[a)]A restriction site in 5' has been included to facilitate its posterior cloning.
[b)]The position of the oligonucleotide in the corresponding ORF is in relation to the sequence shown on FIG. 12.

Figure 11:
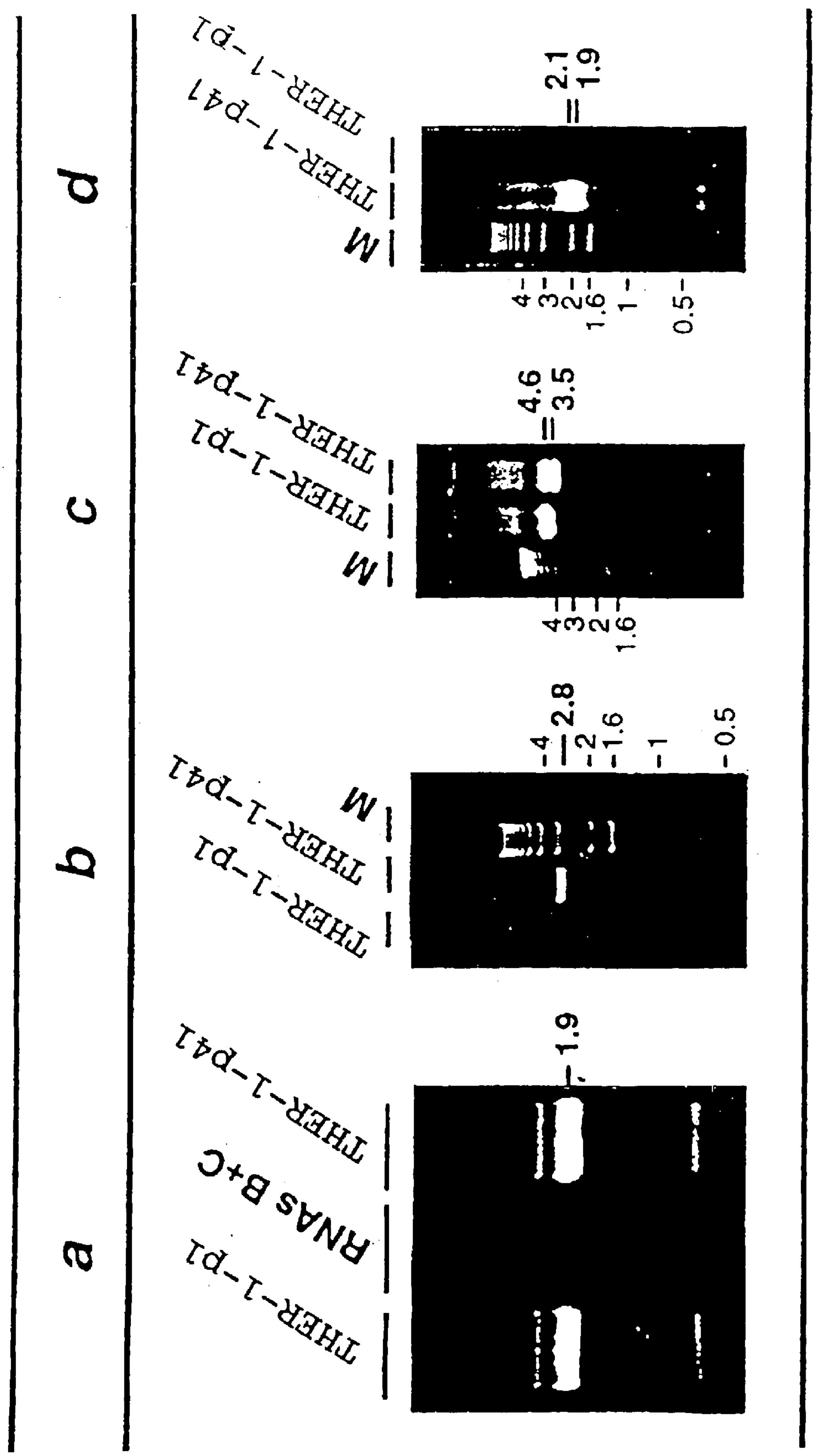
FIG. 11 shows the results of the electrophoretic analysis of PCR products obtained in the amplification of defective RNAs. The RNA of purified virions THER-1p1 or THER-1p41 was used as a template in an RT-PCR reaction with oligonucleotides 1 and 2 (a), 3 and 4 (b), 5 and 6 (c), or 7 and 8 (d), whose sequence and position in the parental genome is indicated in Table 2. The lane corresponding to the RNA template of passage 1 (parental genomic RNA) or of passage 41 (parental RNA, DI-A, DI-B and DI-C), and the lane of DNA mobility markers (M, GibcoBRL) are indicated in each case. The numbers in bold type indicate the size in kb of the amplification products specific for defective RNAs.

The amplification by RT-PCR with primers 1 and 2, of the THER-1-STp41 virus RNA and the parental virus THER RNA gave rise to a dominant PCR product of 1.9 kb (FIG. 11, fragment a). The minor bands observed in this reaction are due to unspecific hybridizations, as they appear in the two lanes. The same RT-PCR reaction was performed starting from an agarose fraction containing a pool of DI-B and DI-C RNAs extracted from a purification with gel, with the same results. This indicates that fragment a is common to all RNA DIs, and corresponds to the 1.9 kb region of the 5' end of the wild TGEV genome.

The amplification with oligonucleotides 3 and 4 gave rise to a unique PCR 2.8 kb product starting from the THER-1-STp41 virus RNA (FIG. 11, fragment b). No PCR product was obtained from the THER-1 control virus RNA, as the size of the expected product was 12 kb. Based on these data, it can be deduced that at least one defective genome has one b fragment of 2.8 kb, and that the others have the same fragment or a larger one which is not detectable in PCR reactions due to its large size.

Oligonucleotides 5 and 6, separated by 4.6 kb in the parental genome, gave rise to two different products of 3.5 and 4.6 kb from the THER-1-STp41 virus RNA (FIG. 11, fragment c). The 4.6 kb product was also obtained from the wild virus RNA used as control. These results suggest that fragment c contains one deletion in at least one defective genome (probably in DI-C, the most abundant defective genome), giving rise to a 3.5 kb fragment by PCR. The 4.6 kb fragment derives from the parental genome present in the THER-1-STp41 virus RNA population, and from those defective genomes that have maintained this region of the genome.

The amplification by RT-PCR with primers 7 and 8 of the parental virus genomic RNA did not generate any bands (FIG. 11, fragment d), since the separation between these oligonucleotides is 9.5 kb in the complete genome (FIG. 10). In contrast, two very intense bands of 1.9 and 2.1 kb were observed when the THER-1-STp41 virus RNA was used as template. These bands appear as a broad continuous band, corresponding to fragment d (FIG. 11), probably because: they co-migrate with a group of minor bands around the 1.9 kb band, preventing their resolution in gels. Heterogeneity has been observed in the size of cloning fragment d (see below).

1.4.2 Assigning Amplification Products (a, b, c and d) to the Different Defective RNAs.

In order to assign the d fragments of sizes varying between 1.9 and 2.1 kb to the different defective genomes, the THER-1-STp41 virus RNA, which had been used as a template, was fractioned in an agarose gel until a clear separation was achieved of the bands corresponding to the RNAs of the wild genome, DI-A, DI-B and DI-C. The bands corresponding to each one of these four RNAs were cut independently and used as a template in the amplification reaction of RT-PCR with oligonucleotides 8 and 9. Starting from the purified genomic band RNA, no PCR product was obtained. From RNA DI-B, a predominant 1.9 kb PCR product was obtained, although less abundant DNAs were also obtained, of variable size close to 1.9 kb, which indicates a certain heterogeneity in this zone. The amplification of RNA DI-C gave rise to a dominant 2.1 kb PCR product. These results allowed to assign the 1.9 kb fragment to the defective RNA B, and the 2.1 kb fragment to RNA DI-C.

Once the d fragments had been assigned, the 3.5 and 4.6 kb c fragments obtained with primers 5 and 6 were assigned to defective RNAs C and B, respectively, since the sum of fragments a to d resulting from this assignment coincided in each case with the sizes of RNAs B and C, estimated by mobility.

Once the complete sequence of genomes B and C had been determined, fragment assignment was verified by amplifying each purified band RNA, using oligonucleotides flanking specific deletions. The assignment of the fragments was also confirmed by Northern-blot assay, using oligonucleotides mapping the DI-B regions that were not present in DI-C, and vice versa.

1.4.3 Cloning and Sequencing the Overlapping Fragments a, b, c, and d.

The four overlapping DNA fragments a (1.9 kb), b (2.8 kb), c (3.5 kb) and d (2.1 kb), complementary to RNA C, were cloned in Bluescript SK. At least two clones derived from independent RT-PCR reactions were sequenced. The sequence of the positions that did not coincide in the different clones (possibly errors of the Taq polymerase) were sequenced directly from the corresponding uncloned PCR products. Following this procedure, the RNA DI-C consensus sequence was determined. An average of 1 error of Taq polymerase was obtained each copied 1.2 kb. The complete sequence of the DI-C genome is shown on FIG. 12.

The complete RNA DI-C sequence obtained this way was compared with the ORFs 1a and 1b sequence of the PUR46-PAR virus [Eleouet et al., Virology 206, 817∫822 (1995)], and with the sequence determined in our laboratory for the other THER-1 virus ORFs. In the complete RNA DI-C sequence, 14 nucleotide differences were found in comparison with the sequence of strain PUR46-PAR. These positions were sequenced in strain THER-1, the parental virus of the defective genome, in order to define the specific changes of the genomic defective RNA DI-C. The DI-C RNA sequence only presented three nucleotide differences in comparison with the corresponding sequence of the parental virus, and one insertion in position 9189, which does not affect any ORF (FIG. 12).

1.4.4 Primary DI-C and DI-B Genome Structures.

The sequence data indicated that the DI-C genome was composed of four discontinuous parental genome regions (FIG. 13) comprising: a) the 2144 nucleotides of the 5' end of the genome; b) 4540 nucleotides corresponding to the region between positions 12195 and 16734 of the parental genome, which includes the overlapping area between ORFs 1a and 1b, and approximately the 5' half of ORF 1b; c) a region of 2531 nucleotides corresponding to positions 17843–20372 of the wild genome, and which comprises the 3' half of ORF1b and the first 8 gene S nucleotides; and d) the 493 nucleotides of the 3' end.

The primary structure of the DI-B genome was determined by sequencing of cloned fragments a and b (common to genome DI-C), c (like the parental genome) and d (specific to genome DI-B). Genome DI-B is composed of three discontinuous regions of the genome (FIG. 14): a) the 2144 nucleotides of the 5' end of the genome, common to all DI-B clones, and identical to region I of RNA DI-C; b) a region variable in size, of 8178–8243 nucleotides corresponding to positions 12195–20369 to 20436 of the parental genome, and which includes the overlapping zone between the two ORFs of gene 1, the complete ORF1b, and the first nucleotides of gene S; and c) nucleotides 278 to 303 of the 3' region of the genome.

The clones constituting the population designated as genomes DI-B differ in the size of the deletion that took place between regions II and III, which starts at the beginning of gene S (between nucleotides 6 and 73) and finishing at the end of gene 7 (between nucleotides 195 and 233).

The 5' end sequence of parental RNA THER-1 was determined by direct sequencing of the RNA, and is 5'-NCUUUUAAAG-3'. The nature of the first "N" nucleotide of the sequence has not been determined. So far, the sequence of the 5' end of three TGEV isolates, PUR46-PAR, PUR46-BRI and FS772/70, has been described [Eleouet et al., supra; Page et al., Virus Genes 4, 289–301 (1990); Sethna et al., J. Virol. 65, 320–325 (1991)] and they all differ in the first nucleotide. The sequence of the defective RNAs leader must be the same as that of the parental virus leader, in view of the interchange of leaders that takes place in a coronavirus infection [Makino et al., J. Virol. 57, 729–737 (1986)].

The three defective RNAs contain polyA, as they join themselves to oligo dT columns (results not shown).

1.4.5 RNAs B and C Keep the Overlapping Region between ORFs 1a and 1b, which Includes the Motive Responsible for the Translocation (−1) of the Ribosome In accordance with the sequences assigned to genomes DI-C and DI-B, it is possible to predict ORFs of 6370 and 10003 nucleotides, respectively, starting at nucleotide 315, counting from the 5' end of the genome. The RNA DI-C ORF ends at the termination codon generated at the joint site of discontinuous regions II and III, where the internal deletion had taken place in ORF 1b, at position 6685 of the DI-C genome. The DI-B genome ORF ends at the natural termination codon of ORF1b.

The two defective RNAs keep the overlapping zone between ORFs 1a and 1b, which includes the sliding sequence and the tertiary structure motive pseudoknot, responsible for the translocation (−1) of the ribosome in this zone (Eleouet et al., supra). FIG. 15 shows the possible RNA secondary and tertiary structures in this zone. The structure proposed by Eleouet et al. for the pseudoknot in this zone, is the one indicated in C and D; however, there are other possible structures (as indicated in A and B), although it is not know which is the correct one.

A description has been made, indicating that the translocation occurs with an efficiency of 20% in TGEV (Eleouet et al., supra) and enables the continuous translation of gene 1. The fact that RNAs DI-B and DI-C (and probably DI-A RNA) keep this region of 40 the parental genome suggests that it could be necessary for RNA replication or for genome propagation.

There are two other small ORFs in defective genomes DI-C and DI-B. One of them, previous to the long reading frame, codes for a peptide of three amino acids, which is also found in the wild type genome, whose function is unknown. The other ORF starts in both cases in the AUG of gene S, and codes for a peptide of 16 amino acids in DI-C, and a peptide of variable size in DI-B. It is unknown whether these ORFs are functional.

The only two transcription promoter consensus sequences (CUAAAC) of the virus that are precisely those preceding gene 1 and gene S, in defective RNAs B and C. These sequences are marked in FIG. 12.

FIG. 16 shows the mapping of RNAs A, B and C by hybridization with oligonucleotides specific to the virus in Northern-blot assays. The THER-1-STp41 virus RNA was fractioned in agarose gels until a clear separation of the RNAs from the parental genome and DI, A, B and C had been obtained. The RNA was transferred to nylon filters which hybridized with various oligonucleotides marked with $^{32}P_{I}$, hybridized with the parental genome (+), and hybridized (+) or not (−) with the defective genomes. The approximate locations of the sequences complementary to the oligonucleotides in the parental genome are shown marked with arrows. Their exact sequence and position appear in Table 3. All the oligonucleotides hybridized with the parental genome, and the expected results with RNAs B and C were obtained.

TABLE 3

| ON | ID Sec. No. | Polarity | Gene in TGEV | Position in the genome[a)] |
|---|---|---|---|---|
| 1 | 10 | – | Leader | 66–91 |
| 2 | 11 | – | ORF1a | 2151–2170 |
| 3 | 12 | – | ORF1a | 6121–6140 |
| 4 | 13 | – | ORF1a | 8684–8703 |
| 5 | 14 | – | ORF1a | 12261–12280 |
| 6 | 15 | – | ORF1b | 14148–14167 |
| 7 | 16 | – | ORF1b | 17363–17381 |
| 8 | 17 | – | ORF1b | 18792–18811 |
| 9 | 18 | – | gene S | 1055–1074 |
| 10 | 19 | – | gene S | 1980–1999 |
| 11 | 20 | – | gene S | 3600–3619 |
| 12 | 21 | – | gene M | 97–116 |
| 13 | 22 | – | gene N | 5–24 |
| 14 | 23 | – | UTR-3' | 28524–28543 |

[a)]The position in the genome is indicated as the number of bases starting from the 5' end of the wild type virus genome for oligonucleotides (ON) complementary to gene 1 (ORF1a and ORF1b) and the untranslated region of 3' end (3'-UTR): and from the first nucleotide of the primer ATG of the corresponding gene to nucleotide 5' of the ON in the case of primers mapping in genes S, M and N.

EXAMPLE 2

Generation of Expression Vectors

The cDNA coding for RNA DI-C has been cloned in a Bluescript II plasmid, under the control of the phage T7 promoter. This cDNA includes polyA sequences, a hepatitis delta virus (HDV) ribozyme, and phage T7 termination signals. One of these plasmids, whose construction appears in FIG. 17, has been denominated pDIC-1. These plasmids can be manipulated to clone in them heterologous genes under the control of the gene S promoter present in the defective genome, or another TGEV promoter, or a variant of them with increased efficiency.

The cloning of these heterologous genes was done after ORF1b, following the S gene initiation codon (AUG), and in reading phase with this gene.

From these cDNAs, RNAs were expressed using the phage T7 polymerase, with which ST cells that had been infected previously with the attenuated helper virus THER-1 were transformed, enabling to recover virions, containing the helper virus genome, and other virions, containing the corresponding defective genome. These viruses, freeze-dried in presence of 2% fetal calf serum, were used as vaccine for the induction of specific antibodies against agents that infect the gastrointestinal and respiratory tracts of pigs, dogs and rabbits.

The tropism of the vectors was specifically targeted to the porcine, canine, or feline species, using the appropriate attenuated helper viruses.

EXAMPLE 3

Induction of Neutralizing Antibodies 3.1 Induction of Protection Against Porcine Epidemic Diarrhea Coronavirus (PEDV)

Pigs were immunized using a recombinant system consisting of helper virus (THER-1), and the pDIC-1 plasmid in which the PEDV glycoprotein S gene had been cloned.

The immunizations were done by administering $10^9$ pfu per piglet, via oral route.

Presence of neutralizing antibodies was assayed in the sera of animals vaccinated at 15, 30, 45 and 60 days post immunization; and presence of antibodies specific to PEDV was determined using a radio immuno-assay (RIA) (Maniatis et al., supra).

With the sera collected on the 45th day post immunization, total protection was provided against infection by PEDV (strain SEG86-1) in 10-day-old piglets, when these sera had been pre-incubated with the virulent virus before oral administration.

3.2 Induction of Protection Against Canine Coronavirus

Dogs were immunized using a recombinant system consisting of helper virus (canine coronavirus strain Fort Dodge), and the pDIC-1 plasmid in which the canine coronavirus glycoprotein S gene had been cloned (strain Fort Dodge).

The immunizations were done by administering $10^9$ pfu per dog via oral route.

Presence of neutralizing antibodies in the sera of the animals vaccinated at 15, 30, 45 and 60 days post immunization was assayed, and presence of antibodies specific to canine coronavirus was determined using RIA.

With the sera collected on the 45th day post immunization, total protection was conferred against infection by canine coronavirus (strain Fort Dodge) in 10-day old puppies, when these sera were pre-incubated with the virulent virus before oral administration.

3.3 Induction of Protection Against Infections Caused by the Arterivirus PRRSV

Pigs were immunized using a recombinant system consisting of helper virus (THER-1), and pDIC-1 plasmid in which the arterivirus PRRSV ORF3 and ORF5 (strain Fort Dodge) had been cloned.

The immunizations were done by administering $10^9$ pfu per piglet, via oral route.

Presence of neutralizing antibodies was analyzed in the sera of the animals vaccinated at 15, 30, 45 and 60 days post immunization, and presence of antibodies specific to PRRSV was determined by RIA.

With the sera collected on the 45th day post immunization, total protection was provided against infection by PRRSV (strain Fort Dodge) in 10-day-old piglets, when these sera had been pre-incubated with the virulent virus before the administration via oral route.

EXAMPLE 4

Generation of Expression Vectors

Following a procedure similar to the one described in Example 2, a cDNA coding for an selfreplicative RNA has been cloned in a Bluescript II plasmid, under the control of the phage T7 promoter. This cDNA includes polyA sequences, a ribozyme of hepatitis delta virus (HDV) and the phage T7 termination signals. One of these plasmids, whose construction is shown in FIG. 18 has been denominated pDIA-6A.C3. This plasmid contains the gene coding for monoclonal antibody 6A.C3 which neutralizes TGEV. The characteristics of monoclonal antibody 6A.C3 and its construction are described in Dr. Joaquin Castilla Carrión's Doctoral Thesis, entitled "*Construcción de animales transgénicos secretores de anticuerpos neutralizantes para coronavirus*", Universidad Autónoma, Madrid, Faculty of Science, December 1996, pages 43–52, 65–79.

The cloning of the heterologous gene was done after ORF 1b, following the gene S initiation codon (AUG), and in reading frame with this gene.

Starting from this cDNA, RNAs were expressed using phage T7 polymerase, with which were transformed ST cells previously infected with the attenuated helper virus THER-1, resulting in the recovery of virions containing the helper virus genome and other virions with the corresponding defective genome. These viruses, freeze-dried in the presence of 2% fetal calf serum can be used as vectors for the expression of the recombinant 6A.C3 monoclonal antibody. The tropism of the vectors was made specifically for the porcine species using the appropriate attenuated helper virus.

EXAMPLE 5

Expression of Neutralizing Antibodies

Pigs were immunized using a recombinant system constituted of helper virus (THER-1), and the pDIA-6A.C3 plasmid (Example 4) containing the sequence coding for recombinant monoclonal antibody 6A.C3 which neutralizes TGEV.

The immunizations were done by administering $10^9$ pfu per piglet via oral route.

Presence of neutralizing 6A.C3 antibodies was assayed in the serum of animals vaccinated at 15, 30, 45 and 60 days post immunization using an RIA [Maniatis et al,. supra]. The recombinant antibodies had RIA titers higher than $10^3$ and are able to reduce the titer of the infectious virus more than $10^4$ fold.

Deposit of Microorganisms

The plasmid denominated pDIC-1, introduced in a DH-5 bacterium derived from *E. coli*, [DH5/pDIC-1], was deposited on 6th March 1996 at the European Collection of Animal Cell Cultures (ECACC), Porton Down, Salisbury, Wiltshire SP4 OJG, United Kingdom, with corresponding accession number P96030641.

Additionally, the attenuated helper virus denominated THER-1 was deposited at ECACC on 6th march 1996, with corresponding accession number V96030642.

What is claimed is:

1. A porcine vaccine against a pathogen of interest, wherein the vaccine comprises a helper virus, at least one recombinant virion, and a pharmaceutical excipient, wherein the recombinant virion(s) comprises:

(A) at least 1.9 kb of the 5' end of a TGEV genome;

(B) the pseudoknot region, including the region of overlap between ORFs 1a and 1b, of the TGEV genome;

(C) defective or missing S, M, and N structural genes of the TGEV genome;

(D) at least bp 9691–9707 of the 3' end of the TGEV genome; and (E) at least one heterologous gene sequence encoding an antigen of the pathogen of interest inserted under the control of the S gene promoter of the TGEV genome.

2. The vaccine as claimed in claim 1, wherein the pathogen has a tropism for enteric or respiratory mucosae.

3. The vaccine as claimed in claim 1, wherein the vaccine comprises more than one recombinant virion.

4. The vaccine as claimed in claim 1, wherein the virion comprises more than one heterologous gene sequence encoding an antigen of an infectious agent that infects porcine species.

5. A porcine vaccine against *Mycoplasma hyopneumoniae*, wherein the vaccine comprises a helper virus, at least one recombinant virion, and a pharmaceutical excipient, wherein the recombinant virion(s) comprises:

(A) at least 1.9 kb of the 5' end of a TGEV genome;

(B) the pseudoknot region, including the region of overlap between ORFs 1a and 1b, of the TGEV genome;

(C) defective or missing S, M, and N structural genes of the TGEV genome;

(D) at least bp 9691–9707 of the 3' end of the TGEV genome; and (E) at least one heterologous gene sequence encoding an antigen of *Mycoplasma hyopneumoniae*, inserted under the control of the S gene promoter of the TGEV genome.

6. A porcine vaccine against a pathogen of interest, wherein the vaccine comprises a helper virus, at least one recombinant virion, and a pharmaceutical excipient, wherein the recombinant virion(s) comprises:

(A) at least 1.9 kb of the 5' end of a TGEV genome;

(B) the pseudoknot region, including the region of overlap between ORFs 1a and 1b, of the TGEV genome;

(C) defective or missing S, M, and N structural genes of the TGEV genome;

(D) at least bp 9691–9707 of the 3' end of the TGEV genome; and (E) at least one heterologous gene sequence encoding an antigen of *Mycoplasma hyopneumoniae, Actinobacillus pleuropneumoniae, Actinobacillus suis, Haemophilus parasuis*, Porcine parvovirus, *Leptospira, Escherichia coli, Erysipelothrix rhusiopathiae, Pasteurella multocida, Bordetella bronchiseptica, Clostridium* sp., *Serpulina hyodisenteriae*, porcine epidemic diarrhea virus (PEDV), porcine respiratory coronavirus, rotavirus, the pathogens that cause porcine reproductive and respiratory syndrome (PRRSV), Aujeszky's disease (pseudorabies virus), swine influenza, transmissible gastroenteritis, and the etiologic agent of atrophic rhinitis and proliferative ileitis, inserted under the control of the S gene promoter of the TGEV genome.

7. The porcine vaccine as claimed in claim 6, wherein the heterologous gene in (E) encodes an antigen of PEDV.

8. The porcine vaccine as claimed in claim 6, wherein the heterologous gene in (E) encodes an antigen of PRRSV.

9. A porcine vaccine against a pathogen of interest, wherein the vaccine comprises at least one recombinant virion and a pharmaceutical excipient, wherein the recombinant virion(s) is prepared according to the method comprising:

(A) constructing a recombinant plasmid comprising a defective TGEV genome under the control of an RNA polymerase promoter, wherein the defective TGEV genome comprises:
   (1) at least 1.9 kb of the 5' end of the TGEV genome;
   (2) the pseudoknot region, including the region of overlap between ORFs 1a and 1b, of the TGEV genome;
   (3) incomplete S, M, and N structural genes of the TGEV genome;
   (4) at least bp 9691–9707 of the 3' end of the TGEV genome); and
   (5) at least one heterologous gene sequence encoding an antigen of the pathogen of interest inserted under the control of the S gene promoter of the TGEV genome;

(B) producing RNA of the sequences in (A) by transcribing the sequences from the RNA polymerase promoter;

(C) infecting cells with a helper virus;

(D) introducing the RNA produced in step (B) into the infected cells of step (C);

(E) producing a recombinant virion comprising a defective TGEV genome and heterologous gene under the control of the S gene promoter of the TGEV genome.

10. The vaccine as claimed in claim 7, wherein the pathogen has a tropism for enteric or respiratory mucosae.

11. The vaccine as claimed in claim 7, wherein the vaccine comprises more than one recombinant virion.

12. The vaccine as claimed in claim 7, wherein the virion comprises more than one heterologous gene sequence encoding an antigen of an infectious agent that infects porcine species.

13. A porcine vaccine against *Mycoplasma hyopneumoniae*, wherein the vaccine comprises at least one recombinant virion and a pharmaceutical excipient, wherein the recombinant virion(s) is prepared according to the method comprising:

(A) constructing a recombinant plasmid comprising a defective TGEV genome under the control of an RNA polymerase promoter, wherein the defective TGEV genome comprises:
   (1) at least 1.9 kb of the 5' end of the TGEV genome;
   (2) the pseudoknot region, including the region of overlap between ORFs 1a and 1b, of the TGEV genome;
   (3) incomplete S, M, and N structural genes of the TGEV genome;
   (4) at least bp 9691–9707 of the 3' end of the TGEV genome); and
   (5) at least one heterologous gene sequence encoding an antigen of *Mycoplasma hyopneumoniae*, inserted under the control of the S gene promoter of the TGEV genome;

(B) producing RNA of the sequences in (A) by transcribing the sequences from the RNA polymerase promoter;

(C) infecting cells with a helper virus;

(D) introducing the RNA produced in step (B) into the infected cells of step (C);

(E) producing a recombinant virion comprising a defective TGEV genome and heterologous gene under the control of the S gene promoter of the TGEV genome.

14. A porcine vaccine against a pathogen of interest, wherein the vaccine comprises at least one recombinant virion and a pharmaceutical excipient, wherein the recombinant virion(s) is prepared according to the method comprising:

(A) constructing a recombinant plasmid comprising a defective TGEV genome under the control of an RNA polymerase promoter, wherein the defective TGEV genome comprises:
   (1) at least 1.9 kb of the 5' end of the TGEV genome;
   (2) the pseudoknot region, including the region of overlap between ORFs 1a and 1b, of the TGEV genome;
   (3) incomplete S, M, and N structural genes of the TGEV genome;
   (4) at least bp 9691–9707 of the 3' end of the TGEV genome); and
   (5) at least one heterologous gene sequence encoding an antigen of *Mycoplasma hyopneumoniae, Actinobacillus pleuropneumoniae, Actinobacillus suis, Haemophilus parasuis*, Porcine parvovirus, *Leptospira, Escherichia coli, Erysipelothrix rhusiopathiae, Pasteurella multocida, Bordetella bronchiseptica, Clostridium* sp., *Serpulina hyodisenteriae*, porcine epidemic diarrhea virus (PEDV), porcine respiratory coronavirus, rotavirus, the pathogens that cause porcine reproductive and respiratory syndrome (PRRSV), Aujeszky's disease (pseudorabies virus), swine influenza, transmissible gastroenteritis, and the etiologic agent of atrophic rhinitis and proliferative ileitis, inserted under the control of the S gene promoter of the TGEV genome;

(B) producing RNA of the sequences in (A) by transcribing the sequences from the RNA polymerase promoter;

(C) infecting cells with a helper virus;

(D) introducing the RNA produced in step (B) into the infected cells of step (C);

(E) producing a recombinant virion comprising a defective TGEV genome and heterologous gene under the control of the S gene promoter of the TGEV genome.

15. The porcine vaccine as claimed in claim 14, wherein the heterologous gene in (5) encodes an antigen of PEDV.

16. The porcine vaccine as claimed in claim 14, wherein the heterologous gene in (5) encodes an antigen of PRRSV.

* * * * *

UNITED STATES PATENT AND TRADEMARK OFFICE

CERTIFICATE OF CORRECTION

PATENT NO. : 7,041,300 B1
APPLICATION NO. : 09/155003
DATED : May 9, 2006
INVENTOR(S) : Luis Enjuanes Sanchez et al.

It is certified that error appears in the above-identified patent and that said Letters Patent is hereby corrected as shown below:

In claim 9, column 53, line 15, “genome);” should read --genome;--.

In claim 13, column 53, line 53, “genome);” should read --genome;--.

In claim 14, column 54, line 27, “genome);” should read --genome;--.

Signed and Sealed this

Seventh Day of November, 2006

JON W. DUDAS
*Director of the United States Patent and Trademark Office*